(12) United States Patent
Shimono et al.

(10) Patent No.: US 9,902,865 B2
(45) Date of Patent: Feb. 27, 2018

(54) INK COMPOSITION, INKJET RECORDING METHOD, PRINTED MATTER, AND HIGH-MOLECULAR-WEIGHT POLYMERIZATION INITIATOR

(71) Applicant: FUJIFILM Corporation, Tokyo (JP)

(72) Inventors: Katsuhiro Shimono, Kanagawa (JP); Reiko Fukagawa, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 174 days.

(21) Appl. No.: 14/820,377

(22) Filed: Aug. 6, 2015

(65) Prior Publication Data

US 2015/0344711 A1    Dec. 3, 2015

Related U.S. Application Data

(63) Continuation of application No. PCT/JP2014/050045, filed on Jan. 7, 2014.

(30) Foreign Application Priority Data

Feb. 21, 2013 (JP) ................. 2013-032122
Dec. 19, 2013 (JP) ................. 2013-262182

(51) Int. Cl.
| | |
|---|---|
| *C09D 11/322* | (2014.01) |
| *C08F 222/10* | (2006.01) |
| *B41J 2/01* | (2006.01) |
| *C09D 133/14* | (2006.01) |
| *C09D 11/101* | (2014.01) |

(Continued)

(52) U.S. Cl.
CPC ............. *C09D 11/322* (2013.01); *B41J 2/01* (2013.01); *C07F 9/5337* (2013.01); *C08F 2/50* (2013.01); *C08F 222/10* (2013.01); *C09B 69/109* (2013.01); *C09D 11/101* (2013.01);

(Continued)

(58) Field of Classification Search
None
See application file for complete search history.

(56) References Cited

U.S. PATENT DOCUMENTS

| | | | |
|---|---|---|---|
| 6,849,669 | B1 | 2/2005 | Hodd et al. |
| 2005/0245768 | A1 | 11/2005 | Wolf |

(Continued)

FOREIGN PATENT DOCUMENTS

| | | |
|---|---|---|
| CN | 1721463 A | 1/2006 |
| CN | 1896083 A | 1/2007 |

(Continued)

OTHER PUBLICATIONS

The extended European search report issued by the European Patent Office dated Mar. 16, 2016, which corresponds to European Patent Application No. 14753927.4-1302 and is related to U.S. Appl. No. 14/820,377.

(Continued)

*Primary Examiner* — Gerard Higgins
*Assistant Examiner* — Sathavaram I Reddy
(74) *Attorney, Agent, or Firm* — Studebaker & Brackett PC

(57) ABSTRACT

An ink composition contains (component A) a high-molecular-weight polymerization initiator having a weight-average molecular weight of equal to or greater than 1,000, (component B) a polymerizable compound, and (component C) a colorant, in which the component A has an acylphosphine oxide structure, and the acylphosphine oxide structure is linked to a main chain or a core of the component A on the side of an acyl group thereof.

16 Claims, 1 Drawing Sheet

(51) Int. Cl.
*C09D 11/38* (2014.01)
*C08F 2/50* (2006.01)
*C07F 9/53* (2006.01)
*C09B 69/10* (2006.01)
*C08F 230/02* (2006.01)

(52) U.S. Cl.
CPC ............ *C09D 11/38* (2013.01); *C09D 133/14* (2013.01); *C08F 230/02* (2013.01); *Y10T 428/24901* (2015.01)

(56) References Cited

U.S. PATENT DOCUMENTS

| | | |
|---|---|---|
| 2006/0004116 A1 | 1/2006 | Kishi et al. |
| 2009/0087627 A1 | 4/2009 | Watanabe et al. |
| 2010/0168359 A1 | 7/2010 | Domschke et al. |
| 2012/0046376 A1 | 2/2012 | Loccufier et al. |
| 2012/0133060 A1 | 5/2012 | Nakane et al. |

FOREIGN PATENT DOCUMENTS

| | | |
|---|---|---|
| CN | 1961051 A | 5/2007 |
| CN | 101397424 A | 4/2009 |
| CN | 102241792 A | 11/2011 |
| EP | 1616920 A1 | 1/2006 |
| EP | 1616921 A1 | 1/2006 |
| EP | 2053101 A1 | 4/2009 |
| GB | 2412660 A | 10/2005 |
| JP | 2005-307199 A | 11/2005 |
| JP | 2006-307151 A | 11/2006 |
| JP | 2007-277380 A | 10/2007 |
| JP | 2009-084313 A | 4/2009 |
| JP | 2009-084424 A | 4/2009 |
| JP | 2010-116460 A | 5/2010 |
| JP | 2011-500932 A | 1/2011 |
| JP | 2012-046456 A | 3/2012 |
| JP | 2012-116933 A | 6/2012 |
| JP | 2012-513998 A | 6/2012 |
| WO | 2003/009014 A1 | 1/2003 |
| WO | 03/068785 A1 | 8/2003 |
| WO | 2010/133381 A1 | 11/2010 |

OTHER PUBLICATIONS

J. H. De Groot, et al.; "Injectable Intraocular Lens Materials Based Upon Hydrogels"; Jul. 25, 2001; pp. 628-634; vol. 2, No. 3; Biomacromolecules, American Chemical Society, U.S.

An Office Action; "Notification of Reasons for Refusal" issued by the Japanese Patent Office dated Apr. 26, 2016, which corresponds to Japanese Patent Application No. 2013-262182 and is related to U.S. Appl. No. 14/820,377; with English language translation.

An Office Action; "First Notice of Opinion on Examination" issued by the State Intellectual Property Office of People's Republic of China dated Apr. 21, 2016, which corresponds to Chinese Patent Application No. 201480007869.7 and is related to U.S. Appl. No. 14/820,377; with English language translation.

Valter Castelvetro et al.; "UV-Curing of Acrylic Formulations by Means of Polymeric Photoiniiators with the Active 2,6-Dimethylbenzoylphophine Oxide Moieties Pendant from a Tetramethylene Side Chain"; Macromolecular Chemistry and Physics; Jul. 29, 2002; pp. 1486-1496; vol. 203; No. 10/11.

International Search Report for application No. PCT/JP2014/050045 dated Apr. 15, 2014.

A Supplementary Partial European Search Report issued by the European Patent Office dated Oct. 29, 2015, which corresponds to European Patent Application No. 14753927.4-1302 and is related to U.S. Appl. No. 14/820,377.

An Office Action issued by the European Patent Office dated Nov. 2, 2017, which corresponds to European Patent Application No. 14753927.4-1302 and is related to U.S. Appl. No. 14/820,377.

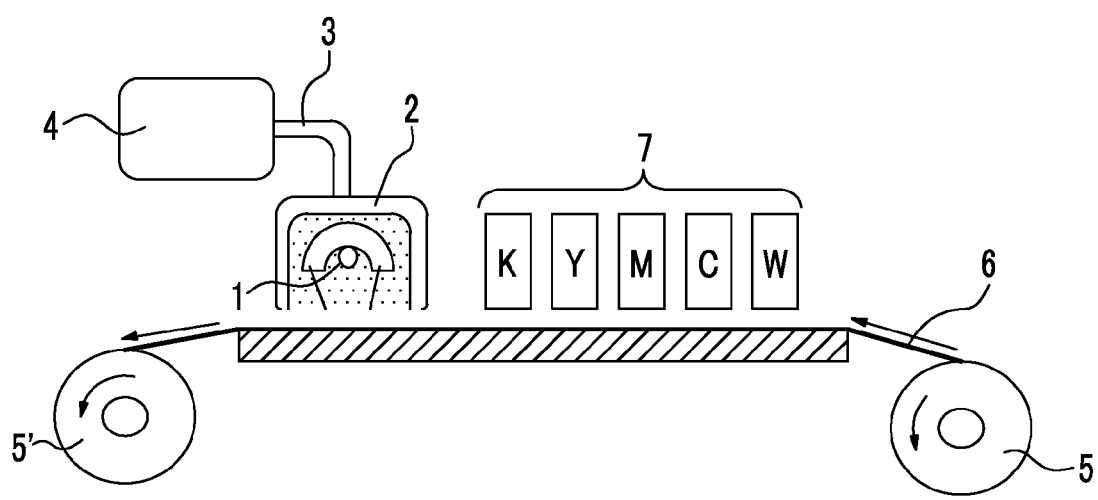

INK COMPOSITION, INKJET RECORDING METHOD, PRINTED MATTER, AND HIGH-MOLECULAR-WEIGHT POLYMERIZATION INITIATOR

CROSS-REFERENCE TO RELATED APPLICATIONS

This application is a Continuation of PCT International Application No. PCT/JP2014/050045 filed on Jan. 7, 2014, which claims priority under 35 U.S.C. § 119(a) to Japanese Patent Application No. 2013-032122 filed on Feb. 21, 2013 and Japanese Patent Application No. 2013-262182 filed on Dec. 19, 2013. Each of the above application(s) is hereby expressly incorporated by reference, in its entirety, into the present application.

BACKGROUND OF THE INVENTION

1. Field of the Invention

The present invention relates to an ink composition, an inkjet recording method, a printed article, and a high-molecular-weight polymerization initiator.

2. Description of the Related Art

In recent years, as an image recording method for forming an image on a recording medium based on image data signals, an inkjet recording method has drawn attention. By the inkjet recording method, little noise is generated, and extremely minute liquid droplets are ejected. Therefore, the inkjet recording method has an advantage in that the method makes it possible to obtain an extremely vivid image at low running cost.

Particularly, in an ink composition for inkjet recording that can be cured by being irradiated with radiation such as ultraviolet rays (a radiation-curable ink composition for inkjet recording), most components of the ink composition are cured by being irradiated with radiation such as ultraviolet rays, and therefore, drying properties of the ink composition are better than those of a solvent-based ink composition. Furthermore, preventing an image from easily blurring, the aforementioned ink composition can be used for printing performed on various recording media, and accordingly, the ink composition is excellent means.

An example of an inkjet ink composition of the related art includes the ink composition disclosed in JP2011-500932A. Furthermore, examples of acylphosphine oxide compounds of the related art include the compounds disclosed in WO03/068785A, CN1896083A, and JP2012-46456A.

SUMMARY OF THE INVENTION

When an inkjet ink is used for foods or toys, no component should be volatilized or eluted from the ink image, or the level of volatilization or elution should be extremely low. However, a photocurable inkjet ink has a problem in that an unreacted polymerization initiator or a decomposition product of a polymerization initiator remains in the form of a low-molecular-weight polymerization initiator in a film, and is volatilized or eluted from the film.

As a solution to this problem, JP2011-500932A discloses a radically curable liquid containing a polymerizable initiator. Furthermore, JP2011-500932A also discloses an acylphosphine oxide compound having a polymerizable functional group. When such a compound is used, phosphonoyl radicals are incorporated into a film, but benzoyl radicals having lower reactivity are not incorporated into the cured film. Consequently, a benzaldehyde compound is eluted from the film, and this leads to a problem in that the safety of the ink composition does not reach a desired level. The acylphosphine oxide compound also has a problem in that due to the low-molecular-weight compound remaining in the film, the adhesiveness of the ink composition with respect to a substrate deteriorates.

An object of the present invention is to provide an ink composition, which exhibits excellent adhesiveness with respect to a recording medium, reduces the amount of components in a cured ink film that are eluted (migrate) to the outside, and suppresses the odor of a printed article. Another object of the present invention is to provide an inkjet recording method and a printed article that use the ink composition.

Another object of the present invention is to provide a novel high-molecular-weight polymerization initiator.

The above objects of the present invention were achieved by the means described in the following <1> or <12> to <15>. Hereinafter, the means are described together with <2> to <11> which are preferable embodiments of the present invention.

<1> An ink composition containing (component A) a high-molecular-weight polymerization initiator having a weight-average molecular weight of equal to or greater than 1,000, (component B) a polymerizable compound, and (component C) a colorant, in which the component A has an acylphosphine oxide structure, and the acylphosphine oxide structure is linked to a main chain or a core of the component A on the side of an acyl group thereof.

<2> The ink composition described in <1>, in which the acylphosphine oxide structure is a monoacylphosphine oxide structure.

<3> The ink composition described in <1> or <2>, in which the acylphosphine oxide structure is a structure represented by the following Formula (1) or (2).

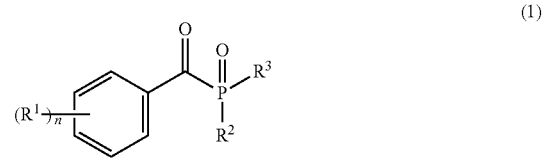

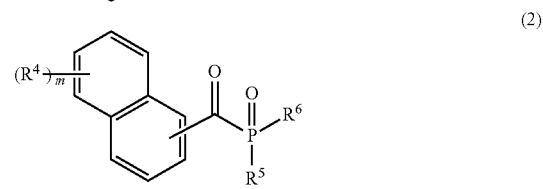

In the formula, each $R^1$ independently represents an alkyl group having 1 to 8 carbon atoms, an aryl group, an alkoxy group having 1 to 4 carbon atoms, or a linking group linked to a main chain or a core of the component A; at least one $R^1$ is a linking group linked to a main chain or a core of the component A; each of $R^2$ and $R^3$ independently represents an alkyl group, an aryl group, or an alkoxy group; n represents an integer of 1 to 5; each $R^4$ independently represents an alkyl group having 1 to 8 carbon atoms, an aryl group, an alkoxy group having 1 to 4 carbon atoms, or a linking group linked to a main chain or a core of the component A; at least one $R^4$ is a linking group linked to a main chain or a core of the component A; each of $R^5$ and $R^6$ independently represents an alkyl group, an aryl group, or an alkoxy group; and m represents an integer of 1 to 7.

<4> The ink composition described in <3>, in which the acylphosphine oxide structure is a structure represented by Formula (1).

<5> The ink composition described in <3>, in which the acylphosphine oxide structure is a structure represented by Formula (2).

<6> The ink composition described in any one of <1> to <5>, in which the component A is a (meth)acryl resin having the acylphosphine oxide structure on a side chain thereof.

<7> The ink composition described in any one of <1> to <5>, in which the component A is a hyperbranched polymer having the acylphosphine oxide structure, and the acylphosphine oxide structure is bonded to the core of the hyperbranched polymer.

<8> The ink composition described in any one of <1> to <7>, in which the acylphosphine oxide structure is a structure represented by the following Formula (1-1).

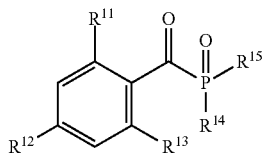

(1-1)

In the formula, each of $R^{11}$ to $R^{13}$ independently represents a hydrogen atom, an alkyl group having 1 to 8 carbon atoms, an aryl group, an alkoxy group having 1 to 4 carbon atoms, or a linking group linked to a main chain or a core of the component A; at least one of $R^{11}$ to $R^{13}$ is a linking group linked to a main chain or a core of the component A; and each of $R^{14}$ and $R^{15}$ independently represents an alkyl group, an aryl group, or an alkoxy group.

<9> The ink composition described in any one of <1> to <8>, in which the acylphosphine oxide structure is a structure represented by the following Formula (1-2).

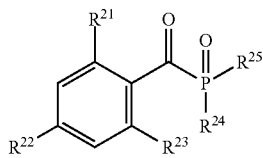

(1-2)

In the formula, $R^{21}$ represents a hydrogen atom, an alkyl group having 1 to 8 carbon atoms, an aryl group, or an alkoxy group having 1 to 4 carbon atoms; one of $R^{22}$ and $R^{23}$ represents a linking group linked to a main chain or a core of the component A, and the other of $R^{22}$ and $R^{23}$ represents a hydrogen atom, an alkyl group having 1 to 8 carbon atoms, an aryl group, or an alkoxy group having 1 to 4 carbon atoms; and each of $R^{24}$ and $R^{25}$ independently represents an alkyl group, an aryl group, or an alkoxy group.

<10> The ink composition described in any one of <1> to <9>, further containing a compound represented by the following Formula (3).

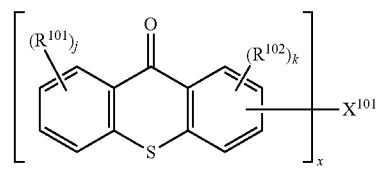

(3)

In the formula, each of $R^{101}$ and $R^{102}$ independently represents an alkyl group having 1 to 5 carbon atoms or a halogen atom; x represents an integer of 2 to 4; j represents an integer of 0 to 4; k represents an integer of 0 to 3; when each of j and k is an integer of equal to or greater than 2, a plurality of $R^{101}$ and a plurality of $R^{102}$ may be the same as or different from each other respectively; and $X^{101}$ represents an x-valent hydrocarbon chain having 2 to 300 carbon atoms that may contain an ether bond and/or an ester bond.

<11> The ink composition described in any one of <1> to <10> that is an inkjet ink composition.

<12> The ink composition described in any one of <1> to <11> that is an ink composition for printing a food package.

<13> An inkjet recording method includes ($a^1$) ejecting the ink composition described in any one of <1> to <12> onto a recording medium; and ($b^1$) curing the ink composition by irradiating the ejected ink composition with an active energy ray.

<14> A printed article produced by using the inkjet recording method described in <13>.

<15> A high-molecular-weight polymerization initiator which is a (meth)acryl resin having a weight-average molecular weight of equal to or greater than 1,000 and an acylphosphine oxide structure represented by the following Formula (1) or (2) on a side chain thereof

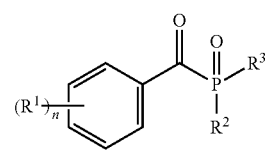

(1)

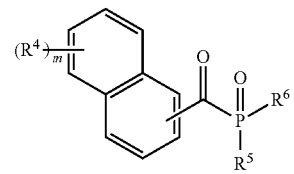

(2)

In the formula, each $R^1$ independently represents an alkyl group having 1 to 8 carbon atoms, an aryl group, an alkoxy group having 1 to 4 carbon atoms, or a linking group linked to a main chain of a (meth)acryl resin; at least one $R^1$ is a linking group linked to a main chain of a (meth)acryl resin; each of $R^2$ and $R^3$ independently represents an alkyl group, an aryl group, or an alkoxy group; n represents an integer of 1 to 5; each $R^4$ independently represents an alkyl group having 1 to 8 carbon atoms, an aryl group, an alkoxy group having 1 to 4 carbon atoms, or a linking group linked to a main chain of a (meth)acryl resin; at least one $R^4$ is a linking group linked to a main chain of a (meth)acryl resin; each of $R^5$ and $R^6$ independently represents an alkyl group, an aryl group, or an alkoxy group; and m represents an integer of 1 to 7.

<16> A high-molecular-weight polymerization initiator which is a hyperbranched polymer having a weight-average molecular weight of equal to or greater than 1,000 and one or more acylphosphine oxide structures represented by the following Formula (1) or (2) on a molecular terminal thereof

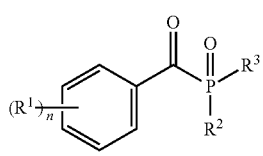

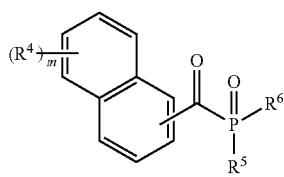

In the formula, each $R^1$ independently represents an alkyl group having 1 to 8 carbon atoms, an aryl group, an alkoxy group having 1 to 4 carbon atoms, or a linking group linked to a core of a hyperbranched polymer; at least one $R^1$ is a linking group linked to a core of a hyperbranched polymer; each of $R^2$ and $R^3$ independently represents an alkyl group, an aryl group, or an alkoxy group; n represents an integer of 1 to 5; each $R^4$ independently represents an alkyl group having 1 to 8 carbon atoms, an aryl group, an alkoxy group having 1 to 4 carbon atoms, or a linking group linked to a core of a hyperbranched polymer; at least one $R^4$ is a linking group linked to a core of a hyperbranched polymer; each of $R^5$ and $R^6$ independently represents an alkyl group, an aryl group, or an alkoxy group; and m represents an integer of 1 to 7.

<17> The high-molecular-weight polymerization initiator described in <16>, in which the hyperbranched polymer has 3 to 10 of acylphosphine oxide structures represented from the Formula (1) or (2).

<18> The ink composition comprises the high-molecular-weight polymerization initiator described in <15> or <16>.

According to the present invention, it is possible to provide an ink composition, which exhibits excellent adhesiveness with respect to a recording medium (a support, a recording material, or the like), reduces the amount of components in a cured ink film that are eluted (migrate) to the outside, and suppresses the odor of a printed article. Furthermore, it is possible to provide an inkjet recording method and a printed article that use the ink composition.

In addition, according to the present invention, it is possible to provide a novel high-molecular-weight polymerization initiator.

BRIEF DESCRIPTION OF THE DRAWING

FIG. 1 is a schematic view showing an example of an inkjet recording apparatus preferably used in the present invention.

DESCRIPTION OF THE PREFERRED EMBODIMENTS

Hereinafter, the present invention will be specifically described.

In the present specification, "xx to yy" represents a range of numerical values including xx and yy.

"(Meth)acrylate" or the like has the same definition as "acrylate and/or methacrylate" or the like, and the same will be applied hereinbelow.

"(Component A) a high-molecular-weight polymerization initiator having a weight-average molecular weight of equal to or greater than 1,000" or the like is simply referred to as "component A" or the like.

In the present invention, "% by mass" has the same definition as "% by weight", and "part by mass" has the same definition as "part by weight".

Hereinafter, the present invention will be specifically described.

(Ink Composition)

The ink composition of the present invention contains (component A) a high-molecular-weight polymerization initiator having a weight-average molecular weight of equal to or greater than 1,000, (component B) a polymerizable compound, and (component C) a colorant, in which the component A has an acylphosphine oxide structure, and the acylphosphine oxide structure is bonded to a main chain or a core of the component A on the side of an acyl group thereof.

The ink composition of the present invention is an ink composition that can be cured by an active energy ray. The "active energy ray" is energy-giving radiation that generates a polymerization initiating species in the ink composition by being radiated to the ink composition. The active energy ray includes an α ray, a γ ray, an X ray, an ultraviolet ray, a visible ray, an infrared ray, an electron beam, and the like. Among these, from the viewpoint of curing sensitivity and easy availability of the apparatus, the ultraviolet ray and the electron beam are preferable, and the ultraviolet ray is more preferable. For example, a peak wavelength of the active energy ray is preferably 200 nm to 600 nm, more preferably 300 nm to 450 nm, and even more preferably 320 nm to 420 nm, although the peak wavelength also depends on the absorption characteristics of a sensitizer. The active energy ray is particularly preferably an ultraviolet ray of which the peak wavelength is within a range of 340 nm to 400 nm.

Furthermore, the ink composition of the present invention is preferably an active energy ray-curable ink composition and an oleaginous ink composition. The ink composition of the present invention preferably does not contain water and a volatile solvent as far as possible. Even if the ink composition contains water and a volatile solvent, the amount of water and a volatile solvent is preferably equal to or less than 5% by mass, more preferably equal to or less than 1% by mass, and even more preferably equal to or less than 0.5% by mass, with respect to the total mass of the ink composition.

The ink composition of the present invention can be preferably used as an ink composition for inkjet recording (the ink composition is also referred to as an "inkjet ink composition").

Moreover, the ink composition of the present invention can be preferably used as both an ink composition for printing a package and an inkjet ink composition for printing a package.

The acylphosphine oxide compound is decomposed by light and generates benzoyl radicals and phosphinoyl radicals. The reactivity of the benzoyl radicals is lower than the reactivity of the phosphinoyl radicals. Therefore, in the cured ink film, a benzaldehyde compound, which is generated from the unreacted benzoyl radicals that did not participate in curing, remains in a large amount. Furthermore, the polymerization initiator is not entirely decomposed, and the unreacted acylphosphine oxide compound also remains in the film.

As a result of conducting examination in detail, the present inventor found that if an ink composition containing a high-molecular-weight polymerization initiator, which is bonded to a high-molecular-weight chemical structure on the side of an acyl group of an acylphosphine oxide structure, is used, the aforementioned two compounds that easily remain are incorporated into the film together with a polymerizable compound, and accordingly, it is possible to reduce the amount of a low-molecular-weight compound eluted from an image formed of the ink composition and to reduce the odor generated from the image.

For example, a printed mater obtained by inkjet printing using the active energy ray-curable ink composition of the related art has a problem in that the unreacted polymerization initiator, the residue of the polymerization initiator, or the like is bled out of the cured film. Particularly, when the active energy ray-curable ink composition is used for printing a package for packing food or the like, there is a problem in that a so-called migration (elution, transfer) amount, which is the amount of components transferred to the content of the package, is great. Furthermore, there is also a problem in that the cured film has strong odor, and the odor permeates the content or the surrounding food. In addition, there is also a problem in that because the low-molecular-weight compound remains in the film, the strength of the film is reduced, and the adhesiveness between the film and a support deteriorates.

If the ink composition of the present invention is used, it is possible to provide a printed article which exhibits excellent adhesiveness with respect to a recording medium and in which the amount of the components in the film that are eluted (migrate) to the outside is reduced and the odor is suppressed.

Hereinafter, the ink composition of the present invention will be specifically described.

(Component A) a High-Molecular-Weight Polymerization Initiator Having Weight-Average Molecular Weight of Equal to or Greater than 1,000

The ink composition of the present invention contains (component A) a high-molecular-weight polymerization initiator having a weight-average molecular weight of equal to or greater than 1,000. The component A has an acylphosphine oxide structure, and the acylphosphine oxide structure is bonded to a main chain or a core of the component A on the side of an acyl group thereof.

The weight-average molecular weight (Mw) of the component A is equal to or greater than 1,000. It is preferably 1,000 to 100,000, more preferably 1,000 to 50,000, even more preferably 1,000 to 10,000, particularly preferably 1,000 to 4,000, and most preferably 1,000 to 3,000. If the weight-average molecular weight is within the above range, it is possible to reduce the amount of the low-molecular-weight compound eluted from the obtained image and to reduce the odor generated from the obtained image. Furthermore, the curability and the compatibility between the component A and the polymerizable compound become excellent.

The component A is a high-molecular-weight polymerization initiator. When the component A has a general resin structure, the acylphosphine oxide structure is bonded to a main chain of a high-molecular-weight portion on the side of an acyl group of the acylphosphine oxide structure. When the component A is a hyperbranched polymer such as a dendrimer, a dendritic polymer, or a star polymer, the acylphosphine oxide structure is bonded to a core of a high-molecular-weight portion on the side of an acyl group of the acylphosphine oxide structure. The acylphosphine oxide structure in the component A used in the present invention is a structure which has an acyl moiety (hereinafter, also referred to as an "acyl group") and a phosphine oxide moiety and in which carbon atoms of a carbonyl group in the acyl moiety are bonded to phosphorus atoms of a phosphine oxide moiety.

In the present specification, a state in which the acylphosphine oxide structure is bonded (linked) to a main chain or a core of the component A on the side of an acyl group thereof means that the acyl moiety of the acylphosphine oxide structure is bonded (linked) to a main chain or a core of the component A through a linking group.

The weight-average molecular weight in the present specification can be measured by, for example, gel permeation chromatography (GPC). Specifically, it can be measured under the following conditions.

Column: TSKgel GMH×L, TSKgel G4000H×L, TSKgel G2000H×L (all manufactured by TOSOH CORPORATION)
Solvent: tetrahydrofuran (THF)
Standard substance: polystyrene
Detector: differential refractometer The component A preferably has a monoacylphosphine oxide structure or a bisacylphosphine oxide structure. From the viewpoint of manufacture, the component A more preferably has a monoacylphosphine oxide structure. If such an embodiment is adopted, it is possible to further reduce the amount of the low-molecular-weight compound eluted from the obtained image and to further reduce the odor generated from the obtained image, and inkjet ejectability and dispersion stability of the ink composition become better.

When the component A has a bisacylphosphine oxide structure, the bisacylphosphine oxide structure may be bonded to a main chain or a core of the component A on the side of at least one of two acyl groups bonded to phosphorus atoms. However, it is preferable that the bisacylphosphine oxide structure is bonded to a main chain or a core of the component A on the side of both of two acyl groups bonded to phosphorus atoms. If such an embodiment is adopted, it is possible to further reduce the amount of the low-molecular-weight compound eluted from the obtained image and to further reduce the odor generated from the obtained image.

The acylphosphine oxide structure can be bonded to a main chain or a core of the component A in any position of the acyl group. The number of the bond may be equal to or greater than 1 for a single acyl group. However, from the viewpoint of manufacturing suitability, the number of the bond is preferably 1 for a single acyl group.

The acyl group the component A has may be an aliphatic acyl group or an aromatic acyl group. However, from the viewpoint of absorption wavelength, the acyl group is preferably an aromatic acyl group, and more preferably a benzoyl group which may have a substituent and is bonded to a main chain or a core of the component A directly or through a linking group.

In a case in which the acyl group is the benzoyl group, provided that a binding position of a carbonyl group on a benzene ring is the 1-position, a binding position of the benzoyl group in which the benzoyl group is bonded to a main chain or a core of the component A directly or through a linking group is preferably at least one of the 2-position, the 4-position, and the 6-position. From the viewpoint of manufacturing suitability, the binding position of the benzoyl group is preferably at least the 4-position.

The acyl group in the component A can have any substituent in addition to the linking group linked to a main chain or a core of the component A. Examples of the substituent preferably include an alkyl group, an aryl group, and an alkoxy group, more preferably include an alkyl group having 1 to 8 carbon atoms, an aryl group having 6 to 12 carbon atoms, and an alkoxy group having 1 to 4 carbon atoms, and particularly preferably include a methyl group.

The linking group linked to a main chain or a core of the component A is not particularly limited. However, examples thereof preferably include a chain-like or cyclic alkylene group having 1 to 12 carbon atoms, a chain-like or cyclic alkenylene group having 2 to 12 carbon atoms, an arylene group having 6 to 12 carbon atoms, and a divalent group obtained by combining one or more alkylene groups, alkenylene groups, and/or arylene groups described above with one or more ester bonds, ether bonds, thioether bonds, or urethane bonds. The linking group linked to a main chain or a core of the component A preferably has 1 to 40 carbon atoms, more preferably has 1 to 20 carbon atoms, and even more preferably has 1 to 12 carbon atoms.

The acylphosphine oxide structure in the component A is preferably a structure represented by the following Formula (1) or (2).

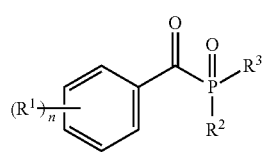

(1)

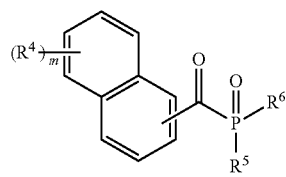

(2)

In the formula, each $R^1$ independently represents an alkyl group having 1 to 8 carbon atoms, an aryl group, an alkoxy group having 1 to 4 carbon atoms, or a linking group linked to a main chain or a core of the component A; at least one $R^1$ is a linking group linked to a main chain or a core of the component A; each of $R^2$ and $R^3$ independently represents an alkyl group, an aryl group, or an alkoxy group; n represents an integer of 1 to 5; each $R^4$ independently represents an alkyl group having 1 to 8 carbon atoms, an aryl group, an alkoxy group having 1 to 4 carbon atoms, or a linking group linked to a main chain or a core of the component A; at least one $R^4$ is a linking group linked to a main chain or a core of the component A; each of $R^5$ and $R^6$ independently represents an alkyl group, an aryl group, or an alkoxy group; and m represents an integer of 1 to 7.

In Formula (1), the binding position in which $R^1$ is bonded to a benzene ring is not particularly limited and may be arbitrarily set.

n is preferably an integer of 1 to 3, more preferably 2 or 3, and particularly preferably 3.

In Formula (2), the binding position in which $R^4$ or a carbonyl group bonded to a phosphorus atom is bonded to a naphthalene ring is not particularly limited, and may be arbitrarily set. In Formula (2), the binding position in which the carbonyl group bonded to a phosphorus atom is bonded to a naphthalene ring is preferably the 1-position of the naphthalene ring.

m is preferably an integer of 1 to 3, more preferably 1 or 2, and even more preferably 1. In Formula (2), the binding position in which $R^4$ is bonded to a naphthalene ring is preferably at least the 2-position of the naphthalene ring.

Each of $R^2$, $R^3$, $R^5$, and $R^6$ is preferably independently an alkyl group having 1 to 20 carbon atoms or an aryl group having 6 to 20 carbon atoms, more preferably an alkyl group having 1 to 12 carbon atoms or an aryl group having 6 to 12 carbon atoms, even more preferably an aryl group having 6 to 12 carbon atoms, and particularly preferably a phenyl group. The alkyl group and the aryl group may be substituted. Examples of the substituent include an alkyl group, an alkoxy group, an aryl group, and a halogen atom.

When there are a plurality of $R^1$ and a plurality of $R^4$, each of $R^1$ and $R^4$ is preferably independently an alkyl group having 1 to 8 carbon atoms, an aryl group, or a linking group linked to a main chain or a core of the component A, more preferably an alkyl group having 1 to 8 carbon atoms or a linking group linked to a main chain or a core of the component A, and even more preferably a methyl group or a linking group linked to a main chain or a core of the component A. Herein, at least one of $R^1$ and $R^4$ is a linking group linked to a main chain or a core of the component A. If such an embodiment is adopted, a printed article is obtained in which migration of the components in the film is further reduced, and odor is further reduced.

When the component A contains a plurality of groups represented by Formula (1) or (2), two or more of the groups represented by Formula (1) or (2) may be the same as or different from each other, but it is preferable for the groups to be the same as each other.

The acylphosphine oxide structure in the component A is more preferably a structure represented by the following Formula (1-1). Furthermore, Formula (1) is more preferably the following Formula (1-1).

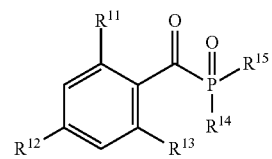

(1-1)

In the formula, each of $R^{11}$ to $R^{13}$ independently represents a hydrogen atom, an alkyl group having 1 to 8 carbon atoms, an aryl group, an alkoxy group having 1 to 4 carbon atoms, or a linking group linked to a main chain or a core of the component A; at least one of $R^{11}$ to $R^{13}$ is a linking group linked to a main chain or a core of the component A; and each of $R^{14}$ and $R^{15}$ independently represents an alkyl group, an aryl group, or an alkoxy group.

Each of $R^{11}$ to $R^{13}$ is preferably independently a hydrogen atom, an alkyl group having 1 to 8 carbon atoms, or a linking group linked to a main chain or a core of the component A, more preferably an alkyl group having 1 to 8 carbon atoms or a linking group linked to a main chain or a core of the component A, and even more preferably a methyl group or a linking group linked to a main chain or a core of the component A. If such an embodiment is adopted, a printed article is obtained in which migration of the components in the film is further reduced, and odor is further reduced.

The aryl group represented by $R^{11}$ to $R^{13}$ is preferably an aryl group having 6 to 20 carbon atoms.

Each of $R^{14}$ and $R^{15}$ is preferably independently an alkyl group having 1 to 20 carbon atoms or an aryl group having 6 to 20 carbon atoms, more preferably an alkyl group having 1 to 12 carbon atoms or an aryl group having 6 to 12 carbon atoms, even more preferably an aryl group having 6 to 12 carbon atoms, and particularly preferably a phenyl group. The alkyl group and the aryl group may be substituted. Examples of the substituent include an alkyl group, an alkoxy group, an aryl group, and a halogen atom.

The linking group represented by $R^{11}$ to $R^{13}$ that is linked to a main chain or a core of the component A is preferably a linking group bonded to a benzene ring through a methylene group.

The acylphosphine oxide structure in the component A is even more preferably a structure represented by the following Formula (1-2). Furthermore, Formula (1) is even more preferably the following Formula (1-2).

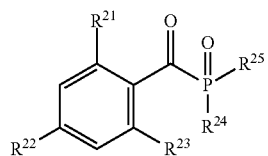

(1-2)

In the formula, $R^{21}$ represents a hydrogen atom, an alkyl group having 1 to 8 carbon atoms, an aryl group, or an alkoxy group having 1 to 4 carbon atoms; one of $R^{22}$ and $R^{23}$ represents a linking group linked to a main chain or a core of the component A, and the other of $R^{22}$ and $R^{23}$ represents a hydrogen atom, an alkyl group having 1 to 8 carbon atoms, an aryl group, or an alkoxy group having 1 to 4 carbon atoms; and each of $R^{24}$ and $R^{25}$ independently represents an alkyl group, an aryl group, or an alkoxy group.

$R^{21}$ is preferably a hydrogen atom or an alkyl group having 1 to 8 carbon atoms, more preferably an alkyl group having 1 to 8 carbon atoms, and even more preferably a methyl group. If such an embodiment is adopted, a printed article is obtained in which migration of the components in the film is further reduced, and odor is further reduced.

The linking group represented by one of $R^{22}$ and $R^{23}$ that is linked to a main chain or a core of the component A is preferably a linking group bonded to a benzene ring through a methylene group.

The other of $R^{22}$ and $R^{23}$ is preferably a hydrogen atom or an alkyl group having 1 to 8 carbon atoms, more preferably an alkyl group having 1 to 8 carbon atoms, and even more preferably a methyl group. If such an embodiment is adopted, a printed article is obtained in which migration of the components in the film is further reduced, and odor is further reduced.

The aryl group represented by $R^{21}$ to $R^{23}$ is preferably an aryl group having 6 to 20 carbon atoms.

Each of $R^{24}$ and $R^{25}$ is preferably independently an alkyl group having 1 to 20 carbon atoms or an aryl group having 6 to 20 carbon atoms, more preferably an alkyl group having 1 to 12 carbon atoms or an aryl group having 6 to 12 carbon atoms, even more preferably an aryl group having 6 to 12 carbon atoms, and particularly preferably an phenyl group. The alkyl group and the aryl group may be substituted. Examples of the substituent include an alkyl group, an alkoxy group, an aryl group, and a halogen atom.

The polymer structure in the component A is not particularly limited. Examples of the component A include a (meth)acryl resin, a hyperbranched polymer, a polyurethane resin, a polyester resin, a polycarbonate resin, an epoxy resin, a polyamide resin, a polyolefin resin, a styrene-(meth)acryl resin, a styrene resin, and the like having an acylphosphine oxide structure. Among these, as the component A, a (meth)acryl resin having an acylphosphine oxide structure or a hyperbranched polymer having an acylphosphine oxide structure is preferable. From the viewpoint of manufacturing suitability, a (meth)acryl resin having an acylphosphine oxide structure is particularly preferable, and from the viewpoint of inkjet ejectability, a hyperbranched polymer having an acylphosphine oxide structure is particularly preferable.

In the present invention, the (meth)acryl resin is not particularly limited as long as it is a resin obtained by homopolymerization of the (meth)acrylate compound or by at least copolymerization of a (meth)acrylate compound. However, in the (meth)acryl resin, a ratio of a monomer unit derived from a (meth)acrylate compound to all monomer units contained in the (meth)acryl resin is preferably equal to or greater than 10 mol %, more preferably equal to or greater than 50 mol %, and even more preferably equal to or greater than 80 mol %.

In the present invention, the monomer unit includes a monomer unit modified by a polymer reaction after polymerization.

The (meth)acryl resin having an acylphosphine oxide structure is preferably a (meth)acryl resin having an acylphosphine oxide structure on a side chain thereof.

A monomer that may be copolymerized with a (meth)acrylate compound is not particularly limited. However, examples of the monomer include a styrene compound, an olefin compound, a (meth)acrylamide compound, (meth)acrylic acid, (meth)acrylonitrile, a crotonic acid ester compound, a vinyl ester compound, a maleic acid diester compound, a fumaric acid diester compound, an itaconic acid diester compound, a vinyl ether compound, a vinyl ketone compound, a maleimide compound, and the like.

The (meth)acrylate compound or a monomer thereof may be a monofunctional ethylenically unsaturated compound or a polyfunctional ethylenically unsaturated compound. However, the (meth)acryl resin having an acylphosphine oxide structure is preferably a resin that mainly contains (equal to or greater than 50% by mass) a monomer unit derived from a monofunctional ethylenically unsaturated compound, and more preferably a resin solely composed of a monomer unit derived from a monofunctional ethylenically unsaturated compound.

The (meth)acryl resin having an acylphosphine oxide structure preferably has a monomer unit (constitutional unit) represented by the following Formula (A1).

(A1)

In Formula (A1), $R^a$ represents a hydrogen atom or a methyl group; $L^a$ represents a single bond or a divalent linking group; and $Ar^p$ represents the benzene ring in Formula (1) or the naphthalene ring in Formula (2).

$R^a$ is preferably a methyl group.

$L^a$ is preferably a single bond, a chain-like or cyclic alkylene group having 1 to 12 carbon atoms, a chain-like or cyclic alkenylene group having 2 to 12 carbon atoms, an arylene group having 6 to 12 carbon atoms, or a divalent group obtained by combining one or more alkylene groups, alkenylene groups, and/or arylene groups described above with one or more ester bonds, ether bonds, thioether bonds, or urethane bonds, more preferably a single bond, a chain-like or cyclic alkylene group having 1 to 12 carbon atoms, or a divalent group obtained by combining one or more alkylene groups described above with one or more ether bonds or urethane bonds, even more preferably a chain-like alkylene group having 1 to 8 carbon atoms or a divalent group obtained by combining one or more chain-like alkylene groups having 1 to 8 carbon atoms with one or more ether bonds, and particularly preferably a methylene group.

From the viewpoint of curability per amount (% by mass) of $L^a$ added to the ink composition, it is preferable for $L^a$ to have a small molecular weight. Specifically, the molecular weight of $L^a$ is preferably equal to or less than 290, more preferably equal to or less than 170, and even more preferably equal to or less than 80. Furthermore, the molecular weight of $L^a$ is preferably equal to or greater than 14.

$Ar^p$ shows that the monomer unit is bonded to the acylphosphine oxide structure, in the binding position of the linking group in Formula (1) or Formula (2) that is linked to a main chain or a core of the component A.

The monomer unit represented by Formula (A1) is more preferably a monomer unit represented by the following Formulae (A2) to (A4).

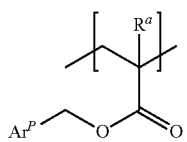

(A2)

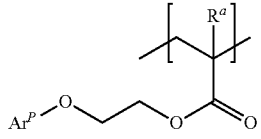

(A3)

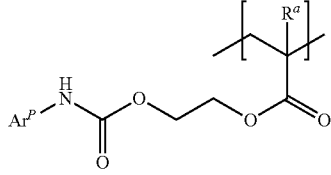

(A4)

In Formulae (A2) to (A4), $R^a$ represents a hydrogen atom or a methyl group; $Ar^p$ represents the benzene ring in Formula (1) or the naphthalene ring in Formula (2).

The (meth)acryl resin having an acylphosphine oxide structure particularly preferably has a monomer unit represented by the following Formula (A5).

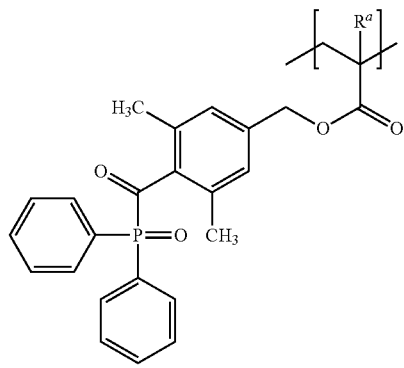

(A5)

In Formula (A5), $R^a$ represents a hydrogen atom or a methyl group.

From the viewpoint of curability and storage stability, the (meth)acryl resin having an acylphosphine oxide structure preferably has a monomer unit having a (poly)ether structure.

The monomer unit having a (poly)ether structure is preferably a monomer unit represented by the following Formula (A6).

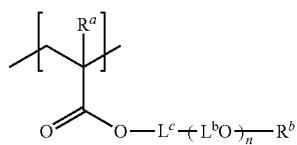

(A6)

In the formula, $R^a$ represents a hydrogen atom or a methyl group; $L^b$ represents an ethylene group or a propylene group; $L^c$ represents a single bond or a divalent linking group; $R^b$ represents a hydrogen atom, an alkyl group having 1 to 12 carbon atoms, or a phenyl group; and n represents 1 to 50.

From the viewpoint of uniformity of a polymerization rate of the respective monomers at the time of polymerization, $R^a$ in Formula (A6) is preferably a methyl group.

$R^b$ is preferably an alkyl group having 1 to 8 carbon atoms or a phenyl group, more preferably an alkyl group having 1 to 4 carbon atoms, and even more preferably a methyl group. Furthermore, the alkyl group represented by $R^b$ may be linear or branched.

$L^b$ is preferably $-CH_2CH_2-$, $-CH_2CH(CH_3)-$, or $-CH(CH_3)CH_2-$, and particularly preferably an ethylene group ($-CH_2CH_2-$).

$L^c$ is preferably a single bond or a divalent linking group having 1 to 50 carbon atoms, more preferably a single bond or an alkylene group having 1 to 20 carbon atoms, and even more preferably a single bond.

n in Formula (A6) is preferably 1 to 20, more preferably 2 to 10, and even more preferably 2 to 5.

The content of the monomer unit having a (poly)ether structure in the (meth)acryl resin having an acylphosphine oxide structure is preferably 1 mol % to 50 mol %, more preferably 2 mol % to 40 mol %, and even more preferably 5 mol % to 25 mol %, with respect to all monomer units contained in the (meth)acryl resin having an acylphosphine oxide structure.

The hyperbranched polymer having an acylphosphine oxide structure is preferably a hyperbranched polymer having an acylphosphine oxide structure on a terminal thereof.

The number of the acylphosphine oxide structure in the hyperbranched polymer having an acylphosphine oxide structure is preferably 1 to 20, more preferably 3 to 10, and even more preferably 3 to 8.

The hyperbranched polymer may be a polymer having at least one or more branches, and examples thereof include a dendrimer, a hyperbranched polymer, a dendritic polymer, a star polymer, and the like.

The molecular weight (weight-average molecular weight) of the hyperbranched polymer having an acylphosphine oxide structure is preferably equal to or greater than 1,000 and equal to or less than 5,000, and more preferably equal to or greater than 1,000 and equal to or less than 3,000.

The hyperbranched polymer having an acylphosphine oxide structure preferably has, for example, the following structure as a core, but the hyperbranched polymer is not limited to the structure.

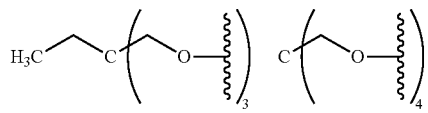

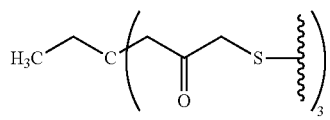

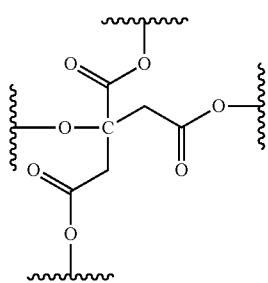

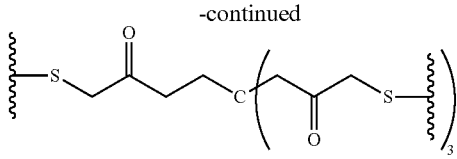

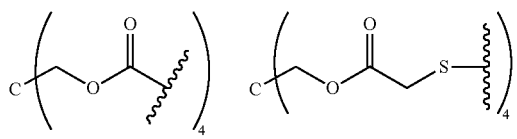

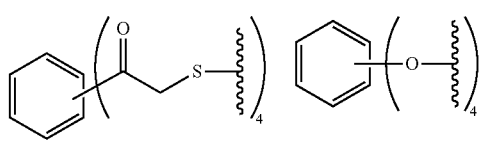

In the formulae, the portion indicated by a wavy line represents a binding position in which the structure is bonded to another structure.

When the hyperbranched polymer having an acylphosphine oxide structure has a structure represented by Formula (1) and/or Formula (2), a portion other than the structure represented by Formula (1) and/or Formula (2) in the hyperbranched polymer and the linking group linked to a main chain or a core of the component A are preferably aliphatic structures, and more preferably p-valent aliphatic hydrocarbon groups (p represents an integer of equal to or greater than 3) or a group obtained by combining one or more q-valent aliphatic hydrocarbon groups (q represents an integer of equal to or greater than 1) with one or more ether bonds, thioether bonds, ester bonds, urethane bonds, and/or carbonyl groups.

The hyperbranched polymer having an acylphosphine oxide structure preferably has at least a sulfur atom, and more preferably has at least a thioether bond.

Specific examples of the component A will be shown below, but the component A is not limited thereto. Herein, the number on the right lower side in the parenthesis in each of the constitutional units represents a molar ratio. Furthermore, Ph represents a phenyl group, t-Bu represents a t-butyl group, and i-Pr represents an isopropyl group.

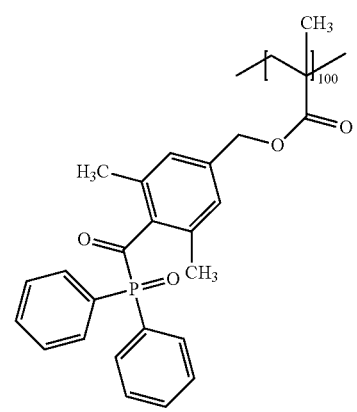

A - 1 (Mw = 1,100)
A - 2 (Mw = 8,000)
A - 3 (Mw = 32,000)

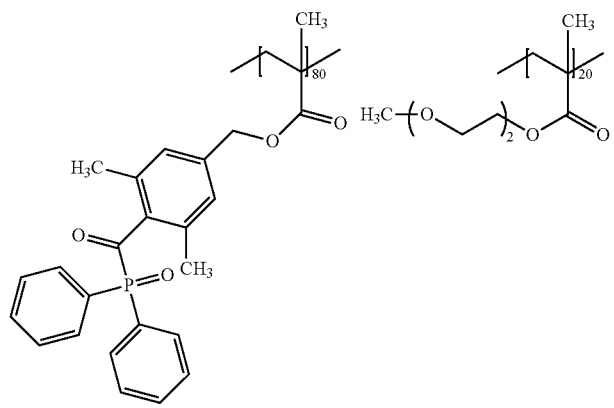

A - 4 (Mw = 1,500)

-continued
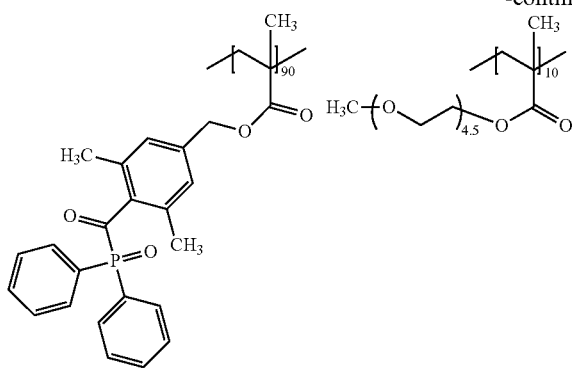
A - 5 (Mw = 1,500)
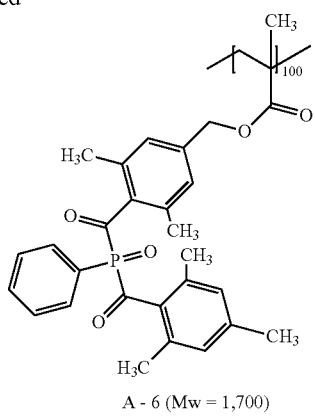
A - 6 (Mw = 1,700)
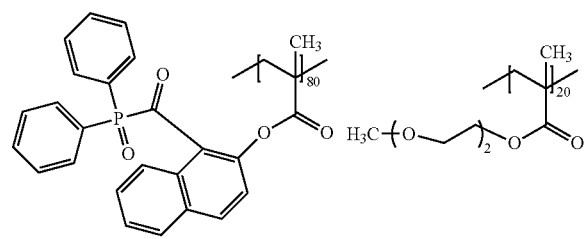
A - 7 (Mw = 1,500)
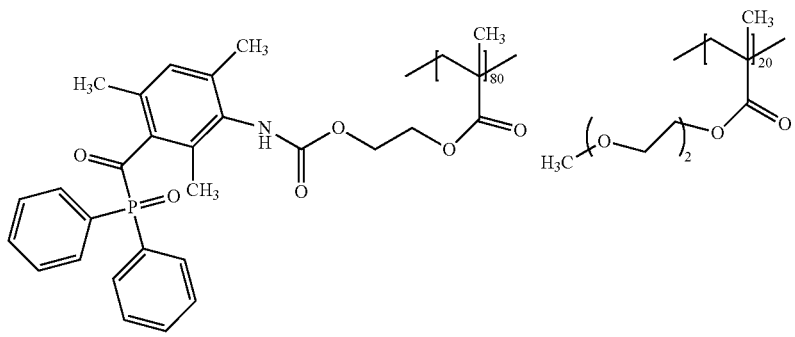
A - 8 (Mw = 1,500)
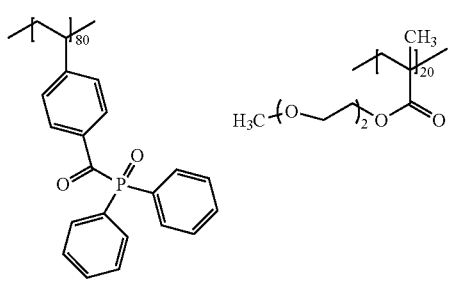
A - 9 (Mw = 2,000)
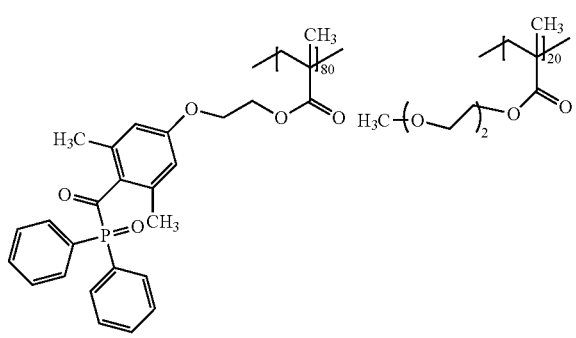
A - 10 (Mw = 1,500)
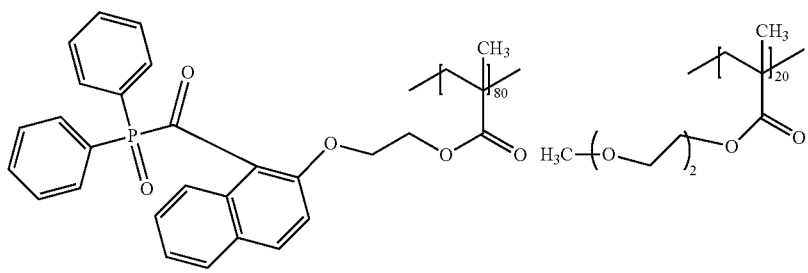
A - 11 (Mw = 1,700)

-continued
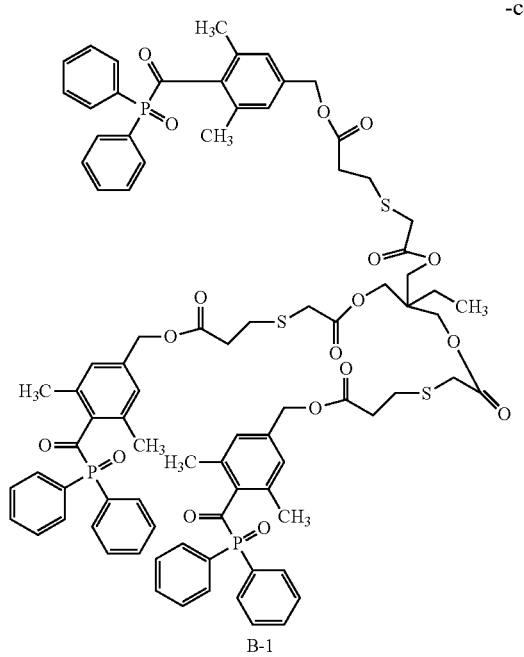
B-1
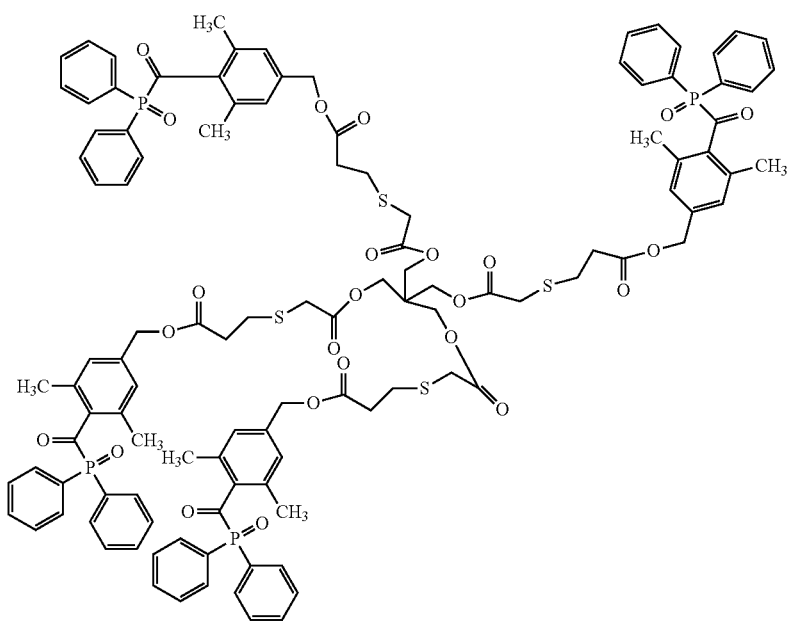
B-2

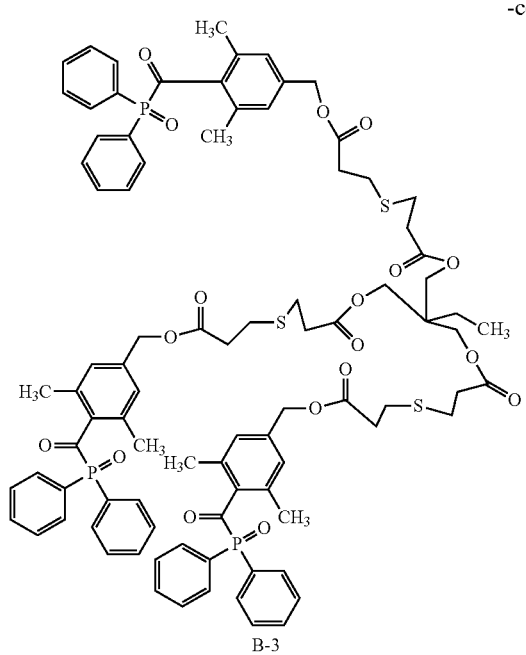
B-3
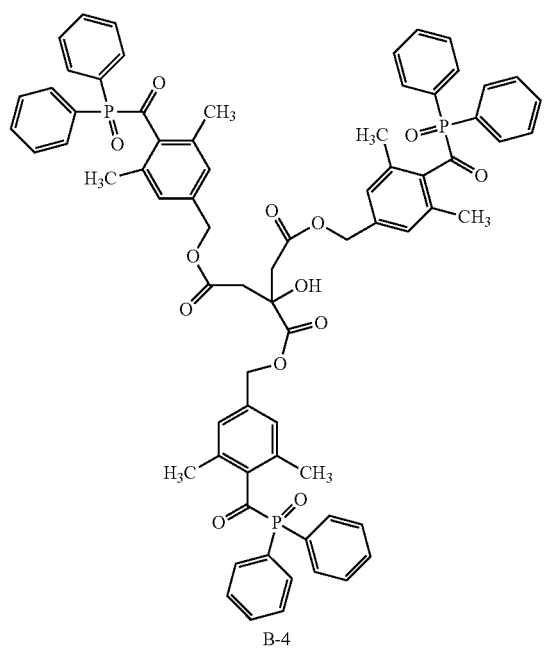
B-4

-continued
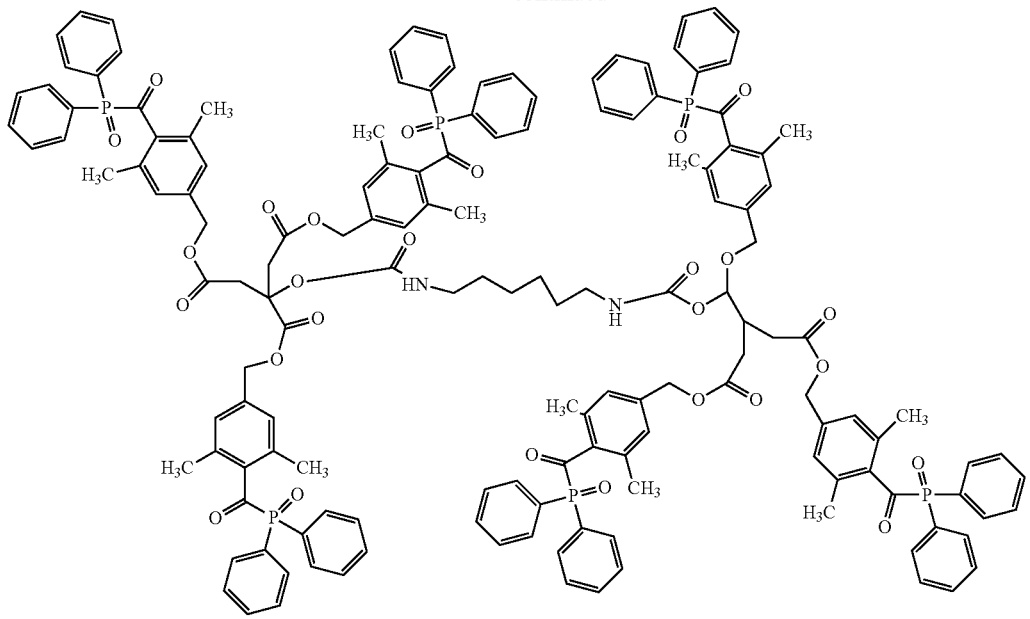
B-5
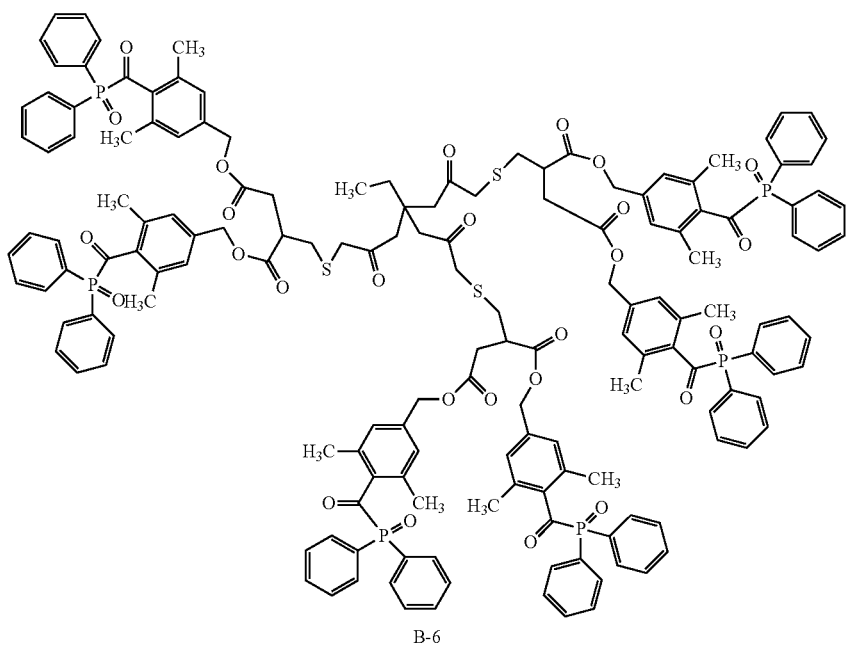
B-6
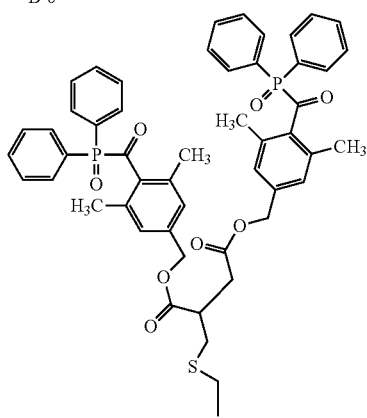

-continued
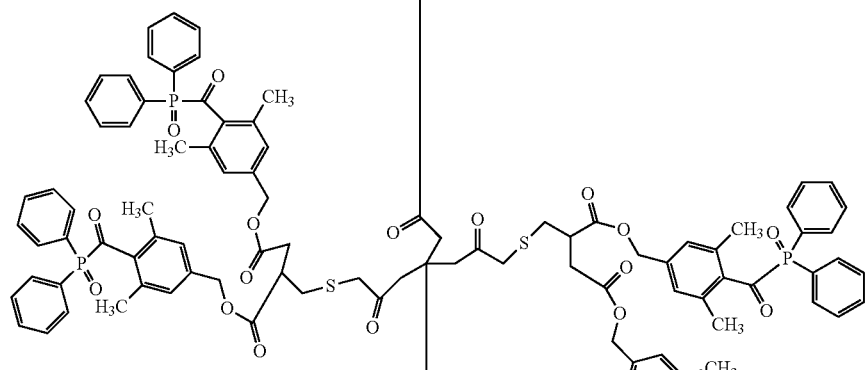
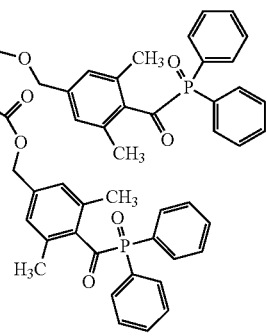
B-7
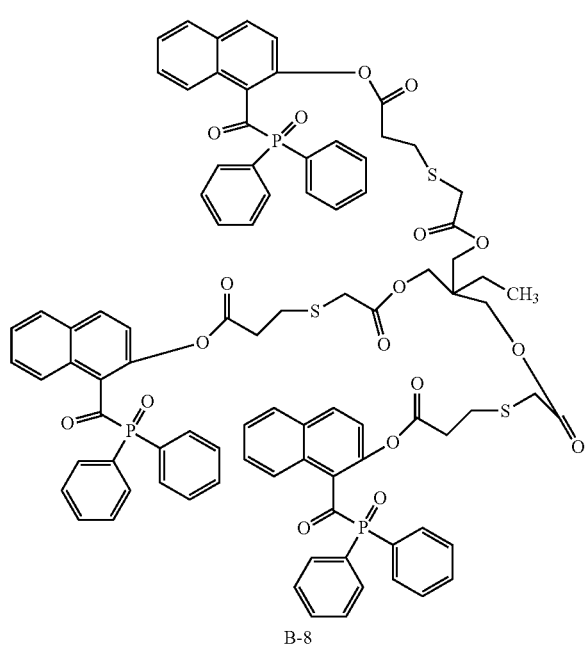
B-8

-continued
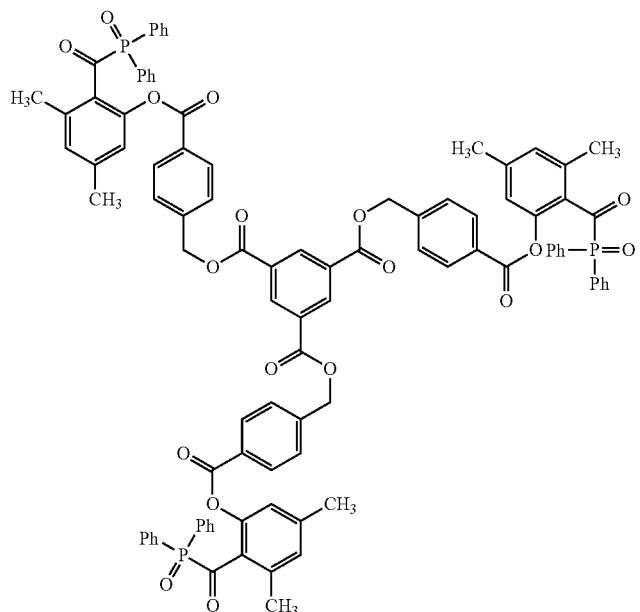
B-9
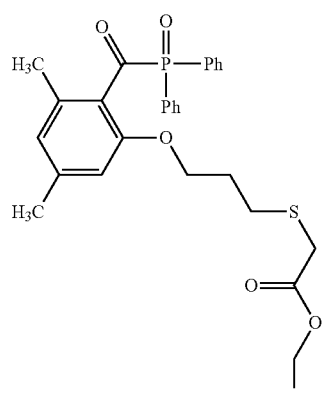
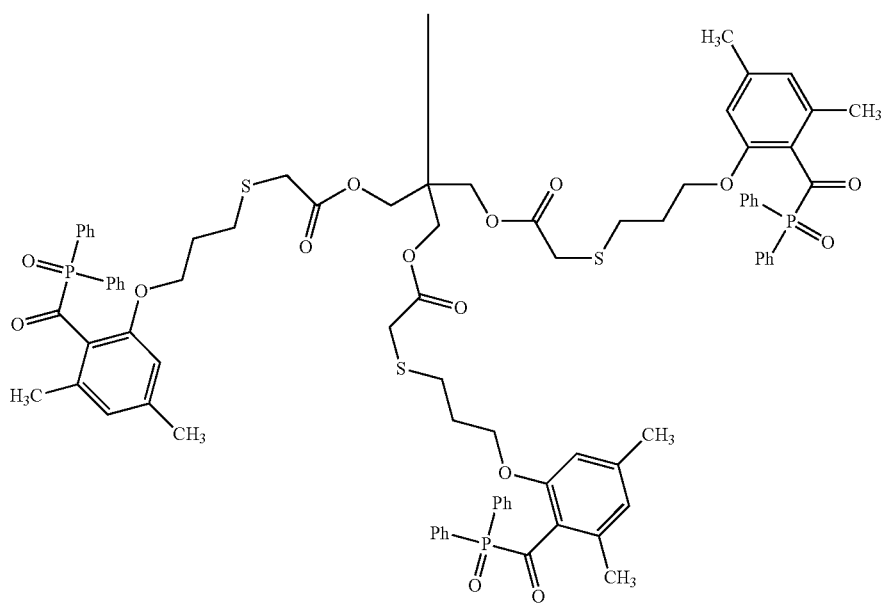
B-10

-continued
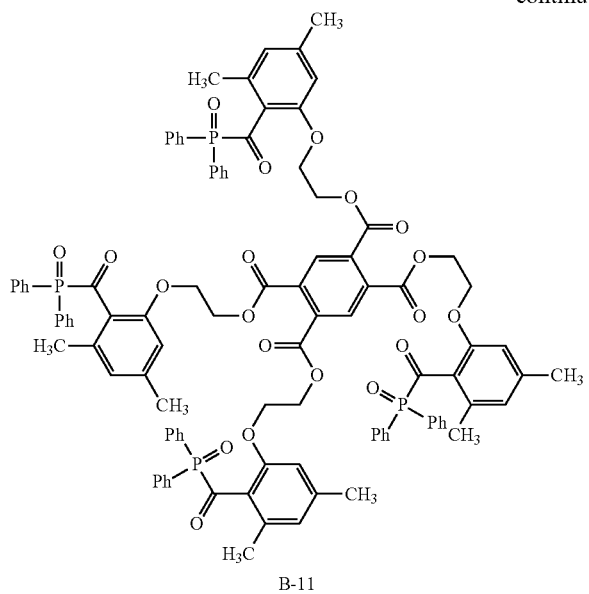
B-11
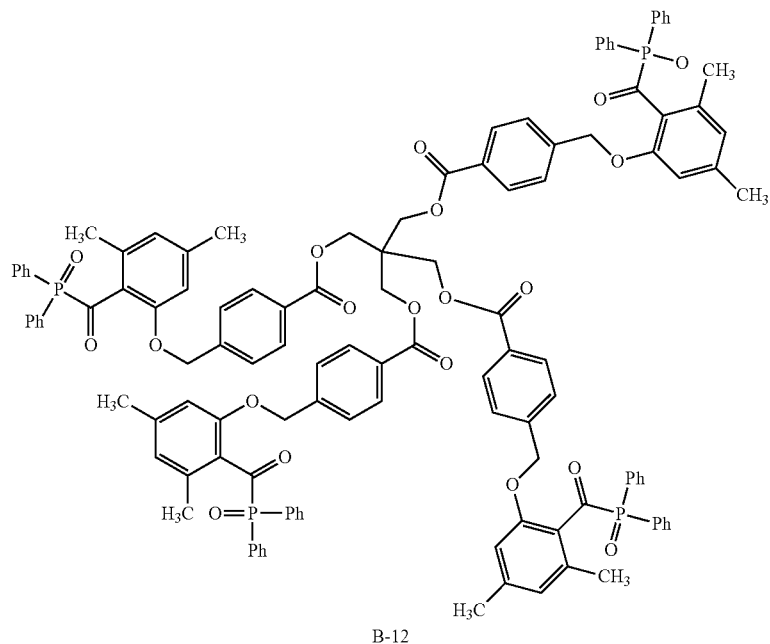
B-12
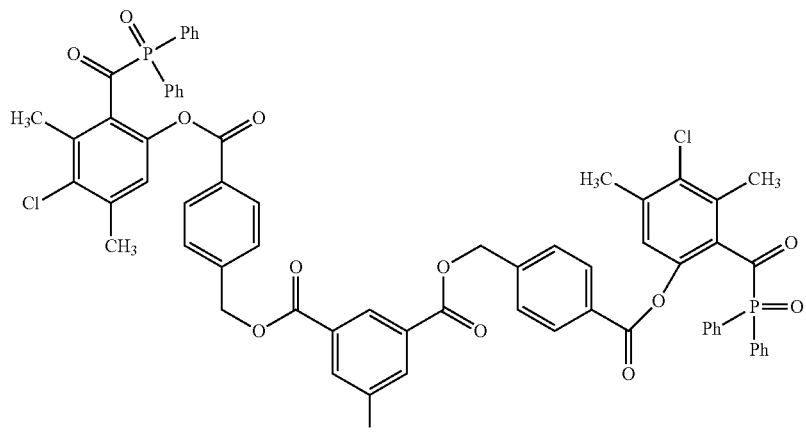

-continued
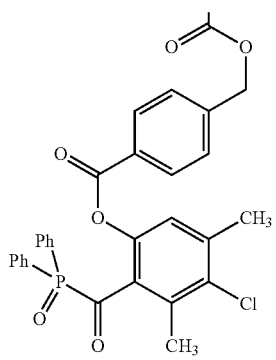
B-13
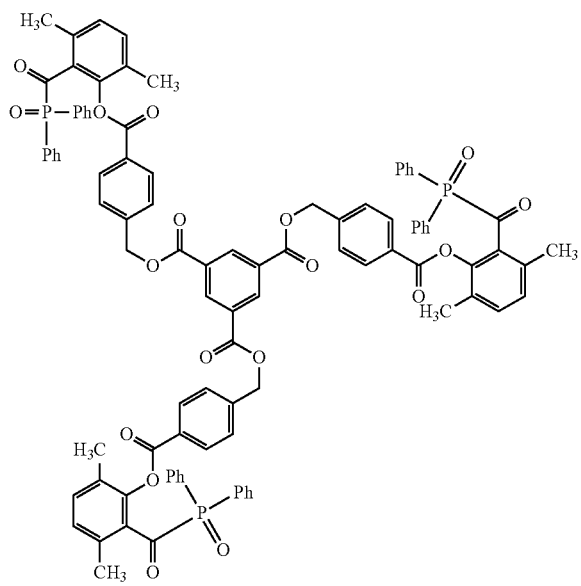
B-14
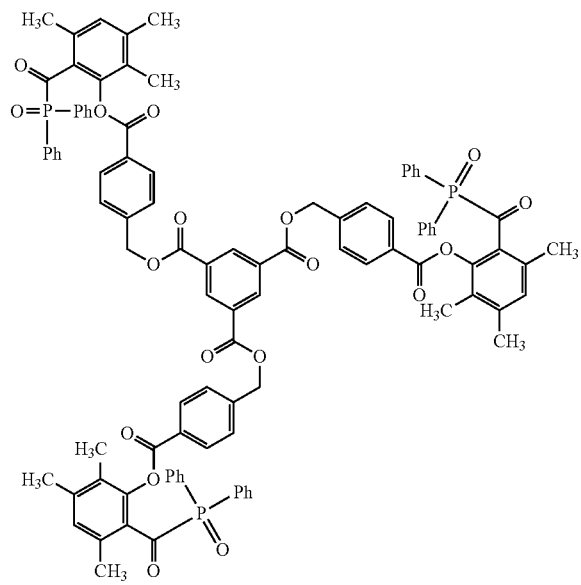
B-15

-continued
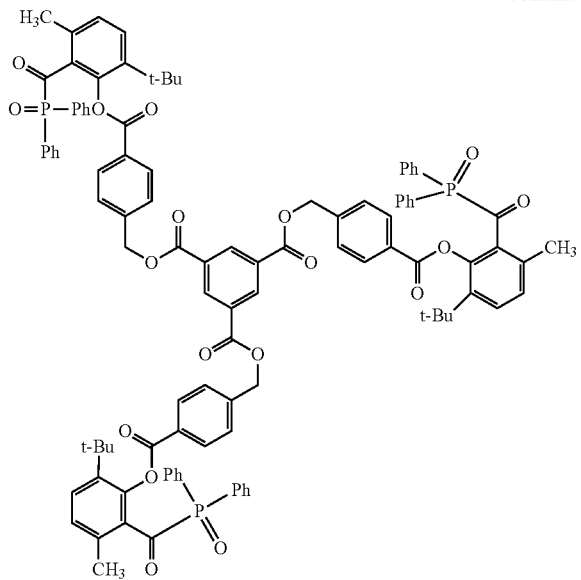
B-16
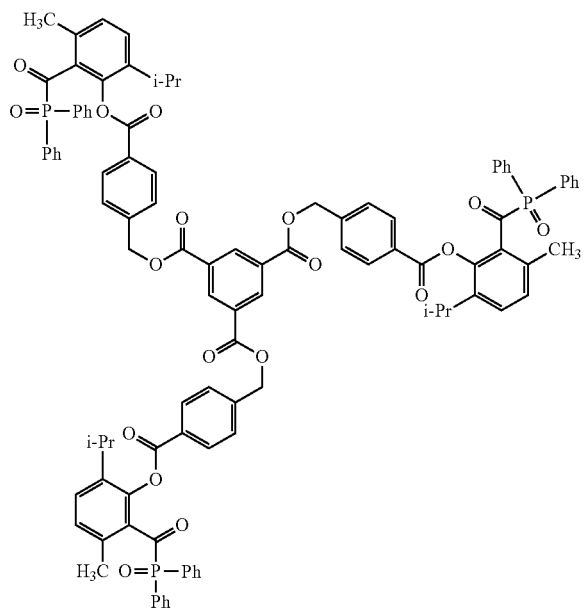
B-17

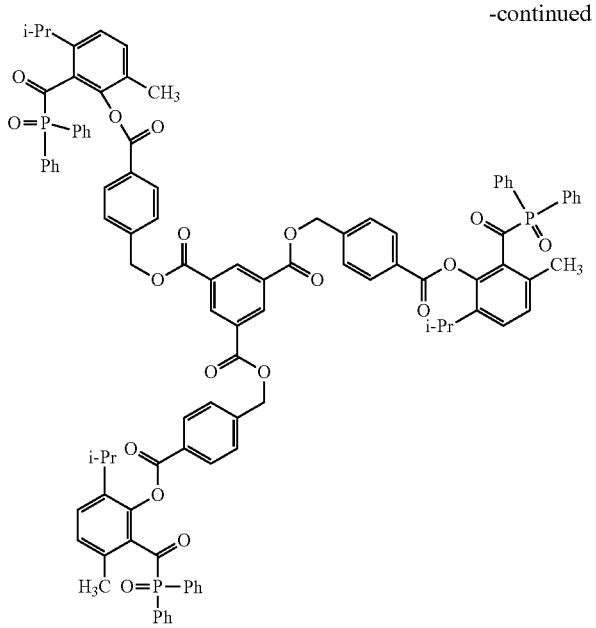

B-18

The content of the component A in the ink composition of the present invention is not particularly limited. However, the content of the component A is preferably 0.1% by mass to 20% by mass, more preferably 1% by mass to 15% by mass, even more preferably 3% by mass to 10% by mass, and particularly preferably 4% by mass to 8% by mass, with respect to the total amount of the ink composition. If the content is within the above range, curability becomes excellent, and it is possible to further reduce the amount of the low-molecular-weight compound eluted from the obtained image and to further reduce the odor generated from the obtained image.

(Component B) Polymerizable Compound

The ink composition of the present invention contains a polymerizable compound (also simply referred to as a "monomer" or a "polymerizable monomer").

The polymerizable compound is not particularly limited as long as it is a compound that can be cured by causing a polymerization reaction by being supplied with a certain energy. As the polymerizable compound, any compound in the form of a monomer, an oligomer, or a polymer can be used. Particularly, various known polymerizable monomers are preferable which are known as radically polymerizable monomers that cause a polymerization reaction by using an initiating species generated from a polymerization initiator added as desired.

For the purpose of adjusting a reaction rate, properties of the cured film, properties of the ink composition, and the like, one kind of the polymerizable compound or a plurality of the polymerizable compounds can be used. Furthermore, the polymerizable compound may be a monofunctional compound or a polyfunctional compound. If the ratio of the monofunctional polymerizable compound is great, the cured material tends to more easily become soft, and if the ratio of the polyfunctional polymerizable compound is great, the curability tends to become excellent. Accordingly, the ratio between the monofunctional polymerizable compound and the polyfunctional polymerizable compound is arbitrarily determined according to the purpose.

As the polymerizable compound, it is also possible to use various known radically polymerizable monomers that cause a polymerization reaction by using an initiating species generated from a photo-radical initiator.

Examples of the radically polymerizable monomers include (meth)acrylates, (meth)acrylamides, aromatic vinyls, and the like. In the present specification, "(meth)acrylate" refers to either or both of "acrylate" and "methacrylate" in some cases, and "(meth)acryl" refers to either or both of "acryl" and "methacryl" in some cases.

Examples of (meth)acrylates used as the radically polymerizable monomers include monofunctional (meth)acrylate, bifunctional (meth)acrylate, trifunctional (meth)acrylate, tetrafunctional (meth)acrylate, pentafunctional (meth)acrylate, hexafunctional (meth)acrylate, and the like.

Examples of the monofunctional (meth)acrylate include hexyl (meth)acrylate, 2-ethylhexyl (meth)acrylate, tert-octyl (meth)acrylate, isoamyl (meth)acrylate, decyl (meth)acrylate, isodecyl (meth)acrylate, stearyl (meth)acrylate, isostearyl (meth)acrylate, cyclohexyl (meth)acrylate, 4-n-butylcyclohexyl (meth)acrylate, bornyl (meth)acrylate, isobornyl (meth)acrylate, benzyl (meth)acrylate, 2-ethylhexyldiglycol (meth)acrylate, butoxyethyl (meth)acrylate, 2-chloroethyl (meth)acrylate, 4-bromobutyl (meth)acrylate, cyanoethyl (meth)acrylate, butoxymethyl (meth)acrylate, 3-methoxybutyl (meth)acrylate, 2-(2-methoxyethoxy)(meth)acrylate, 2-(2-butoxyethoxy)ethyl (meth)acrylate, 2,2,2-tetrafluoroethyl (meth)acrylate, 1H,1H,2H,2H-perfluorodecyl (meth)acrylate, 4-butylphenyl (meth)acrylate, phenyl (meth)acrylate, 2,4,5-tetramethylphenyl (meth)acrylate, 4-chlorophenyl (meth)acrylate, phenoxymethyl (meth)acrylate, phenoxyethyl (meth)acrylate, glycidyl (meth)acrylate, glycidyloxybutyl (meth)acrylate, glycidyloxyethyl (meth)acrylate, glycidyloxypropyl (meth)acrylate, tetrahydrofurfuryl (meth)acrylate, 2-hydroxyethyl (meth)acrylate, 3-hydroxypropyl (meth)acrylate, 2-hydroxypropyl (meth)acrylate, 2-hydroxybutyl (meth)acrylate, 4-hydroxybutyl (meth)acrylate, 3-hydroxybutyl (meth)acrylate, dimethylaminoethyl (meth)acrylate, diethylaminoethyl (meth)acrylate, dimethylaminopropyl (meth)acrylate, diethylaminopropyl (meth)acrylate, trimethoxysilylpropyl (meth)acrylate, trimethylsilylpropyl (meth)acrylate, polyethylene oxide monomethyl ether (meth)acrylate, oligoethylene oxide monomethyl ether (meth)acrylate, polyethylene oxide (meth)acrylate, oligoethylene oxide (meth)acrylate, oligoethylene oxide monoalkyl ether (meth)acrylate, polyethylene oxide monoalkyl ether (meth)acrylate, dipropylene glycol (meth)acrylate, polypropylene oxide monoalkyl ether (meth)acrylate, oligopropylene oxide monoalkyl ether (meth)acrylate, 2-methacryloyloxyethyl succinate, 2-methacryloyloxyhexahydrophthalic acid, 2-methacryloyloxyethyl-2-hydroxypropyl phthalate, butoxydiethylene glycol (meth)acrylate, trifluoroethyl (meth)acrylate, perfluorooctylethyl (meth)acrylate, 2-hydroxy-3-phenoxypropyl (meth)acrylate, ethylene oxide (EO)-modified phenol (meth)acrylate, EO-modified cresol (meth)acrylate, EO-modified nonylphenyl (meth)acrylate, propylene oxide (PO)-modified nonylphenyl (meth)acrylate, EO-modified 2-ethylhexyl (meth)acrylate, dicyclopentenyl (meth)acrylate, dicyclopentenyloxyethyl (meth)acrylate, dicyclopentanyl (meth)acrylate, (3-ethyl-3-oxetanylmethyl) (meth)acrylate, and phenoxyethylene glycol (meth)acrylate.

Examples of the bifunctional (meth)acrylate include 1,6-hexanediol di(meth)acrylate, 1,10-decanediol di(meth)acrylate, neopentyl glycol di(meth)acrylate, 2,4-dimethyl-1,5-pentanediol di(meth)acrylate, butylethyl propanediol (meth)acrylate, ethoxylated cyclohexane methanol di(meth)acrylate, polyethylene glycol di(meth)acrylate, oligoethylene glycol di(meth)acrylate, ethylene glycol di(meth)acrylate, 2-ethyl-2-butyl butanediol di(meth)acrylate, hydroxypivalic acid neopentyl glycol di(meth)acrylate, EO-modified bisphenol A di(meth)acrylate, bisphenol F polyethoxy di(meth)acrylate, polypropylene glycol di(meth) acrylate, oligopropylene glycol di(meth)acrylate, 1,4-butanediol di(meth)acrylate, 2-ethyl-2-butyl propanediol di(meth)acrylate, 1,9-nonane di(meth)acrylate, propoxylated-ethoxylated bisphenol A di(meth)acrylate, tricyclodecane di(meth)acrylate, dipropylene glycol di(meth)acrylate, tripropylene glycol di(meth)acrylate, PO-modified neopentyl glycol di(meth)acrylate, and the like.

Examples of the trifunctional (meth)acrylate include trimethylolpropane tri(meth)acrylate, trimethylolethane tri (meth)acrylate, an alkylene oxide-modified tri(meth)acrylate of trimethylolpropane, pentaerythritol tri(meth)acrylate, dipentaerythritol tri(meth)acrylate, trimethylolpropane tri ((meth)acryloyloxypropyl)ether, an isocyanuric acid alkylene oxide-modified tri(meth)acrylate, propionic acid dipentaerythritol tri(meth)acrylate, tri((meth)aryloyloxyethyl) isocyanurate, hydroxypivaldehyde-modified dimethylolpropane tri(meth)acrylate, sorbitol tri(meth)acrylate, propoxylated trimethylolpropane tri(meth)acrylate, ethoxylated glycerin triacrylate, and the like.

Examples of the tetrafunctional (meth)acrylate include pentaerythritol tetra(meth)acrylate, sorbitol tetra(meth)acrylate, di-trimethylolpropane tetra(meth)acrylate, propionic acid dipentaerythritol tetra(meth)acrylate, ethoxylated pentaerythritol tetra(meth)acrylate, and the like.

Examples of the pentafunctional (meth)acrylate include sorbitol penta(meth)acrylate and dipentaerythritol penta(meth)acrylate.

Examples of the hexafunctional (meth)acrylate include dipentaerythritol hexa(meth)acrylate, sorbitol hexa(meth) acrylate, an alkylene oxide-modified hexa(meth)acrylate of phosphazene, s-caprolactone-modified dipentaerythritol hexa(meth)acrylate, and the like.

Examples of the (meth)acrylamides used as the radically polymerizable monomers include (meth)acrylamide, N-methyl (meth)acrylamide, N-ethyl (meth)acrylamide, N-propyl (meth)acrylamide, N-n-butyl (meth)acrylamide, N-t-butyl (meth)acrylamide, N-butoxymethyl (meth)acrylamide, N-isopropyl (meth)acrylamide, N-methylol (meth) acrylamide, N,N-dimethyl (meth)acrylamide, N,N-diethyl (meth)acrylamide, and (meth)acryloyl morpholine.

Examples of the aromatic vinyls used as the radically polymerizable monomers include styrene, dimethyl styrene, trimethyl styrene, isopropyl styrene, chloromethyl styrene, methoxystyrene, acetoxystyrene, chlorostyrene, dichlorostyrene, bromostyrene, vinyl benzoic acid methyl ester, 3-methyl styrene, 4-methyl styrene, 3-ethyl styrene, 4-ethyl styrene, 3-propyl styrene, 4-propyl styrene, 3-butyl styrene, 4-butyl styrene, 3-hexyl styrene, 4-hexyl styrene, 3-octyl styrene, 4-octyl styrene, 3-(2-ethylhexyl)styrene, 4-(2-ethylhexyl)styrene, allyl styrene, isopropenyl styrene, butenyl styrene, octenyl styrene, 4-t-butoxycarbonyl styrene, 4-t-butoxystyrene, and the like.

Examples of the radically polymerizable monomers used in the present invention include vinyl esters (such as vinyl acetate, vinyl propionate, and vinyl versatate), allyl esters (such as allyl acetate), halogen-containing monomers (such as vinylindene chloride and vinyl chloride), vinyl ethers (such as methyl vinyl ether, butyl vinyl ether, hexyl vinyl ether, methoxyvinyl ether, 2-ethylhexyl vinyl ether, methoxyethyl vinyl ether, cyclohexyl vinyl ether, chloroethyl vinyl ether, and triethylene glycol divinyl ether), vinyl cyanides (such as (meth)acrylonitrile), olefins (such as ethylene and propylene), N-vinyl lactams (such as N-vinyl caprolactam), and the like.

More specifically, it is possible to use commercially available products or radically polymerizable or crosslinkable monomers, oligomers, and polymers known in the related art that are described in "Handbook of Crosslinking Agent" (Shinzo Yamashita, 1981, TAISEISHA, LTD.); "Handbook of UVEB Curing (Raw Materials)" (Kiyomi Kato, 1985, Kobunshi Kankokai); "Application and Market of UVEB Curing Technology" (RadTech Japan, 1989, CMC Publishing CO., LTD., p. 79); "Handbook of Polyester Resin" (Eiichiro Takiyama, 1988, NIKKAN KOGYO SHIMBUN, LTD.); and the like.

The component B preferably contains at least a polyfunctional ethylenically unsaturated compound, more preferably contains at least a bifunctional ethylenically unsaturated compound and a trifunctional ethylenically unsaturated compound, even more preferably contains at least tripropylene glycol diacrylate and EO-modified trimethylolpropane triacrylate, and particularly preferably contains at least tripropylene glycol diacrylate, EO-modified trimethylolpropane triacrylate, and PO-modified neopentyl glycol diacrylate. If such an embodiment is adopted, curability becomes better, and the migration and odor of the cured film can be further suppressed.

From the viewpoint of curability, the content of the polymerizable compound in the ink composition of the present invention is preferably 50% by mass to 95% by mass, and more preferably 55% by mass to 92% by mass, with respect to the total mass of the ink composition.

In the polymerizable compound contained in the ink composition of the present invention, the ratio of the polyfunctional polymerizable compound to the total amount of the polymerizable compound is preferably equal to or greater than 80% by mass, more preferably equal to or greater than 90% by mass, and even more preferably equal to or greater than 95% by mass. If such an embodiment is adopted, curability becomes better, and the migration and odor of the cured film can be further suppressed.

(Component C) Colorant

The ink composition of the present invention contains a colorant.

The colorant is not particularly limited. However, as the colorant, a pigment and an oil-soluble dye having excellent weather resistance and color reproducibility are preferable. The colorant can be used by being arbitrarily selected from among known colorants such as soluble dyes. As the colorant, it is preferable to select a compound that does not function as a polymerization inhibitor, because such a compound does not reduce sensitivity of a curing reaction caused by an active energy ray.

A pigment functions as the colorant of the ink composition. In the present invention, the aforementioned pigment, which has a very small particle size as described later, is uniformly and stably dispersed in the ink composition. Consequently, the ink composition of the present invention has excellent color developability and can form a clear image having excellent weather resistance.

The pigment is not particularly limited and can be appropriately selected according to the purpose. Examples of the pigment include known organic and inorganic pigments, resin particles dyed with a dye, commercially available pigment dispersions, and pigments having undergone surface treatment (for example, pigments dispersed in an insoluble resin or the like used as a dispersion medium or pigments having a resin-grafted surface). Examples of the pigment also include those described in "Dictionary of Pigments" (Seichiro Ito, 2000), "Industrial Organic Pigments" (W. Herbst, K. Hunger), JP2002-12607A, JP2002-188025A, JP2003-26978A, JP2003-342503A, and the like.

Examples of the organic and inorganic pigments include a yellow pigment, a magenta pigment, blue pigment, a cyan pigment, a green pigment, an orange pigment, a brown pigment, a violet pigment, a black pigment, a white pigment, and the like.

The yellow pigment is a pigment having yellow color, and examples thereof include monoazo pigments such as C. I. Pigment Yellow 1 (first yellow G or the like) and C. I. Pigment Yellow 74; disazo pigments such as C. I. Pigment Yellow 12 (disazo yellow or the like), C. I. Pigment Yellow 17, C. I. Pigment Yellow 97, C. I. Pigment Yellow 3, C. I. Pigment Yellow 16, C. I. Pigment Yellow 83, C. I. Pigment Yellow 155, and C. I. Pigment Yellow 219; non-benzidine-based azo pigments such as C. I. Pigment Yellow 180; azo lake pigments such as C. I. Pigment Yellow 100 (tartrazine yellow lake or the like); condensed azo pigments such as C. I. Pigment Yellow 95 (condensed azo yellow or the like), C. I. Pigment Yellow 93, C. I. Pigment Yellow 94, C. I. Pigment Yellow 128, and C. I. Pigment Yellow 166; acidic dye lake pigments such as C. I. Pigment Yellow 115 (quinoline yellow lake or the like); basic dye lake pigments such as C. I. Pigment Yellow 18 (thioflavin lake or the like); anthraquinone pigments such as C. I. Pigment Yellow 24 (flavanthrone yellow or the like); quinophthalone pigments such as C. I. Pigment Yellow 110 (quinophtalone yellow or the like); isoindoline pigments such as C. I. Pigment Yellow 139 (isoindoline yellow or the like); pyrazolone pigments such as C. I. Pigment Yellow 60 (pyrazolone yellow or the like); acetron pigments such as C. I. Pigment Yellow 120, C. I. Pigment Yellow 154, C. I. Pigment Yellow 167, C. I. Pigment Yellow 151, C. I. Pigment Yellow 175, C. I. Pigment Yellow 180, C. I. Pigment Yellow 181, and C. I. Pigment Yellow 194; metal complex salt pigments such as C. I. Pigment Yellow 150; nitroso pigments such as C. I. Pigment Yellow 153 (nickel nitroso yellow or the like), metal complex salt azomethine pigments such as C. I. Pigment Yellow 117 (copper azomethine yellow or the like), C. I. Pigment Yellow, and the like.

The magenta pigment is a pigment having red or magenta color, and examples thereof include monoazo-based pigments such as C. I. Pigment Red 3 (toluidine red or the like); B-naphthol pigments such as C. I. Pigment Red 1, C. I. Pigment Red 4, and C. I. Pigment Red 6; disazo pigments such as C. I. Pigment Red 38 (pyrazolone red B or the like); azo lake pigments such as C. I. Pigment Red 53:1 (lake red C or the like), C. I. Pigment Red 57:1 (brilliant carmine 6B or the like), C. I. Pigment Red 52:1, and C. I. Pigment Red 48 (B-oxynaphthoic acid lake or the like); condensed azo pigments such as C. I. Pigment Red 144, C. I. Pigment Red 166, C. I. Pigment Red 220, C. I. Pigment Red 214, C. I. Pigment Red 221, and C. I. Pigment Red 242 (condensed azo lake or the like); acidic dye lake pigments such as C. I. Pigment Red 174 (phloxine B lake or the like) and C. I. Pigment Red 172 (erythrosine lake or the like); basic dye lake pigments such as C. I. Pigment Red 81 (rhodamine 6G' lake or the like); anthraquinone-based pigments such as C. I. Pigment Red 177 (dianthraquinonyl red or the like); thioindigo pigments such as C. I. Pigment Red 88 (thioindigo bordeaux or the like); perinone pigments such as C. I. Pigment Red 194 (perinone red or the like); perylene pigments such as C. I. Pigment Red 149, C. I. Pigment Red 179, C. I. Pigment Red 178, C. I. Pigment Red 190, C. I. Pigment Red 224, and C. I. Pigment Red 123; quinacridone pigments such as C. I. Pigment Violet 19 (unsubstituted quinacridone), C. I. Pigment Red 122, C. I. Pigment Red 262, C. I. Pigment Red 207, and C. I. Pigment Red 209; isoindolinone pigments such as C. I. Pigment Red 180 (isoindolinone red 2BLT or the like); alizarin lake pigments such as C. I. Pigment Red 83 (madder lake or the like); naphtholone pigments such as C. I. Pigment Red 171, C. I. Pigment Red 175, C. I. Pigment Red 176, C. I. Pigment Red 185, and C. I. Pigment Red 208; naphthol AS-based lake pigments such as C. I. Pigment Red 247; naphthol AS pigments such as C. I. Pigment Red 2, C. I. Pigment Red 5, C. I. Pigment Red 21, C. I. Pigment Red 170, C. I. Pigment Red 187, C. I. Pigment Red 256, C. I. Pigment Red 268, and C. I. Pigment Red 269; diketopyrrolopyrrole pigments such as C. I. Pigment Red 254, C. I. Pigment Red 255, C. I. Pigment Red 264, and C. I. Pigment Red 272; and the like.

The cyano pigment is a pigment having blue or cyan color, and examples thereof include disazo-based pigments such as C. I. Pigment Blue 25 (dianisidine blue or the like); phthalocyanine pigments such as C. I. Pigment Blue 15, C. I. Pigment Blue 15:1, C. I. Pigment Blue 15:2, C. I. Pigment Blue 15:3, C. I. Pigment Blue 15:4, C. I. Pigment Blue 15:6, and C. I. Pigment Blue 16 (phthalocyanine blue or the like); acidic dye lake pigments such as C. I. Pigment Blue 24 (peacock blue lake or the like); basic dye lake pigments such as C. I. Pigment Blue 1 (Victoria pure blue BO lake or the like); anthraquinone-based pigments such as C. I. Pigment Blue 60 (indanthrone blue or the like); alkali blue pigments such as C. I. Pigment Blue 18 (alkali blue V-5:1); and the like.

The green pigment is a pigment having green color, and examples thereof include phthalocyanine pigments such as C. I. Pigment Green 7 (phthalocyanine green) and C. I. Pigment Green 36 (phthalocyanine green); azo metal complex pigments such as C. I. Pigment Green 8 and C. I. Pigment Green 10; and the like.

The orange pigment is a pigment having orange color, and examples thereof include isoindoline-based pigments such as C. I. Pigment Orange 66 (isoindoline orange); anthraquinone-based pigments such as C. I. Pigment Orange 51 (dichloropyranthrone orange); B-naphthol pigments such as C. I. Pigment Orange 2, C. I. Pigment Orange 3, and C. I. Pigment Orange 5; naphthol AS pigments such as C. I. Pigment Orange 4, C. I. Pigment Orange 22, C. I. Pigment Orange 24, C. I. Pigment Orange 38, and C. I. Pigment Orange 74; isoindolinone pigments such as C. I. Pigment Orange 61; perinone pigments such as C. I. Pigment Orange 43; disazo pigments such as C. I. Pigment Orange 15 and C. I. Pigment Orange 16; quinacridone pigments such as C. I. Pigment Orange 48 and C. I. Pigment Orange 49; acetron pigments such as C. I. Pigment Orange 36, C. I. Pigment Orange 62, C. I. Pigment Orange 60, C. I. Pigment Orange 64, and C. I. Pigment Orange 72; pyrazolone pigments such as C. I. Pigment Orange 13 and C. I. Pigment Orange 34; and the like.

The brown pigment is a pigment having brown color, and examples thereof include naphthalone pigments such as C. I. Pigment Brown 25 and C. I. Pigment Brown 32; and the like.

The violet pigment is a pigment having violet color, and examples thereof include naphtholone pigments such as C. I. Pigment Violet 32; perylene pigments such as C. I. Pigment Violet 29; naphthol AS pigments such as C. I. Pigment Violet 13, C. I. Pigment Violet 17, and C. I. Pigment Violet 50; dioxazine pigments such as C. I. Pigment Violet 23 and C. I. Pigment Violet 37; and the like.

The black pigment is a pigment having black color, and examples thereof include carbon black; titanium black; indazine pigments such as C. I. Pigment Black 1 (aniline black); perylene pigments such as C. I. Pigment Black 31 and C. I. Pigment Black 32; and the like.

Examples of the white pigment include basic lead carbonate ($2PbCO_3Pb(OH)_2$, so-called silver white), zinc oxide (ZnO, so-called zinc white), titanium oxide ($TiO_2$, so-called titanium white), strontium titanate ($SrTiO_3$, so-called strontium titanate white), and the like. The inorganic particles used as the white pigment may be particles composed of a single material or may be composite particles composed of, for example, an oxide of silicon, aluminum, zirconium, titanium or the like, an organic metal compound, and an organic compound.

Among the above, the titanium oxide has a smaller specific gravity than other white pigments, has a high refractive index, and is chemically and physically stable. Accordingly, as a pigment, the titanium oxide has strong covering power and strong adhesion, and exhibits excellent durability with respect to an acid, an alkali, and other environments. Therefore, the titanium oxide is preferably used. In addition to the titanium oxide, other white pigments may be used concurrently (the other white pigments may not be included in the aforementioned white pigments).

For dispersing the aforementioned pigments, it is possible to preferably use dispersion apparatuses such as a ball mill, a sand mill, an attritor, a roll mill, a jet mill, a homogenizer, a paint shaker, a kneader, an agitator, a Henschel mixer, a colloid mill, an ultrasonic homogenizer, a pearl mill, and a wet-type jet mill.

In the present invention, at the time of dispersing the aforementioned pigments, it is particularly preferable to add a dispersant which will be described later.

If necessary, at the time of dispersing the aforementioned pigments, a synergist appropriate for the various pigments may be added as a dispersion aid. The content of the dispersion aid in the ink composition is preferably 1 part by mass to 50 parts by mass with respect to 100 parts by mass of the aforementioned pigments.

A dispersion medium used for dispersing the aforementioned pigments in the ink composition is not particularly limited and can be appropriately selected according to the purpose. For example, the aforementioned low-molecular-weight polymerizable compound may be used as the dispersion medium, or a solvent may be used as the dispersion medium. Here, because the ink composition of the present invention is an active energy ray-curable ink, and the ink is cured after being applied onto a recording medium, the ink composition preferably does not contain the solvent. This is because if the solvent remains in the cured ink image, solvent resistance deteriorates, and a Volatile Organic Compound (VOC) of the residual solvent becomes a problem. Therefore, in view of improving dispersion suitability or improving handleability of the ink composition, it is preferable to use the aforementioned polymerizable compounds as the dispersion medium and to select a polymerizable compound having the lowest viscosity among the aforementioned polymerizable compounds.

The average particle size of the pigment is not particularly limited and can be appropriately selected according to the purpose. However, the smaller the particle size, the better the color developability, and accordingly, the particle size is preferably about 0.01 µm to about 0.4 µm, and more preferably 0.02 µm to 0.2 µm. In addition, the maximum particle size of the pigment is preferably 3 µm, and more preferably 1 µm. The particle size of the pigment can be adjusted by the type of the pigment, dispersant, and dispersion medium selected as well as dispersion conditions and filtering conditions set, and the like. Moreover, if the particle size of the pigment is controlled, it is possible to inhibit blocking of a head nozzle, to maintain the storage stability and transparency of the ink, and to maintain curing sensitivity.

The particle size of the pigment in the ink composition can be measured by a known measurement method. Specifically, the particle size can be measured by a centrifugal sedimentation light transmission method, an X-ray transmission method, a laser diffraction/light scattering method, or a dynamic light scattering method.

When the pigment is an organic pigment, the content of the pigment in the ink composition is preferably 1% by mass to 20% by mass, and more preferably 2% by mass to 10% by mass expressed in terms of solid contents. When the pigment is an inorganic pigment, the content of the pigment in the ink composition is preferably 1% by mass to 30% by mass, and more preferably 2% by mass to 25% by mass expressed in terms of solid contents.

The content of the colorant in the ink composition is appropriately selected according to color and purpose of use. However, the content of the colorant is preferably 0.01% by mass to 30% by mass with respect to the total mass of the ink composition.

(Component D) Sensitizer

In order to absorb a specific active energy ray and to accelerate decomposition of the polymerization initiator such as the component A or the like, the ink composition of the present invention may contain a compound that functions as a sensitizer (hereinafter, the compound will be also simply referred to as a "sensitizer").

Examples of the sensitizer include polynuclear aromatic compounds (for example, pyrene, perylene, triphenylene, and 2-ethyl-9,10-dimethoxyanthracene), xanthenes (for example, fluorescein, eosin, erythrosine, rhodamine B, and rose bengal), cyanines (for example, thiacarbocyanine and oxacarbocyanine), merocyanines (for example, merocyanine and carbomerocyanine), thiazines (for example, thionin, methylene blue, and toluidine blue), acridines (for example, acridine orange, chloroflavine, and acriflavine), anthraquinone (for example, anthraquinone), squarylium (for example, squarylium), coumarin (for example, 7-diethylamino-4-methyl coumarin), and the like.

One kind of the sensitizer may be used singly, or two or more kinds thereof may be used concurrently.

The ink composition of the present invention preferably contains a compound represented by Formula (3) or (4) as the sensitizer. If the sensitizer is used concurrently with the component A, an ink composition is obtained which reduces the amount of components in the film that are eluted (migrate) to the outside, suppresses the odor of a printed article, and has excellent curability and blocking resistance.

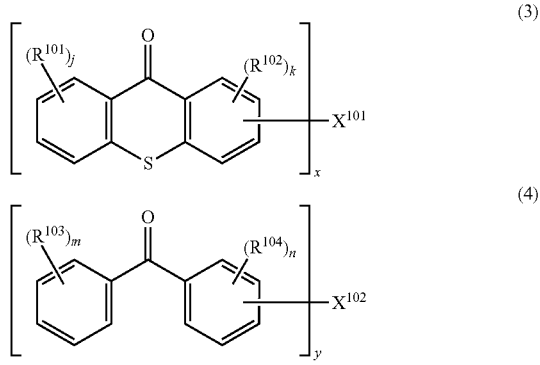

In Formulae (3) and (4), each of $R^{101}$, $R^{102}$, $R^{103}$, and $R^{104}$ independently represents an alkyl group having 1 to 5 carbon atoms or a halogen atom; each of x and y independently represents an integer of 2 to 4; each of j and m independently represents an integer of 0 to 4; and each of k and n independently represents an integer of 0 to 3. When each of j, k, m, and n is an integer of equal to or greater than 2, a plurality of $R^{101}$, $R^{102}$, $R^{103}$, and $R^{104}$ may the same as or different from each other respectively. $X^{101}$ represents an x-valent linking group containing at least one of a hydrocarbon chain, an ether bond, and an ester bond, and $X^{102}$ represents a y-valent linking group containing at least one of a hydrocarbon chain, an ether bond, and an ester bond.

<Compound Represented by Formula (3)>

The ink composition of the present invention preferably contains a compound represented by Formula (3) as the sensitizer.

In Formula (3), each of $R^{101}$ and $R^{102}$ independently represents an alkyl group having 1 to 5 carbon atoms or a halogen atom. The alkyl group having 1 to 5 carbon atoms may be linear, branched, or cyclic, but the alkyl group is preferably linear or branched. The alkyl group is preferably an alkyl group having 1 to 4 carbon atoms, more preferably an alkyl group having 2 or 3 carbon atoms, and even more preferably an ethyl group or an isopropyl group.

Examples of the halogen atom include a fluorine atom, a chlorine atom, a bromine atom, and an iodine atom. The halogen atom is preferably a chlorine atom.

Among the above groups, each of $R^{101}$ and $R^{102}$ particularly preferably represents an ethyl group, an isopropyl group, or a chlorine atom.

In Formula (3), j represents an integer of 0 to 4. j is preferably 0 to 2, and more preferably 0 or 1. When j is an integer of equal to or greater than 2, a plurality of $R^1$ may be the same as or different from each other.

In Formula (3), k represents an integer of 0 to 3. k is preferably 0 to 2, more preferably 0 or 1, and even more preferably 0. When k is equal to or greater than 2, a plurality of $R^{102}$ may be the same as or different from each other.

In Formula (3), x represents an integer of 2 to 4. x is more preferably 3 or 4, and even more preferably 4.

In Formula (3), $X^{101}$ represents an x-valent linking group composed of an x-valent hydrocarbon chain having 2 to 300 carbon atoms that may contain an ether bond (—O—) and/or an ester bond (—(C=O)—O—).

The compound represented by Formula (3) has a plurality of (number of x) thioxanthone structures (the structure shown in the square brackets in Formula (1)) excluding $X^{101}$ that represents a linking group. The thioxanthone structures may be the same as or different from each other, and are not particularly limited. From the viewpoint of synthesis, they are preferably the same as each other.

In the compound represented by Formula (3), the positions in which the compound is substituted with thioxanthone are described as below.

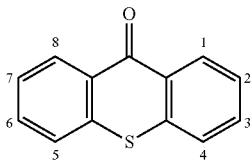 [SMILES: O=c1c2ccccc2sc2ccccc12]

Provided that $X^{101}$ is substituted in the 1-position to the 4-position, $X^{101}$ is preferably substituted in the 2-position, the 3-position, or the 4-position, more preferably substituted in the 2-position or the 4-position, and even more preferably substituted in the 4-position.

The position in which $R^{101}$ is substituted is not particularly limited. However, $R^{101}$ is preferably substituted in the 6-position or the 7-position, and more preferably substituted in the 6-position.

The position in which $R^{102}$ is substituted is not particularly limited. However, $R^{102}$ is preferably substituted in the 1-position, the 2-position, or the 3-position, and more preferably substituted in the 1-position.

The compound represented by Formula (3) is preferably a compound represented by the following Formula (3').

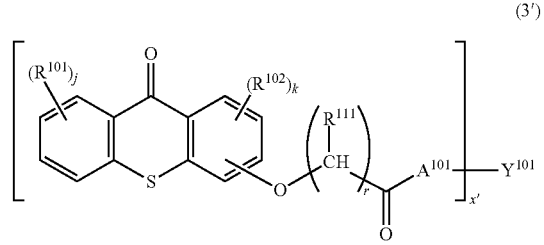

$R^{101}$, $R^{102}$, j and k in Formula (3') have the same definition as $R^{101}$, $R^{102}$, j and k in Formula (3) respectively, and the preferable range thereof is also the same.

In Formula (3'), each $R^{111}$ independently represents a hydrogen atom or an alkyl group having 1 to 4 carbon atoms. $R^{111}$ is preferably a hydrogen atom, a methyl group, or an ethyl group, and more preferably a hydrogen atom.

In Formula (3'), each r independently represents an integer of 1 to 6. r is preferably an integer of 1 to 3, more preferably 1 or 2, and even more preferably 1. When r is equal to or greater than 2, a plurality of $R^{111}$ may be the same as or different from each other.

x' represents an integer of 2 to 4. x' is preferably 2 or 3, and more preferably 2.

$Y^{101}$ represents a residue formed from a polyhydroxy compound having at least x' hydroxyl groups by removing x' hydrogen atoms of the hydroxyl groups. $Y^{101}$ is preferably a residue formed as a result of removing hydrogen atoms of all of the hydroxy groups (in the number of x') from a polyhydroxy compound having the hydroxy groups in the number of x'. Specifically, $Y^{101}$ is preferably a residue formed as a result of removing hydrogen atoms of hydroxy groups in the number of x' from a polyhydroxy compound selected from the group consisting of ethylene glycol, propylene glycol, butylene glycol, glycerin, trimethylolpropane, ditrimethylolpropane, and pentaerythritol, or preferably a residue formed as a result of removing hydrogen atoms of all of the hydroxy groups.

In Formula (3'), $A^{101}$ represents a group selected from the group consisting of the following (i) to (iii).

*—[O(CHR$^{112}$CHR$^{113}$)$_a$]$_z$—**  (i)

*—[O(CH$_2$)$_b$CO]$_z$—**  (ii)

*—[O(CH$_2$)$_b$CO]$_{(z-1)}$—[O(CHR$^{112}$CHR$^{113}$)$_a$]—**  (iii)

In Formulae (i) to (iii), one of $R^{112}$ and $R^{113}$ represents a hydrogen atom, and the other of $R^{112}$ and $R^{113}$ represents a hydrogen atom, a methyl group, or an ethyl group; a represents an integer of 1 or 2; b represents an integer of 4 or 5; z represents an integer of 1 to 20; * represents a position in which the group is bonded to a carbonyl carbon; and ** represents a position in which the group is bonded to $Y^{101}$.

$A^{101}$ is preferably a group represented by Formula (i), and more preferably *—(OCH$_2$CH$_2$)$_z$—**, *—(OCH$_2$CH$_2$CH$_2$CH$_2$)$_z$—**, or *—O(CH(CH$_3$)CH$_2$)$_z$—**. In this case, z is preferably an integer of 3 to 10.

The molecular weight of the compound represented by Formula (3) is preferably 500 to 3,000, more preferably 800 to 2,500, and even more preferably 1,000 to 2,000.

If the molecular weight is equal to or greater than 500, an ink composition is obtained which inhibits the elution of the compound from the cured film and suppresses the migration, odor, and blocking. In contrast, if the molecular weight is equal to or less than 3,000, the steric hindrance of the molecule is reduced, a degree of freedom of the molecule is maintained in the liquid and the film, and a high degree of sensitivity is obtained.

When the compound represented by Formula (3) is a mixture of a plurality of compounds that differ from each other in terms of the number of carbon atoms or the like, the weight-average molecular weight of the compound is preferably within the above range.

Specific examples of the compound represented by Formula (3) will be shown below, but the present invention is not limited to the following compounds.

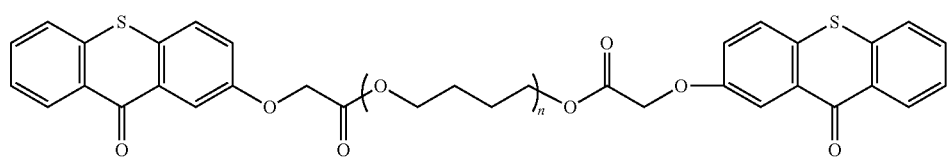

I-A n = 1-20

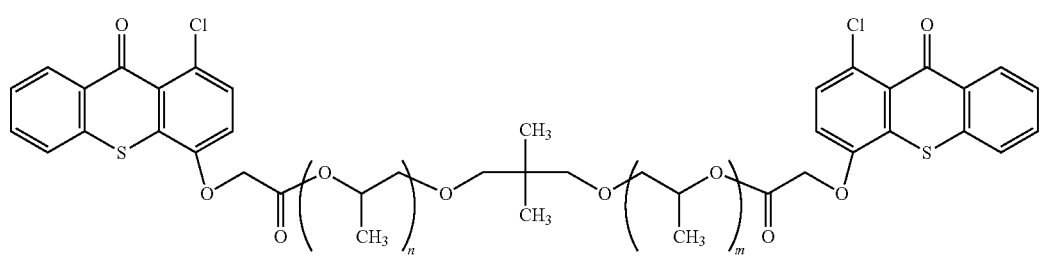

I-B n = 1-20
m = 1-20

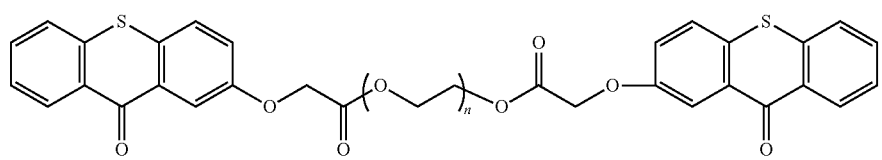

I-C n = 1-20

-continued

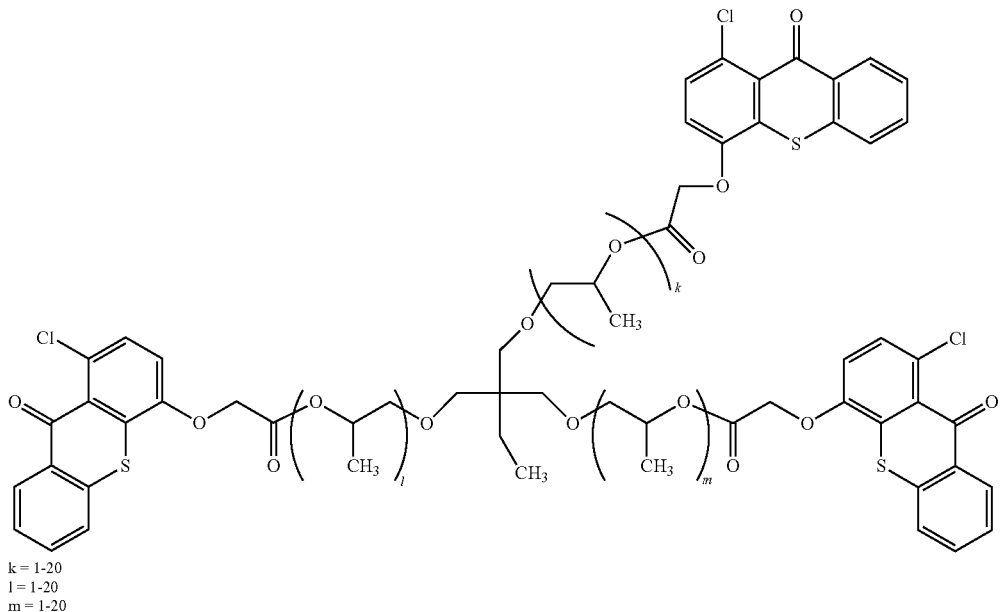

I-D k = 1-20
l = 1-20
m = 1-20

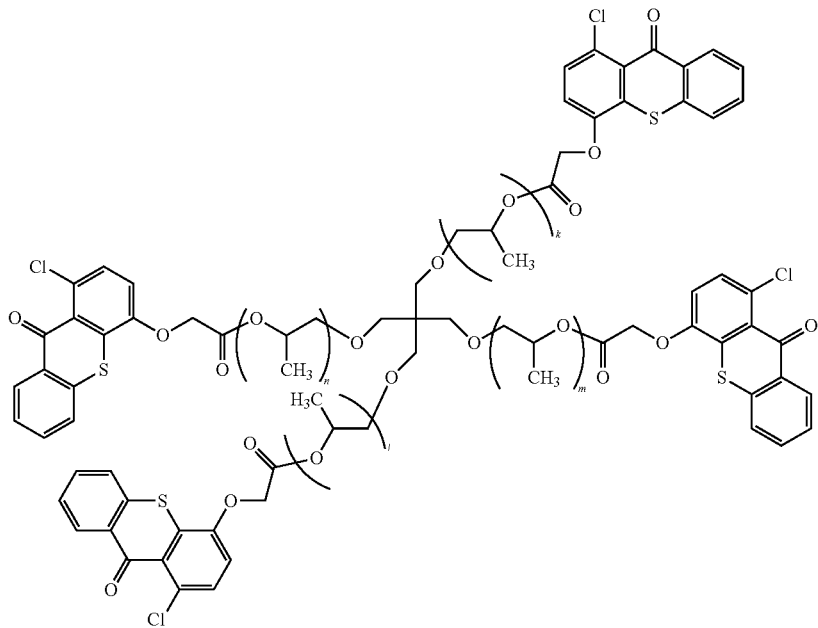

I-E k = 1-20
l = 1-20
m = 1-20
n = 1-20

Among the above compounds, the compound (I-A) or (I-E) is preferable, and the compound (I-E) is more preferable.

Commercially available compounds can also be used as the compound represented by Formula (3). Specific examples of the commercially available compounds include SPPEDCURE 7010 (1,3-di({α-[1-chloro-9-oxo-9H-thioxanthen-4-yl]oxy}acetylpoly[oxy(l-methylethylene)])oxy)-2,2-bis({α-[1-chloro-9-oxo-9H-thioxanthen-4-yl]oxy}acetylpoly[oxy(l-methylethylene)])oxy methyl) propane, CAS No. 1003567-83-6) and OMNIPOL TX (Polybutyleneglycol bis(9-oxo-9H-thioxanthenyloxy)acetate, CAS No. 813452-37-8).

The compound represented by Formula (3) can be manufactured through a known reaction and is not particularly limited. For example, the compound represented by Formula (3') can be prepared by reacting a compound represented by the following Formula (3-1) with a compound represented by the following Formula (3-2).

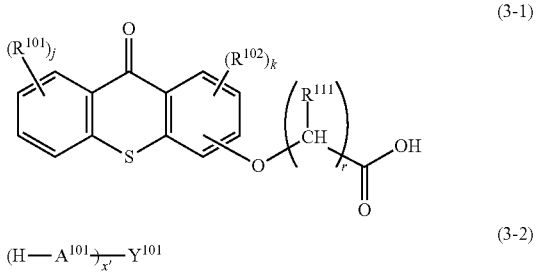

(3-1)

(3-2)

$R^{101}$, $R^{102}$, $R^{111}$, $A^{101}$, $Y^{101}$, j, k, r, and x' in Formulae (3-1) and (3-2) have the same definition as $R^{101}$, $R^{102}$, $R^{111}$, $A^{101}$, $Y^{101}$, j, k, r, and x' in Formula (3'), and the preferable range thereof is also the same.

The aforementioned reaction is preferably performed in the presence of a solvent. Examples of appropriate solvents include aromatic hydrocarbon such as benzene, toluene, and xylene.

Furthermore, the reaction is preferably performed in the presence of a catalyst. Examples of the catalyst include sulfonic acid (for example, p-toluenesulfonic acid and methanesulfonic acid), an inorganic acid (for example, sulfuric acid, hydrochloric acid, and phosphoric acid), a Lewis acid (aluminum chloride, boron trifluoride, and an organotitanate), and the like.

The reaction temperature and reaction time are not particularly limited.

After the reaction ends, the reaction product is isolated from the reaction mixture by known means and then washed and dried if necessary. In this way, the product can be separated.

<Compound Represented by Formula (4)>

The ink composition of the present invention preferably contains a compound represented by Formula (4) as a sensitizer.

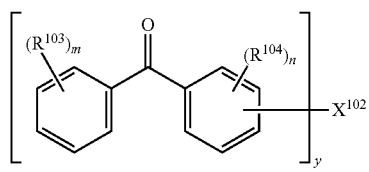

(4)

In Formula (4), each of $R^{103}$ and $R^{104}$ independently represents an alkyl group having 1 to 5 carbon atoms or a halogen atom; m represents an integer of 0 to 4; n represents an integer of 0 to 3; and y represents an integer of 2 to 4. When each of m and n is an integer of equal to or greater than 2, a plurality of $R^{103}$ and a plurality of $R^{104}$ may be the same as or different from each other respectively. $X^{102}$ represents a y-valent linking group containing at least one of a hydrocarbon chain, an ether bond, and an ester bond.

In Formula (4), each of $R^{103}$ and $R^{104}$ independently represents an alkyl group having 1 to 5 carbon atoms or a halogen atom. The alkyl group having 1 to 5 carbon atoms may be linear, branched, or cyclic, but is preferably linear or branched. The alkyl group is preferably an alkyl group having 1 to 4 carbon atoms, more preferably an alkyl group having 2 or 3 carbon atoms, and even more preferably an ethyl group or an isopropyl group. Examples of the halogen atom include a fluorine atom, a chlorine atom, a bromine atom, and an iodine atom. The halogen atom is preferably a chlorine atom. Each of $R^{103}$ and $R^{104}$ is particularly preferably an ethyl group, an isopropyl group, or a chlorine atom.

In Formula (4), m represents an integer of 0 to 4. m is preferably 0 to 2, and more preferably 0 or 1. When m is an integer of equal to or greater than 2, a plurality of $R^{103}$ may be the same as or different from each other.

In Formula (4), n represents an integer of 0 to 3. n is preferably 0 to 2, more preferably 0 or 1, and even more preferably 0. When n is an integer of equal to or greater than 2, a plurality of $R^{104}$ may be the same as or different from each other.

In Formula (4), y represents an integer of 2 to 4. y is preferably 2 or 3, and more preferably 2.

In Formula (4), $X^{102}$ represents a y-valent linking group containing at least one group selected from the group consisting of a hydrocarbon chain, an ether bond (—O—), and an ester bond (—(C=O)—O—).

The compound represented by Formula (4) has a plurality of (a number of y) benzophenone structures (the structure shown in the square brackets in Formula (4)) excluding $X^2$ which is a linking group. The benzophenone structures may be the same as or different from each other and are not particularly limited. From the viewpoint of synthesis, they are preferably the same as each other.

In the compound represented by Formula (4), the positions in which the compound is substituted with benzophenone are described as below.

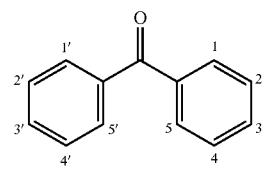 [SMILES: O=C(c1ccccc1)c1ccccc1]

Provided that $X^{102}$ is substituted in the 1-position to the 5-position, $X^{102}$ is preferably substituted in the 2-position or the 3-position, and more preferably substituted in the 3-position.

The position in which $R^{103}$ is substituted is not particularly limited. However, $R^{103}$ is preferably substituted in the 2'-position or the 3'-position, and more preferably substituted in the 3'-position.

The position in which $R^{104}$ is substituted is not particularly limited. However, $R^{104}$ is preferably substituted in the 2-position, the 3-position, or the 4-position.

The compound represented by Formula (4) is preferably a compound represented by the following Formula (4').

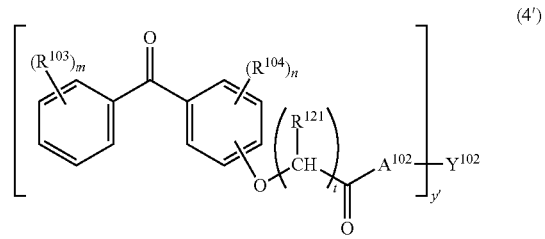

(4')

$R^{103}$, $R^{104}$, m, and n in Formula (4') have the same definitions as $R^{103}$, $R^{104}$, m, and n in Formula (2) respectively, and the preferable range thereof is also the same.

In Formula (4'), each $R^{121}$ independently represents a hydrogen atom or an alkyl group having 1 to 4 carbon atoms. $R^{121}$ is preferably a hydrogen atom, a methyl group, or an ethyl group, and more preferably a hydrogen atom.

In Formula (4'), each t independently represents an integer of 1 to 6. t is preferably an integer of 1 to 3, more preferably 1 or 2, and even more preferably 1. When t is equal to or greater than 2, a plurality of $R^{121}$ may be the same as or different from each other.

y' represents an integer of 2 to 4. y' is preferably 2 or 3, and more preferably 2.

$Y^{102}$ represents a residue formed from a polyhydroxy compound having at least x' hydroxyl groups by removing x' hydrogen atoms of the hydroxyl groups. $Y^{102}$ is preferably a residue formed as a result of removing hydrogen atoms of all of the hydroxy groups (in the number of y') from a polyhydroxy compound having the hydroxy groups in the number of y'. Specifically, $Y^{102}$ is preferably a residue formed as a result of removing hydrogen atoms of the hydroxy groups in the number of y' from a polyhydroxy compound selected from the group consisting of ethylene glycol, propylene glycol, butylene glycol, glycerin, trimethylolpropane, ditrimethylolpropane, and pentaerythritol, or preferably a residue formed as a result of removing hydrogen atoms of all of the hydroxy groups.

In Formula (4'), $A^{102}$ represents a group selected from the group consisting of following Formulae (i) to (iii).

*—[O(CHR$^{112}$CHR$^{113}$)$_a$]$_z$—** (i)

*—[O(CH$_2$)$_b$CO]$_z$—** (ii)

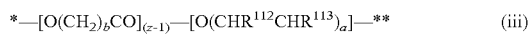

*—[O(CH$_2$)$_b$CO]$_{(z-1)}$—[O(CHR$^{112}$CHR$^{113}$)$_a$]—** (iii)

In Formulae (i) to (iii), one of $R^{112}$ and $R^{113}$ represents a hydrogen atom, and the other of $R^{112}$ and $R^{113}$ represents a hydrogen atom, a methyl group, or an ethyl group; a represents an integer of 1 or 2; b represents an integer of 4 or 5; z represents an integer of 1 to 20; * represents a position in which the group is bonded to a carbonyl carbon; and ** represents a position in which the group is bonded to $Y^{102}$.

$A^{102}$ is preferably a group represented by Formula (i), and more preferably *—(OCH$_2$CH$_2$)$_z$—**, *—(OCH$_2$CH$_2$CH$_2$CH$_2$)$_z$—**, or *—O(CH(CH$_3$)CH$_2$)$_z$—**. In this case, z is preferably an integer of 3 to 10.

The molecular weight of the compound represented by Formula (4) is preferably 500 to 3,000, more preferably conductive film 800 to 2,500, and even more preferably 1,000 to 2,000.

If the molecular weight is equal to or greater than 500, an ink composition is obtained which inhibits the elution of the compound from the cured film and suppresses the migration, odor, and blocking. In contrast, if the molecular weight is equal to or less than 3,000, the steric hindrance of the molecule is reduced, a degree of freedom of the molecule is maintained in the liquid and the film, and a high degree of sensitivity is obtained.

When the compound represented by Formula (4) is a mixture of a plurality of compounds that differ from each other in terms of the number of carbon atoms or the like, the weight-average molecular weight of the compound is preferably within the above range.

Specific examples of the compound represented by Formula (4) will be shown below, but the present invention is not limited to the following compounds.

I-F

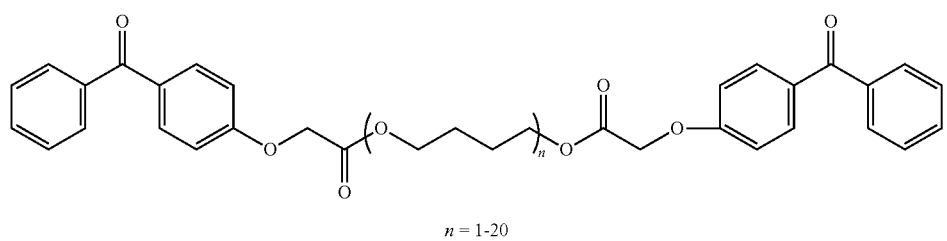

n = 1-20

I-G

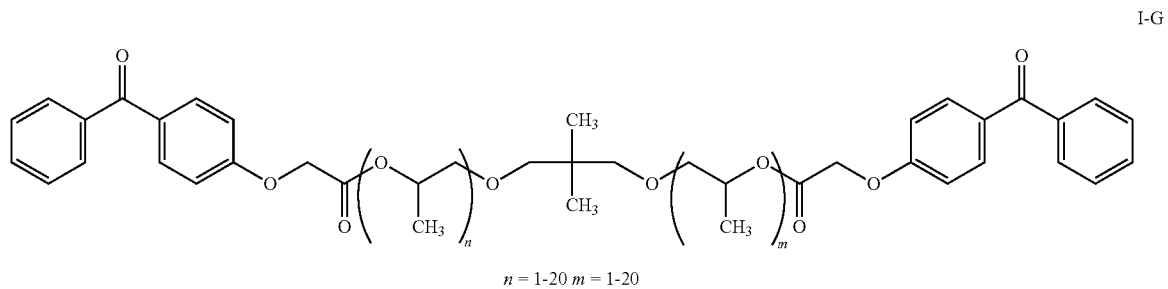

n = 1-20 m = 1-20

I-H

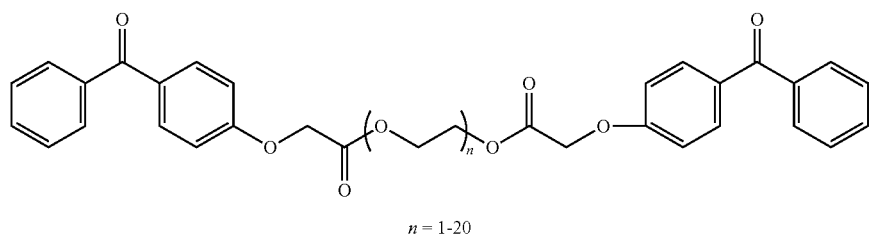

n = 1-20

-continued

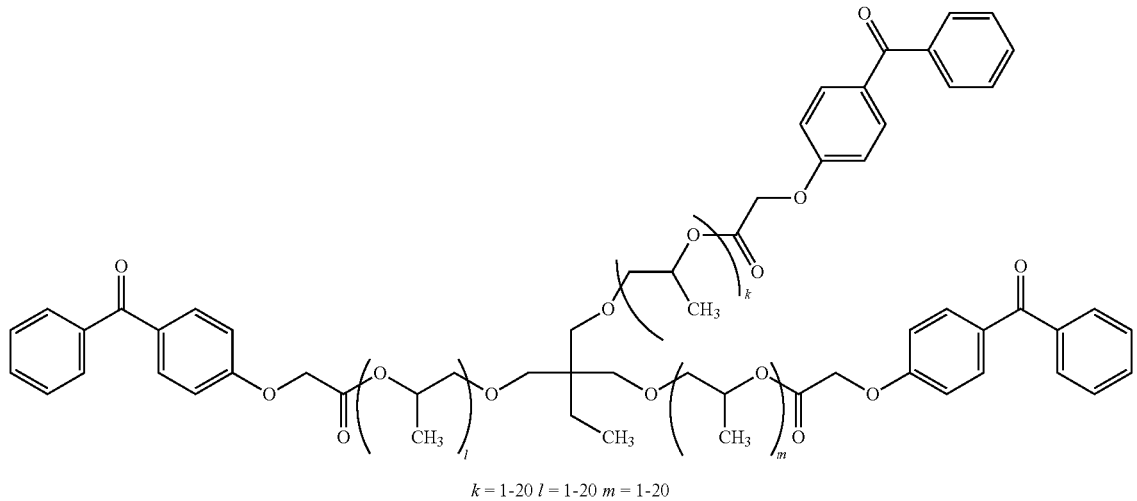

$k = 1\text{-}20 \; l = 1\text{-}20 \; m = 1\text{-}20$

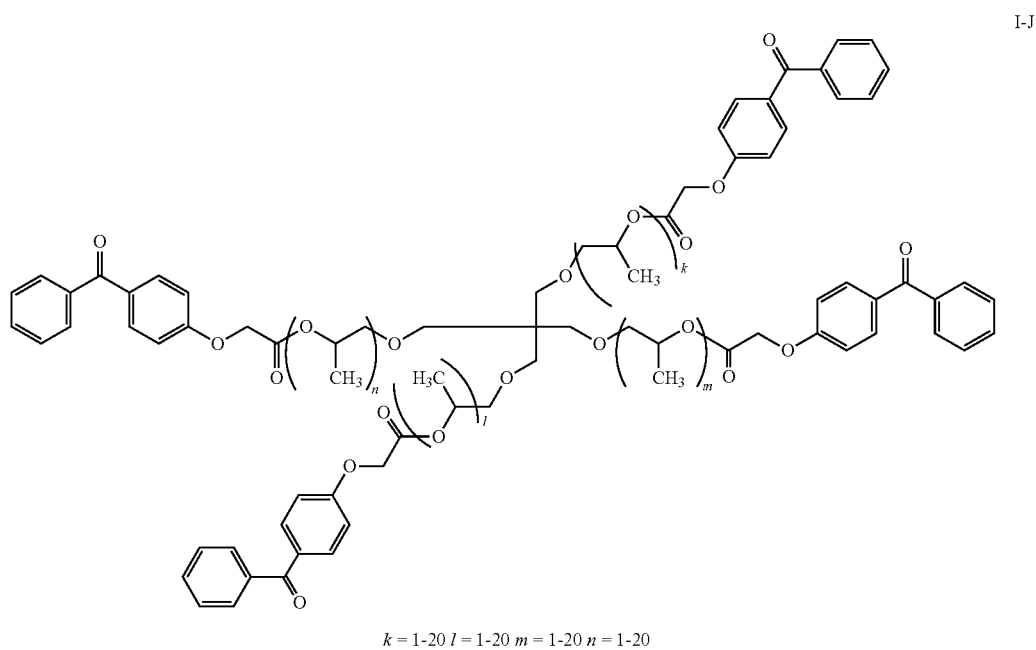

$k = 1\text{-}20 \; l = 1\text{-}20 \; m = 1\text{-}20 \; n = 1\text{-}20$

Commercially available compounds can also be used as the compound represented by Formula (4). Specific examples of the commercially available compounds include OMNIPOL BP (Polybutyleneglycol bis(4-benzoylphenoxy) acetate, CAS No. 515136-48-8).

The compound represented by Formula (4) can be manufactured through a known reaction and is not particularly limited. For example, the compound represented by Formula (4') can be prepared by reacting a compound represented by the following Formula (4-1) with a compound represented by the following Formula (4-2).

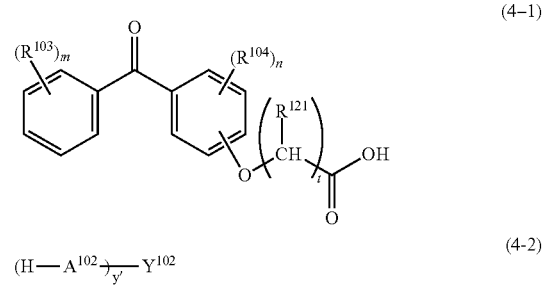

(4-1)

(4-2)

$R^{103}$, $R^{104}$, $R^{121}$, $A^{102}$, $Y^{102}$, m, n, t, and y' in Formulae (4-1) and (4-2) have the same definitions as $R^{103}$, $R^{104}$, $R^{121}$, $A^{102}$, $Y^{102}$, m, n, t, and y' in Formula (4') respectively, and the preferable range thereof is also the same.

The aforementioned reaction is preferably performed in the presence of a solvent. Examples of appropriate solvents include aromatic hydrocarbons such as benzene, toluene, and xylene.

Furthermore, the reaction is preferably performed in the presence of a catalyst. Examples of the catalyst include sulfonic acid (for example, p-toluenesulfonic acid and methanesulfonic acid), an inorganic acid (for example, sulfuric acid, hydrochloric acid, and phosphoric acid), a Lewis acid (aluminum chloride, boron trifluoride, and an organotitanate), and the like.

The reaction temperature and reaction time are not particularly limited.

After the reaction ends, the reaction product is isolated from the reaction mixture by known means and then washed and dried if necessary. In this way, the product can be separated.

From the viewpoint of increasing sensitivity and suppressing the migration, odor, and blocking, the content of the compound represented by Formula (4) is preferably 1% by mass to 5% by mass, and more preferably 2% by mass to 4% by mass, with respect to the total mass of the ink composition.

The compound represented by Formula (4) is more preferably the compound represented by Formula (4-1).

The total content of the sensitizer is preferably 0.01% by mass to 10.0% by mass, more preferably 0.05% by mass to 5.0% by mass, and even more preferably 0.1% by mass to 2.4% by mass, with respect to the total mass of the ink composition. If the total content of the sensitizer is within the above range, curability becomes excellent.

From the viewpoint of suppressing migration and odor and improving curability, a ratio between the total content of the component A and the total content of the sensitizer is preferably 1:1.5 to 8:1.5 ((content of the component A): (content of the sensitizer)) in terms of mass.

<Other Polymerization Initiators>

If necessary, the ink composition of the present invention can contain other polymerization initiators in addition to the component A.

The aforementioned other polymerization initiators are preferably radical polymerization initiators or cationic polymerization initiators, and particularly preferably radical polymerization initiators. For example, it is possible to use the polymerization initiators described in JP2009-138172A.

The total content of the aforementioned other polymerization initiators is preferably equal to or less than 10% by mass, more preferably equal to or less than 5% by mass, even more preferably equal to or less than 1% by mass, and particularly preferably 0% by mass, with respect to the total mass of the ink composition. If the total content of other polymerization initiators is within the above range, curability becomes excellent.

The aforementioned other polymerization initiators are preferably compounds having a molecular weight of equal to or greater than 340.

The total content of the aforementioned other polymerization initiators is preferably smaller than the content of the component A.

<Co-Sensitizer>

For the purpose of further improving sensitivity or inhibiting polymerization from being hindered due to oxygen, the ink composition of the present invention may contain a co-sensitizer.

Examples of the co-sensitizer include amines (for example, the compounds described in "Journal of Polymer Society" (M. R. Sander et al., Vol. 10, p. 3173, 1972), JP1969-20189B (JP-S44-20189B), JP1976-82102A (JP-S51-82102A), JP1977-134692A (JP-S52-134692A), JP1984-138205A (JP-S59-138205A), JP1985-84305A (JP-S60-84305A), JP1987-18537A (JP-S62-18537A), JP1989-33104A (JP-S64-33104A), and Research Disclosure No. 33825) and the like. Specific examples of the amines preferably include triethanolamine, p-dimethylaminobenzoic acid ethyl ester, p-formyldimethylaniline, p-methylthiodimethylaniline, and the like.

Examples of the co-sensitizer also preferably include thiols and sulfides (for example, the thiol compounds described in JP1978-702A (JP-S53-702A), JP1980-500806B (JP-S55-500806B), and JP1993-142772A (JP-H05-142772A) and the disulfide compounds described in JP1981-75643A (JP-S56-75643A)), and the like. Specific examples of the thiols and sulfides include 2-mercaptobenzothiazole, 2-mercaptobenzoxazole, 2-mercaptobenzimidazole, 2-mercapto-4(3H)-quinazoline, β-mercaptonaphthalene, and the like.

Examples of the co-sensitizer also include amino acid compounds (for example, N-phenylglycine), the organic metal compounds (for example, tributyl tin acetate) described in JP1973-42965B (JP-S48-42965B), the hydrogen donator described in JP1980-34414B (JP-S55-34414B), the sulfur compounds (for example, trithiane) described in JP1994-308727A (JP-H06-308727A), the phosphorus compounds (for example, diethyl phosphite) described in JP1994-250387A (JP-H06-250387A), the Si—H and Ge—H compounds described in JP1996-54735A (JP-H08-54735A), and the like.

One kind of the co-sensitizer may be used singly, or two or more kinds thereof may be used concurrently.

The content of the co-sensitizer is not particularly limited, but is preferably 0.1% by mass to 10% by mass with respect to the total mass of the ink composition.

<Dispersant>

The ink composition of the present invention preferably contains a dispersant. Particularly, when a pigment is used, the ink composition preferably contains a dispersant such that the pigment is stably dispersed in the ink composition. The dispersant is preferably a polymer dispersant. In the present invention, the "polymer dispersant" refers to a dispersant having a weight-average molecular weight of equal to or greater than 1,000.

Examples of the polymer dispersant include DISPERBYK-101, DISPERBYK-102, DISPERBYK-103, DISPERBYK-106, DISPERBYK-111, DISPERBYK-161, DISPERBYK-162, DISPERBYK-163, DISPERBYK-164, DISPERBYK-166, DISPERBYK-167, DISPERBYK-168, DISPERBYK-170, DISPERBYK-171, DISPERBYK-174, and DISPERBYK-182 (manufactured by BYK-Chemie GmbH); EFKA4010, EFKA4046, EFKA4080, EFKA5010, EFKA5207, EFKA5244, EFKA6745, EFKA6750, EFKA7414, EFKA745, EFKA7462, EFKA7500, EFKA7570, EFKA7575, and EFKA7580 (manufactured by Efka additives); Disperse aid 6, Disperse aid 8, Disperse aid 15, and Disperse aid 9100 (manufactured by SAN NOPCO LIMITED); various SOLSPERSE dispersants such as SOLSPERSE 3000, 5000, 9000, 12000, 13240, 13940, 17000, 22000, 24000, 26000, 28000, 32000, 36000, 39000, 41000, and 71000 (manufactured by The Lubrizol Corporation.); Adeka Pluronic L31, F38, L42, L44, L61, L64, F68, L72, P95, F77, P84, F87, P94, L101, P103, F108, L121, and P-123 (manufactured by ADEKA CORPORATION); Ionet S-20 (manufactured by Sanyo Chemical Industries, Ltd.); and Disparlon KS-860, 873 SN, 874 (polymer dispersant), #2150 (aliphatic polyvalent carboxylic acid), #7004 (polyether ester type) (manufactured by Kusumoto Chemicals, Ltd.).

The content of the dispersant in the ink composition is appropriately selected according to the purpose of use. However, the content of the dispersant is preferably 0.05% by mass to 15% by mass with respect to the total mass of the ink composition.

<Surfactant>

In order to make the ink composition exhibit stable ejectability over a long period of time, a surfactant may be added to the ink composition of the present invention.

Examples of the surfactant include those described in JP1987-173463A (JP-S62-173463A) and JP1987-183457A (JP-S62-183457A). For example, the surfactant includes anionic surfactants such as dialkyl sulfosuccinates, alkylnaphthalene sulfosuccinates, and fatty acid salts, nonionic surfactants such as polyoxyethylene alkyl ethers, polyoxyethylene alkyl allyl ethers, acetylene glycols, and polyoxyethylene polyoxypropylene block copolymers, and cationic surfactants such as alkyl amine salts and quaternary ammonium salts. As the surfactant, a fluorine-based surfactant (for example, an organic fluoro compound) or a silicone-based surfactant (for example, a polysiloxane compound) may also be used. The organic fluoro compound is preferably hydrophobic. For example, the organic fluoro compound include a fluorine-based surfactant, an oil-like fluorine-based compound (for example, fluorine oil), and a solid-like fluorine compound resin (for example, a tetrafluoroethylene resin). Examples of the organic fluoro compound include those described in JP1982-9053B (JP-S57-9053B) (the eighth to seventeenth columns) and JP1987-135826A (JP-S62-135826A). The aforementioned polysiloxane compound is preferably a modified polysiloxane compound obtained by introducing an organic group into a portion of a methyl group of dimethylpolysiloxane. For example, the polysiloxane compound may be polyether-, methyl styrene-, alcohol-, alkyl-, aralkyl-, fatty acid ester-, epoxy-, amine-, amino-, or mercapto-modified, but the group used for the modification is not particularly limited. The polysiloxane compound may be modified with a combination of these groups. Particularly, from the viewpoint of improving ejection stability in an inkjet, a polyether-modified polysiloxane compound is preferable. Examples of the polyether-modified polysiloxane compound include SILWET L-7604, SILWET L-7607N, SILWET FZ-2104, and SILWET FZ-2161 (manufactured by Nippon Unicar Company Limited); BYK306, BYK307, BYK331, BYK333, BYK347, and BYK348 (manufactured by BYK-Chemie GmbH); and KF-351A, KF-352A, KF-353, KF-354L, KF-355A, KF-615A, KF-945, KF-640, KF-642, KF-643, KF-6020, X-22-6191, X-22-4515, KF-6011, KF-6012, KF-6015, and KF-6017 (manufactured by Shin-Etsu Chemical Co., Ltd.).

Among these, the silicone-based surfactant is preferable.

The content of the surfactant in the ink composition of the present invention is appropriately selected according to the purpose of use. However, the content of the surfactant is preferably 0.0001% by mass to 1% by mass with respect to the total mass of the ink composition.

<Solvent>

Adding a solvent to the ink composition of the present invention is also effective for improving the adhesiveness between the ink composition and a recording medium.

Examples of the solvent include a ketone-based solvent such as acetone, methyl ethyl ketone, or diethyl ketone; an alcohol-based solvent such as methanol, ethanol, 2-propanol, 1-propanol, 1-butanol, or tert-butanol; a chlorine-based solvent such as chloroform or methylene chloride; an aromatic solvent such as benzene or toluene; an ester-based solvent such as ethyl acetate, butyl acetate, or isopropyl acetate; an ether-based solvent such as diethyl ether, tetrahydrofuran, or dioxane; a glycol ether-based solvent such as ethylene glycol monomethyl ether, ethylene glycol dimethyl ether, or tripropylene glycol monomethyl ether; a cyclic ester-based solvent such as γ-butyrolactone; an amide-based solvent such as 2-methylpyrrolidone or 2-pyrrolidone; and the like.

In this case, it is effective to add the solvent in an amount within a range in which the solvent resistance or a Volatile Organic Compound (VOC) does not become a problem. The amount of the solvent is preferably 0.1% by mass to 5% by mass, and more preferably 0.1% by mass to 3% by mass, with respect to the total mass of the ink composition.

As a dispersion medium for various components such as the pigment in the ink composition, the solvent may be added to the ink composition. Alternatively, the solvent is not added to the ink composition, and the polymerizable compound may be used as a dispersion medium. However, because the ink composition of the present invention is an active energy ray-curable ink composition and is cured after being applied onto a recording medium, the ink composition preferably does not contain the solvent. This is because if the solvent remains in the cured ink image, the solvent resistance deteriorates, or the problem of VOC of the residual solvent arises. For this reason, it is preferable to use the polymerizable compound as a dispersion medium. Particularly, from the viewpoint of improving dispersion suitability or improving handleability of the ink composition, it is preferable to select a polymerizable monomer having the lowest viscosity from among the polymerizable compounds.

Furthermore, according to the purpose, various additives can be concurrently used in the ink composition of the present invention. For example, from the viewpoint of improving weather resistance of the obtained image and preventing fading of the obtained image, an ultraviolet absorber can be used. Moreover, in order to improve stability of the ink composition, an antioxidant can be added to the ink composition.

The ink composition of the present invention may also contain various known additives in addition to the aforementioned components.

Specifically, examples of the additives other than the aforementioned components include various organic fading inhibitors and metal complex-based fading inhibitors; conductive salts for controlling ejectability, such as potassium thiocyanate, lithium nitrate, ammonium thiocyanate, and dimethylamine hydrochloride; polymer compounds for adjusting physical properties of the film; and the like.

For the purpose of adjusting physical properties of the film, various polymer compounds can be added to the ink composition of the present invention. For example, as the polymer compounds, it is possible to use an acryl-based polymer, a polyvinyl butyral resin, a polyurethane resin, a polyamide resin, a polyester resin, an epoxy resin, a phenol resin, a polycarbonate resin, a polyvinyl formal resin, shellac, a vinyl-based resin, an acryl-based resin, a rubber-based resin, waxes, and other natural resins. Furthermore, two or more kinds of these compounds may be used concurrently.

In addition to these, if necessary, the ink composition can contain, for example, a basic compound, a leveling additive, a matting agent, waxes for adjusting physical properties of the film, and a tackifier (viscosity imparting agent) not hindering polymerization that is for improving the adhesiveness between the ink composition and a recording medium such as polyolefin or polyethylene terephthalate (PET).

Considering ejectability of the ink composition ejected from an inkjet nozzle, the viscosity of the ink composition of the present invention at a temperature at the time of ejection is preferably 0.5 mPa·s to 30 mPa·s, more preferably 0.5 mPa·s to 20 mPa·s, and most preferably 1 mPa·s to 15 mPa·s. It is preferable to appropriately adjust and determine the compositional ratio of the ink composition such that the viscosity falls into the above range.

The viscosity of the ink composition at 25° C. (room temperature) is preferably equal to or greater than 1 mPa·s and equal to or less than 200 mPa·s, more preferably equal to or greater than 2 mPa·s and equal to or less than 50 mPa·s, and even more preferably equal to or greater than 2.5 mPa·s and equal to or less than 30 mPa·s. If the viscosity at room temperature is set to be high, even when a porous recording medium is used, it is possible to prevent the ink composition from permeating the recording medium, to reduce the amount of an uncured monomer, and to suppress odor. Furthermore, it is possible to prevent spreading of ink dots when the ink droplets land on a recording medium, and as a result, image quality is improved. If the viscosity of the ink composition is equal to or less than 200 mPa·s at 25° C., the ink composition is easily delivered to an inkjet head or the like in an apparatus.

The surface tension of the ink composition of the present invention is preferably 20 mN/m to 40 mN/m, and more preferably 23 mN/m to 35 mN/m. When recording is performed on various recording media such as polyolefin, PET, coated paper, and uncoated paper, from the viewpoint of blurring and permeation, the surface tension of the ink composition is preferably equal to or greater than 20 mN/m. Furthermore, from the viewpoint of wettability, the surface tension of the ink composition is preferably equal to or less than 35 mN/m.

The ink composition of the present invention prepared as above is printed on a recording medium by an inkjet printer, and then the printed ink composition is cured by being irradiated with an active energy ray. In this way, recording can be preferably performed.

In a printed article obtained from the ink composition of the present invention, an image portion exhibits excellent strength. Accordingly, the ink composition can be used for various purposes such as the formation of an ink receiving layer (image portion) of a planographic printing plate, in addition to the formation of an image.

(Inkjet Recording Method, Inkjet Recording Apparatus, and Printed Article)

The inkjet recording method of the present invention is a method for forming an image by ejecting the ink composition of the present invention onto a recording medium (a support, a recording material, or the like) for inkjet recording, and curing the ink composition ejected onto the recording medium by irradiating the ink composition with an active energy ray.

More specifically, the inkjet recording method of the present invention preferably includes ($a^1$) ejecting the ink composition of the present invention onto a recording medium, and ($b^1$) curing the ejected ink composition by irradiating the ink composition with an active energy ray.

The inkjet recording method of the present invention includes the steps ($a^1$) and ($b^1$). As a result, on a recording medium, an image is formed by the cured ink composition.

It is preferable that each of the steps ($a^1$) and ($b^1$) of the inkjet recording method of the present invention is performed two or more times in the same portion on the recording medium. That is, the inkjet recording method of the present invention is preferably performed in a multi-pass mode in which the ink composition is repeatedly ejected onto the same portion. If the inkjet recording method of the present invention is performed in the multi-pass mode by using the ink composition of the present invention, an image having better glossiness is obtained.

The printed article of the present invention is preferably a printed article that is recorded by the inkjet recording method of the present invention by using the ink composition of the present invention.

The ink composition of the present invention is suitable for printing a package. Particularly, the ink composition of the present invention is suitable for printing a package for packing foods. In this case, the inkjet recording method of the present invention preferably includes the following steps in the following order.

(a) A step of ejecting the ink composition from an inkjet head and printing the ink composition on a support for a package having a film thickness of equal to or less than 150 µm, and (b) a step of irradiating the ejected ink composition with an active energy ray In the steps ($a^1$) and ($b^1$) in the inkjet recording method of the present invention, an inkjet recording apparatus, which will be specifically described below, can be used.

<Inkjet Recording Apparatus>

An inkjet recording apparatus that can be used for the inkjet recording method of the present invention is not particularly limited. It is possible to arbitrarily select and use a known inkjet recording apparatus that can achieve intended resolution. That is, any of known inkjet recording apparatuses including commercially available products can eject the ink composition to a recording medium in the steps ($a^1$) and ($b^1$) of the inkjet recording method of the present invention.

Examples of the inkjet recording apparatus usable in the present invention include an apparatus having an ink supply system, a temperature sensor, and a source of an active energy ray.

The ink supply system includes, for example, a main tank that contains the ink composition of the present invention, supply piping, an ink supply tank that is right ahead of an inkjet head, a filter, and a piezoelectric inkjet head. The piezoelectric inkjet head can be driven such that multi-size dots can be ejected preferably in an amount of 1 pl to 100 pl, and more preferably in an amount of 8 pl to 30 pl, preferably at a resolution of 320×320 dpi to 4,000×4,000 dpi, more preferably at a resolution of 400×400 dpi to 1,600×1,600 dpi, and even more preferably at a resolution of 720×720 dpi. In the present invention, "dpi" refers to the number of dots per 2.54 cm.

As described above, it is preferable for the temperature of the ejected ink composition of the present invention to be kept constant. Therefore, it is preferable for the inkjet recording apparatus to have means for stabilizing temperature of the ink composition. The site to be kept at a constant temperature includes a piping system from an ink tank (intermediate tank when the apparatus has an intermediate tank) to the jet surface of a nozzle and all members. That is, the area from the ink supply tank to the portion of the inkjet head can be insulated and heated.

The temperature control method is not particularly limited. However, for example, it is preferable to provide a plurality of temperature sensors to the respective piping portions so as to control heating according to the flow rate of the ink composition and the environmental temperature. The temperature sensor can be provided in the ink supply tank and in the vicinity of the nozzle of the inkjet head. Moreover, it is preferable that the head unit to be heated is a heat-blocking unit or is thermally insulated, such that the body of the apparatus is not influenced by the temperature of external air. In order to shorten printer startup time taken for heating or to reduce thermal energy loss, it is preferable to insulate the heating unit from other sites and to reduce a total thermal capacity of the heating unit.

Usually, the viscosity of an active energy ray-curable ink composition such as the ink composition of the present invention is higher than the viscosity of an aqueous ink composition that is generally used as an ink composition for inkjet recording. Accordingly, the viscosity of the active energy ray-curable ink composition greatly varies with the temperature at the time when the ink composition is ejected. The variation in the viscosity of the ink composition exerts a great influence on the change in the liquid droplet size and on the change in the ejection rate of the liquid droplets, and results in the deterioration of image quality. Therefore, it is important for the temperature of the ink composition at the time of ejection to be kept as constant as possible. Consequently, in the present invention, it is appropriate for the temperature of the ink composition to be controlled preferably within a range of a set temperature ±5° C., more preferably within a range of a set temperature ±2° C., and most preferably within a range of a set temperature ±1° C.

Next, the steps ($b^1$) and (b) will be described.

The ink composition ejected onto a recording medium is cured by being irradiated with an active energy ray (actinic ray). This is because the polymerization initiator contained in the ink composition of the present invention is decomposed by being irradiated with the active energy ray and thus generates a polymerization initiating species such as radicals, and the initiating species functions to cause and accelerate a polymerization reaction of the polymerizable compound. At this time, if both the polymerization initiator and the sensitizer are present in the ink composition, the sensitizer in situ is excited by absorbing the active energy ray and comes into contact with the polymerization initiator. As a result, decomposition of the polymerization initiator is accelerated, and thus a curing reaction with higher sensitivity can occur.

The polymerization initiating system of the ink composition of the present invention exhibits sufficient sensitivity even when a low-power active energy ray is used. Therefore, it is appropriate that the ink composition is cured at the illuminance of an exposed surface of preferably 10 mW/cm$^2$ to 4,000 mW/cm$^2$ and more preferably 20 mW/cm$^2$ to 2,500 mW/cm$^2$.

As a source of the active energy ray, a mercury lamp, gas•solid-state laser, and the like are mainly used. Furthermore, as a light source used for curing an ultraviolet-curable ink composition for inkjet recording, a mercury lamp or a metal halide lamp is widely known. However, currently, from the viewpoint of environmental protection, it is strongly desired not to use a mercury lamp. Therefore, in view of industrial and environmental aspects, it is extremely useful to replace the mercury lamp with a GaN-based semiconductor ultraviolet light emitting device. In addition, LED (UV-LED) and LD (UV-LD) are expected to be used as a light source for a photocuring-type inkjet since these devices are compact, have a long life and high efficiency, and are low-cost.

Moreover, a light emitting diode (LED) and a laser diode (LD) can be used as a source of an active energy ray. Particularly, when a source of ultraviolet rays is required, an ultraviolet LED and an ultraviolet LD can be used. For example, NICHIA CORPORATION put an ultraviolet LED, of which the main emission spectrum has a wavelength within a range of 365 nm to 420 nm, on the market. When the shorter wavelength is required, the LED disclosed in U.S. Pat. No. 6,084,250A that can emit an active energy ray focused on 300 nm and 370 nm can be considered. Furthermore, other ultraviolet LEDs are available and can emit radiation of different ultraviolet bands. A UV-LED is the source of the active energy ray that is particularly preferred in the present invention. Particularly, a UV-LED having a peak wavelength at 340 nm to 400 nm is preferable.

The maximum illuminance of the LED on a recording medium is preferably 10 mW/cm$^2$ to 2,000 mw/cm$^2$, more preferably 20 mW/cm$^2$ to 1,000 mW/cm$^2$, and particularly preferably 50 mW/cm$^2$ to 800 mW/cm$^2$.

It is appropriate that the ink composition of the present invention is irradiated with such an active energy ray preferably for 0.01 seconds to 120 seconds, and more preferably for 0.1 seconds to 90 seconds.

The irradiation conditions of the active energy ray and basic irradiation method are disclosed in JP1985-132767A (JP-S60-132767A). Specifically, a light source is disposed on both sides of a head unit including an apparatus for ejecting the ink composition, and the head unit and the light source are scanned by a so-called shuttle method to perform the irradiation of the active energy ray. The irradiation of the active energy ray is performed for a certain period of time (for example, preferably for 0.01 seconds to 0.5 seconds, more preferably for 0.01 seconds to 0.3 seconds, and even more preferably for 0.01 seconds to 0.15 seconds) after the ink composition lands on a recording medium. If the time period from the landing of the ink composition to the irradiation is controlled to be an extremely short period of time, it is possible to prevent the ink composition having landed on a recording medium from spreading before being cured. Furthermore, it is preferable to shorten the aforementioned time period because, even when a porous recording medium used, the ink composition can be exposed to light before it permeates the recording medium into a deep portion that the light source does not reach, and therefore an unreacted monomer is prevented from remaining.

In addition, the curing may be completed by using another light source that is not driven. Examples of the irradiation method include a method of using optical fiber and a method of irradiating a recording portion with reflected light by irradiating a mirror surface disposed on a lateral surface of the head unit with collimated light (UV light). These curing methods can also be applied to the inkjet recording method of the present invention.

If the aforementioned inkjet recording method is adopted, even when various recording media, which differ from each other in terms of the wettability of the surface thereof, are used, a dot diameter of the ink composition having landed on the recording media can be kept constant, and thus image quality is improved. Furthermore, in order to obtain a color image, it is preferable to superimpose ink compositions sequentially from an ink composition with color of low brightness. If ink compositions are superimposed on each other sequentially from an ink composition of low brightness, the irradiated radiation easily reaches the ink composition in the lower portion, and excellent curing sensitivity, reduction in the residual monomer, and improvement of the adhesiveness can be expected. During the irradiation, ink compositions of all colors can be ejected and exposed to light at the same time. However, from the viewpoint of acceleration of curing, it is preferable that an ink composition of a single color is separately exposed to light.

In this way, the ink composition of the present invention is cured with high sensitivity by being irradiated with an active energy ray and can form an image on the surface of a recording medium.

The ink composition of the present invention is preferably used in the form of an ink set composed of a plurality of inks for inkjet recording.

In the inkjet recording method of the present invention, the order of ejecting colored ink compositions is not particularly limited. However, the colored ink compositions are preferably provided onto a recording medium from a colored ink composition of high brightness. When colored ink compositions of yellow, cyan, magenta, and black are used, it is preferable that the ink compositions are provided onto a recording medium in order of yellow, cyan, magenta, and black. Furthermore, when a white ink composition is also used, it is preferable that the ink compositions are provided onto a recording medium in order of white, yellow, cyan, magenta, and black. The present invention is not limited to the above, and it is possible to use a set of inks of the present invention that includes at least ink compositions of seven colors in total such as yellow, light cyan, light magenta, cyan, magenta, black, and white. In this case, it is preferable that the ink compositions are provided onto a recording medium in order of white, light cyan, light magenta, yellow, cyan, magenta, and black.

FIG. 1 is a schematic view of an inkjet recording apparatus preferably used in the present invention. A support 6 hung between support winding-up rolls 5 and 5', which are transport means of the support, is transported in the direction of the arrow, and from an inkjet head unit 7 equipped with ejection heads ejecting droplets of ink compositions of respective colors, the ink compositions of the respective colors (K: black, Y: yellow, M: magenta, C: cyan, W: white) are ejected to the support 6.

As shown in FIG. 1, an LED light source unit 1 is surrounded by an inert gas blanket 2 and is connected to an inert gas generating apparatus 4 through an inert gas piping 3. The inert gas generating apparatus 4, which is means for creating a hypoxic atmosphere inside the inert gas blanket 2, supplies inert gas into the inert gas blanket 2 through the inert gas piping 3. At the initial stage, air is inside the inert gas blanket 2. However, when the inert gas generating apparatus 4 is moved, the air inside the inert gas blanket 2 is substituted with inert gas. The inert gas refers to general gas such as $N_2$, $H_2$, and $CO_2$ or rare gas such as He, Ne, and Ar. Among these, from the viewpoint of safety, ease of availability, and cost, $N_2$ is preferably used.

<Recording Medium>

The recording medium to which the ink composition of the present invention can be applied is not particularly limited, and it is possible to use general paper such as uncoated paper and coated paper, various nonabsorbent resin materials used for so-called soft packaging, or resin films obtained by making the nonabsorbent resin materials into films.

Examples of various plastic films include a polyethylene terephthalate (PET) film, a biaxially oriented polystyrene (OPS) film, a biaxially oriented polypropylene (OPP) film, a biaxially oriented nylon (ONy) film, a polyvinyl chloride (PVC) film, a polyethylene (PE) film, a cellulose triacetate (TAC) film, and the like.

In addition, examples of plastic usable as materials of the recording medium include polycarbonate, an acryl resin, an acrylonitrile-butadiene-styrene (ABS) copolymer, polyacetal, polyvinyl alcohol (PVA), rubbers, and the like. Furthermore, metals and glasses can be used as the recording medium.

The ink composition of the present invention contains a specific polymerization initiator. Therefore, the ink composition can be preferably used as a curable ink composition for inkjet that can be cured by being irradiated with an active energy ray. Moreover, the ink composition of the present invention can directly form a high-quality image even on a nonabsorbent recording medium based on digital data. Accordingly, the ink composition is also preferably used for preparing a printed article having a large area.

The ink composition of the present invention contains a specific polymerization initiator. Therefore, the ink composition can be cured even in a small exposure amount. It is considered that, for this reason, the ink composition make a contribution to reduce system or running cost by using an inexpensive light source having low exposure intensity and to improve a printing rate by shortening the exposure time. Furthermore, because the ink composition is rapidly cured after exposure, it is possible to inhibit blurring of an image and to form a clear image.

(High-Molecular-Weight Polymerization Initiator)

The high-molecular-weight polymerization initiator in a first embodiment of the present invention is a (meth)acryl resin which has a weight-average molecular weight of equal to or greater than 1,000 and has an acylphosphine oxide structure represented by the following Formula (1) or (2) on a side chain thereof.

Furthermore, the high-molecular-weight polymerization initiator in a second embodiment of the present invention is a hyperbranched polymer which has a weight-average molecular weight of equal to or greater than 1,000 and has one or more acylphosphine oxide structures represented by the following Formula (1) or (2) on a molecular terminal thereof

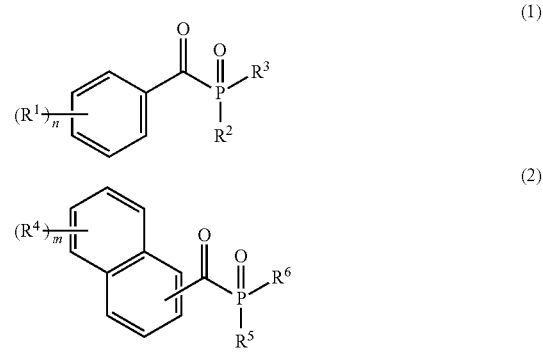

In the formula, each $R^1$ independently represents an alkyl group having 1 to 8 carbon atoms, an aryl group, an alkoxy group having 1 to 4 carbon atoms, or a linking group linked to a main chain of a (meth)acryl resin; at least one $R^1$ is a linking group linked to a main chain of a (meth)acryl resin; each of $R^2$ and $R^3$ independently represents an alkyl group, an aryl group, or an alkoxy group; n represents an integer of 1 to 5; each $R^4$ independently represents an alkyl group having 1 to 8 carbon atoms, an aryl group, an alkoxy group having 1 to 4 carbon atoms, or a linking group linked to a main chain of a (meth)acryl resin; at least one $R^4$ is a linking group linked to a main chain of a (meth)acryl resin; each of $R^5$ and $R^6$ independently represents an alkyl group, an aryl group, or an alkoxy group; and m represents an integer of 1 to 7.

A preferable embodiment of the high-molecular-weight polymerization initiator in the first or second embodiment of the present invention is the same as the embodiment described above for the component A.

The high-molecular-weight polymerization initiator in the second embodiment of the present invention is preferably a hyperbranched polymer which has a weight-average molecular weight of equal to or greater than 1,000 and has three or more acylphosphine oxide structures represented by the Formula (1) or (2) on a molecular terminal thereof.

A manufacturing method of the high-molecular-weight polymerization initiator in the first or second embodiment of the present invention is not particularly limited, and the high-molecular-weight polymerization initiator may be manufactured by a known manufacturing method.

For example, the high-molecular-weight polymerization initiator in the first embodiment of the present invention may be synthesized by polymerizing a (meth)acryl resin and then introducing the acylphosphine oxide structure represented by Formula (1) or (2) into the (meth)acryl resin through a polymer reaction. Alternatively, the high-molecular-weight polymerization initiator may be synthesized by polymerizing a monomer having an acylphosphine oxide structure represented by Formula (1) or (2).

Moreover, for example, the high-molecular-weight polymerization initiator in the second embodiment of the present invention can be synthesized by synthesizing a core portion and then linking the acylphosphine oxide structure represented by Formula (1) or (2) to a terminal thereof.

A method for introducing the acylphosphine oxide structure represented by Formula (1) is not particularly limited. However, for example, it is possible to preferably use a method in which a compound having a methyl group on a benzene ring of an acyl group of a monoacylphosphine oxide compound is used, the methyl group is brominated and turns into —$CH_2Br$ such that the compound is substituted with bromine atoms of —$CH_2Br$, and a high-molecular-weight portion of a main chain or a core of the component A is introduced into the compound. Examples of the aforementioned bromination include a method in which a thermal radical generator such as azoisobutyronitrile or benzoyl peroxide and a brominating agent such as N-bromosuccinimide are caused to act on a compound having a methyl group on a benzene ring of an acyl group of a monoacylphosphine oxide compound.

Furthermore, for examples, as the method for introducing the acylphosphine oxide structure, it is also possible to preferably use a method of introducing the acylphosphine oxide structure by means of a reaction between a carboxylic acid chloride and an alkoxydiphenylphosphine.

EXAMPLES

Hereinafter, the present invention will be more specifically described based on examples, but the present invention is not limited to the examples. Herein, unless otherwise specified, "part" and "%" are based on mass.

<(Component A) High-Molecular-Weight Polymerization Initiator Having Weight-Average Molecular Weight of Equal to or Greater than 1,000>

A-1 to A-11 and B-1 to B-8 used in the present examples are the high-molecular-weight polymerization initiators having the aforementioned structure.

<Synthesis of A-1>

—Synthesis of Benzyl Bromide Intermediate E-1—

10 g (28.7 mmol) of 2,4,6-trimethylbenzoyl diphenylphosphine oxide (LUCIRIN TPO, manufactured by Ciba-Geigy Japan Ltd.), 5.11 g (28.7 mmol) of N-bromosuccinimide, and 115 mL of chlorobenzene were put into a 500 mL three-neck flask equipped with a stirring rod, a nitrogen introduction pipe, and a thermometer, and heated and stirred for 1 hour under a nitrogen stream at 65° C. After solids were completely dissolved, 0.26 g of azoisobutyronitrile was added thereto, and the resultant was further reacted for 6 hours. A solution obtained after the reaction was left to cool, water was then added thereto, and a reaction product was extracted twice by using ethyl acetate. Thereafter, by column chromatography (hexane:ethyl acetate=7:3), a benzyl bromide intermediate E-1 was isolated. $^1$H NMR (400 MHz, $CDCl_3$): δ=2.04 (s, 6H), 4.38 (s, 2H), 7.03 (s, 2H), 7.50~7.61 (m, 6H), 7.97~8.02 (m, 4H)

—Synthesis of Methacrylate E-2—

In a 500 mL three-neck flask equipped with a stirring rod and a thermometer, 9.15 g (28.09 mmol) of cesium carbonate was added to a mixed solution of dimethylformamide (DMF) (40 mL) and pure water (8 mL), and the resultant was dissolved. Thereafter, the mixed solution was concentrated by being stirred for 12 hours under reduced pressure, and 1.33 g (15.45 mmol) of methacrylic acid was added thereto. Subsequently, a dimethylformamide (DMF 30 mL) solution containing 6.0 g (14.04 mmol) of the benzyl bromide intermediate E-1 was added thereto, and the resultant was stirred for 5 hours at room temperature (25° C.). Water was then added to the obtained reaction liquid, and the reaction product was extracted twice by using ethyl acetate. Then, by column chromatography (hexane:ethyl acetate=8:2), a methacrylate E-2 was isolated.

$^1$H NMR (400 MHz, $CDCl_3$): δ=2.00 (s, 3H), 2.04 (s, 6H), 5.10 (s, 2H), 6.37 (d, 1H), 6.48 (d, 1H), 7.03 (s, 2H), 7.45~7.68 (m, 6H), 7.96~8.10 (m, 4H)

—Synthesis (Polymerization) of A-1—

Under a nitrogen stream, methyl ethyl ketone (4.3 mL) and 4.35 g (21.51 mmol) of dodecanethiol was added to 3.0 g (7.17 mmol) of the methacrylate E-2, and the resultant was stirred at 70° C. Thereafter, 0.24 g of azoisobutyronitrile was added thereto, and the resultant was reacted for 6 hours. After the reaction ended, the resultant was reprecipitated using hexane:ethyl acetate=9:1, thereby obtaining a polymer A-1. The weight-average molecular weight of the polymer A-1 was 1,100.

<—Synthesis (polymerization) of A-2—>

Under a nitrogen stream, methyl ethyl ketone (4.3 mL) was added to 3.0 g (7.17 mmol) of the methacrylate E-2, and the resultant was stirred at 70° C. Thereafter, 0.62 g (3.07 mmol) of dodecanethiol was added thereto, and the resultant was stirred at 70° C. Subsequently, 0.12 g of azoisobutyronitrile was added thereto, and the resultant was reacted for 6 hours. After the reaction ended, the resultant was reprecipitated using hexane:ethyl acetate=9:1, thereby obtaining a polymer A-2. The weight-average molecular weight of the polymer A-2 was 8,000.

<—Synthesis (Polymerization) of A-3—>

Under a nitrogen stream, methyl ethyl ketone (4.3 mL) was added to 3.0 g (7.17 mmol) of the methacrylate E-2, and the resultant was stirred at 70° C. Thereafter, 0.12 g of azoisobutyronitrile was added thereto, and the resultant was reacted for 6 hours. After the reaction ended, the resultant was reprecipitated using hexane:ethyl acetate=9:1, thereby obtaining a polymer A-3. The weight-average molecular weight of the polymer A-3 was 32,000.

<Synthesis of A-4 to A-5>

A polymer A-4 was obtained in the same manner as in Synthesis (polymerization) of polymer A-1, except that, in Synthesis (polymerization) of polymer A-1, the methacrylate E-2 and Blemmer PME-100 (manufactured by NOF CORPORATION) were used instead of the methacrylate E-2.

A polymer A-5 was obtained in the same manner as in Synthesis of polymer A-4, except that, in Synthesis of polymer A-4, the methacrylate E-2 and Blemmer PME-200 (manufactured by NOF CORPORATION) were used instead of the methacrylate E-2 and Blemmer PME-100 (manufactured by NOF CORPORATION).

<Synthesis of A-6>

—Synthesis of Benzyl Bromide Intermediate E-3—

10 g (23.9 mmol) of Irgacure 819 (phenyl bis(2,4,6-trimethylbenzoyl)phosphine oxide), 4.25 g (23.9 mmol) of N-bromosuccinimide, and 100 mL of chlorobenzene were put into a 200 mL three-neck flask equipped with a stirring rod and a thermometer, and the resultant was heated and stirred for 1 hour at 65° C. under a nitrogen stream. After solids were completely dissolved, 0.22 g of azoisobutyronitrile was added thereto, and the resultant was further reacted for 6 hours. After the solution obtained after the reaction was left to cool, water was added thereto, and the reaction product was extracted twice by using ethyl acetate. Thereafter, by column purification, a compound E-3 (a benzyl bromide intermediate E-3 of Irgacure 819) was isolated in which the position of benzyl on one side of phenyl bis(2,4,6-trimethylbenzoyl)phosphine oxide had been brominated.

$^1$H NMR (400 MHz, CDCl$_3$): δ=2.32 (s, 3H), 2.50 (s, 12H), 4.56 (s, 2H), 7.10 (d, 4H), 7.32~7.51 (m, 3H), 7.70-7.85 (m, 2H)

—Synthesis of Methacrylate E-4—

In a 500 mL three-neck flask equipped with a stirring rod and a thermometer, 6.55 g (20.11 mmol) of cesium carbonate was dissolved in a mixed solution of dimethylformamide (DMF) (30 mL) and water (10 ml). Thereafter, the resultant was concentrated by being stirred for 12 hours under reduced pressure. 0.80 g (11.06 mmol) of methacrylic acid was added thereto, a DMF (30 mL) solution containing 5.0 g (10.05 mmol) of the benzyl bromide intermediate E-3 was also added thereto, and the resultant was stirred for 5 hours at room temperature. Water was added to the obtained reaction liquid, and the reaction product was extracted twice by using ethyl acetate. Subsequently, by column chromatography (hexane:ethyl acetate=8:2), a methacrylate E-4 was isolated.

$^1$H NMR (400 MHz, CDCl$_3$): δ=2.34 (s, 3H), 2.55 (s, 12H), 5.20 (s, 2H), 5.59 (d, 1H), 5.95 (d, 1H), 6.31 (d, 1H), 7.11 (s, 2H), 7.25 (s, 2H), 7.40-7.50 (m, 3H), 7.80-8.01 (m, 2H)

—Synthesis of A-6—

A corresponding polymer A-6 was obtained in the same manner as in Synthesis (polymerization) of polymer A-1, except that, in Synthesis (polymerization) of polymer A-1, the methacrylate E-4 was used instead of methacrylate E-2.

<Synthesis of A-7>

100 ml of tetrahydrofuran, 8.81 g (58.45 mmol) of triethylamine, and 10.0 g (53.14 mmol) of 2-hydroxy-1-naphthoic acid were put into a 500 mL three-neck flask equipped with a stirring rod and a thermometer, then 8.81 g (58.45 mmol) of TBSCl (tert-butyl dimethyl chlorosilane) was also added thereto, and the resultant was stirred for 2 hours at 5° C. The solution after the reaction was heated to room temperature, an aqueous ammonium chloride solution was added thereto, and the reaction product was extracted twice by using ethyl acetate, thereby obtaining crude 2-tert-butyldimethylsiloxy-1-naphthoic acid E-5 (unpurified product). In a 500 mL three-neck flask, 6.06 g (50.91 mmol) of thionyl chloride was caused to act on the crude 2-tert-butyldimethylsiloxy-1-naphthoic acid E-5, and then distilled away under reduced pressure. Thereafter, 100 ml of toluene and 12.79 g (55.54 mmol) of ethoxydiphenyl phosphine were added to the resultant, and the resultant was reacted for 4 hours at 70° C. 100 ml of water and 14.52 g (55.54 mmol) of tetrabutyl ammonium fluoride (TBAF) were added to the reaction liquid, the resultant was reacted for 3 hours at 40° C., and water was added thereto. Subsequently, the reaction product was extracted twice by using ethyl acetate, thereby obtaining crude 2-hydroxy-1-naphthoic acid phosphine oxide E-6.

The crude 2-hydroxy-1-naphthoic acid phosphine oxide E-6, 100 ml of tetrahydrofuran, 5.43 g (52.00 mmol) of methacrylic acid chloride, and 5.74 g (56.72 mmol) of triethylamine were put into a 500 mL three-neck flask, and the resultant was stirred for 2 hours at 5° C. The solution obtained after the reaction was heated to room temperature, an aqueous ammonium chloride solution was added thereto, and the reaction product was extracted twice by using ethyl acetate and recrystallized over isopropyl alcohol, thereby obtaining 2-methacryloxy-1-naphthoic acid phosphine oxide E-7.

$^1$H NMR (400 MHz, CDCl$_3$): δ=2.01 (s, 3H), 6.20 (d, 1H), 6.43 (d, 1H), 7.08~7.20 (m, 1H), 7.40~9.28 (m, 14H)

A polymer A-7 was obtained in the same manner as in Synthesis of polymer A-4, except that, in Synthesis of polymer A-4, the 2-methacryloxy-1-naphthoic acid phosphine oxide E-7 was used instead of the methacrylate E-2.

<Synthesis of A-8>

6.0 g (26.8 mmol) of 3-isocyanate-2,4,6-trimethylbenzoyl chloride was put into a 200 ml eggplant-shaped flask, and nitrogen purging was performed in the flask under reduced pressure. Thereafter, 107 ml of dry tetrahydrofuran was added thereto and dissolved. 5.4 ml (27 mmol) of methoxydiphenyl phosphine was then added dropwise to the solution at 65° C., and the resultant was stirred for 1.5 hours. After the solvent was distilled away under reduced pressure, the resultant was subjected to an azeotropic process twice with 107 ml of hexane and then dried under reduced pressure, thereby obtaining 11.9 g of a crude product of 3-isocyanate-2,4,6-trimethylbenzoyldiphenyl phosphine oxide. 10.5 g of the crude product of 3-isocyanate-2,4,6-trimethylbenzoyldiphenyl phosphine oxide was put into a 100 ml eggplant-shaped flask shielded from light by aluminum foil, nitrogen purging was performed in the flask under reduced pressure, and then 40 ml of dimethylformamide and 6.5 ml (53 mmol) of 2-hydroxyethyl methacrylate were sequentially added thereto. The solution was stirred for 13 hours at 50° C. and then diluted with 200 ml of a mixed solvent of hexane/ethyl acetate (1:1, volume ratio). The solution was washed with water, and then the reaction product was extracted by using 100 ml of a mixed solvent of hexane/ethyl acetate (1:1, volume ratio). The obtained organic phase was washed with an aqueous saturated sodium hydrogen carbonate solution and saturated saline, and then dried over magnesium sulfate. After the magnesium sulfate was separated by filtration, the filtrate was concentrated under reduced pressure. The residue obtained in this way was purified by silica gel column chromatography while being shielded from light. Ethyl acetate was added to white solids obtained by concentration performed under reduced pressure, and the suspension was filtered, thereby obtaining 3.0 g of a methacrylate E-8.

$^1$H NMR (300 MHz, CDCl$_3$): δ=8.02~7.95 (m, 4H), 7.58~7.47 (m, 6H), 6.90 (s, 1H), 6.3~6.0 (m, 2H), 5.57 (s, 1H), 4.36 (s, 4H), 2.21 (s, 3H), 1.95 (s, 9H)

A polymer A-8 was obtained in the same manner as in Synthesis of polymer A-4, except that, in Synthesis of polymer A-4, the methacrylate E-8 was used instead of the methacrylate E-2.

<Synthesis of A-9>

10 g (60.02 mmol) of 4-vinylbenzoyl chloride (synthesized by the method described in Tetrahedron, 2002, 58, 4, 741) was reacted with 15.20 g (66.02 mmol) of ethoxydiphenyl phosphine, and then the resultant was purified by column chromatography, thereby obtaining 4-ethenylbenzoylphosphine oxide E-9.

$^1$H NMR (400 MHz, CDCl$_3$): δ=5.20 (d, 1H), 5.61 (d, 1H), 6.62 (d, 1H), 7.40~8.78 (m, 14H)

A polymer A-9 was obtained in the same manner as in Synthesis of polymer A-4, except that, in Synthesis of polymer A-4, the 4-ethenylbenzoylphosphine oxide E-9 was used instead of the methacrylate E-2.

<Synthesis of A-10>

5 g (21.85 mmol) of 2,6-dimethyl-4-trimethylsilyloxybenzoyl chloride and 5.54 g (24.04 mmol) of ethoxydiphenyl phosphine were put into a 200 ml eggplant-shaped flask, and the resultant was reacted for 5 hours at 70° C. Thereafter, 100 ml of water and 6.86 g (26.22 mmol) of TBAF were added thereto, and the resultant was reacted for 2 hours at 40° C., thereby obtaining crude 2,6-dimethyl-4-hydroxybenzoylphosphine oxide E-10. 50 ml of tetrahydrofuran, 6.34 g of the crude 2,6-dimethyl-4-hydroxybenzoylphosphine oxide E-10, 4.51 g (21.64 mmol) of 2-tosyloxyethyl methacrylate, and 2.39 g (23.60 mmol) of triethylamine were put into a 200 ml eggplant-shaped flask, and the resultant was stirred for 2 hours at 5° C. Thereafter, the solution obtained after the reaction was heated to room temperature, an aqueous ammonium chloride solution was added thereto, the reaction product was extracted twice by using ethyl acetate, and the resultant was recrystallized over isopropyl alcohol, thereby obtaining 2,6-dimethyl-4-(2-methacryloxyethyloxyl)benzoylphosphine oxide E-11.

A polymer A-10 was obtained in the same manner as in Synthesis of polymer A-4, except that, in Synthesis of polymer A-4, the 2,6-dimethyl-4-(2-methacryloxyethyloxyl) benzoylphosphine oxide E-11 was used instead of the methacrylate E-2.

<Synthesis of A-11>

Crude 2-hydroxy-1-naphthoic acid phosphine oxide E-6 was obtained in the same manner as in Synthesis of A-7. 17.6 g (47.26 mmol) of the crude 2-hydroxy-1-naphthoic acid phosphine oxide E-6, 100 ml of tetrahydrofuran, 10.83 g (52.00 mmol) of 2-mesyloxyethyl methacrylate, and 5.74 g (56.72 mmol) of triethylamine were put into a 500 mL three-neck flask, and the resultant was stirred for 2 hours at 5° C. Thereafter, the solution obtained after the reaction was heated to room temperature, an aqueous ammonium chloride solution was added thereto, the reaction product was extracted twice by using ethyl acetate, and the resultant was recrystallized over isopropyl alcohol, thereby obtaining 2-(2-methacryloxyethyl)-1-naphthoic acid phosphine oxide E-12.

$^1$H NMR (400 MHz, CDCl$_3$): δ=2.02 (s, 3H), 4.42 (m, 4H), 6.40 (d, 1H), 6.52 (d, 1H), 7.08~7.20 (m, 2H), 7.35~9.58 (m, 12H)

A polymer A-11 was obtained in the same manner as in Synthesis of polymer A-4, except that, in Synthesis of polymer A-4, the 2-(2-methacryloxyethyl)-1-naphthoic acid phosphine oxide E-12 was used instead of the methacrylate E-2.

<Synthesis of B-1>

—Synthesis of acrylate E-13—

In a 500 mL three-neck flask equipped with a stirring rod and a thermometer, 9.15 g (28.09 mmol) of cesium carbonate was added to a mixed solution of dimethylformamide (DMF) (40 mL) and pure water (8 mL), and the resultant was dissolved. Thereafter, the obtained mixed solution was concentrated by being stirred for 12 hours under reduced pressure. After 1.11 g (15.45 mmol) of acrylic acid was added thereto, a dimethylformamide (DMF, 30 mL) solution containing 6.0 g (14.04 mmol) of the benzyl bromide intermediate E-1 was also added thereto, and the resultant was stirred for 5 hours at room temperature (25° C.). Water was added to the reaction liquid, and the reaction product was extracted twice by using ethyl acetate. Subsequently, by column chromatography (hexane:ethyl acetate=8:2), an acrylate E-13 was isolated.

$^1$H NMR (400 MHz, CDCl$_3$): δ=2.04 (s, 6H), 5.10 (s, 2H), 5.86 (d, 1H), 6.11~6.21 (m, 1H), 6.42 (d, 1H), 7.01 (s, 2H), 7.47~7.66 (m, 6H), 7.96~8.07 (m, 4H)

—Synthesis of B-1—

In a 100 mL three-neck flask equipped with a stirring rod and a thermometer, 2.0 g (4.78 mmol) of the acrylate E-13, 0.43 g (1.19 mmol) of trimethylolpropane tris(thioglycolate) (manufactured by Tokyo Chemical Industry Co., Ltd.), and 0.5 ml of triethylamine were dissolved in acetonitrile (5 mL), and the resultant was stirred for 5 hours at 40° C. Water was added to the reaction liquid, and the reaction product was extracted twice by using ethyl acetate. Thereafter, by column chromatography (hexane:ethyl acetate=4:6), a compound B-1 was isolated.

B-1 Elemental Analysis:

Found: C, 64.82; H, 5.56.

Calcd. for C$_{87}$H$_{89}$O$_{18}$P$_3$S$_3$: C, 64.83; H, 5.57.

<Synthesis of B-2 and B-3>

A compound B-2 and a compound B-3 were obtained in the same manner as in Synthesis of B-1, except that, in Synthesis of B-1, trimethylolpropane tris(3-mercaptopropionate) or pentaerythritol tetra(3-mercaptopropionate) were used instead of trimethylolpropane tris(thioglycolate).

B-2 Elemental Analysis:

Found: C, 64.45; H, 5.36.

Calcd. for C$_{113}$H$_{112}$O$_{24}$P$_4$S$_4$: C, 64.44; H, 5.36.

B-3 Elemental Analysis:

Found: C, 65.35; H, 5.80.

Calcd. for C$_{90}$H$_{95}$O$_{18}$P$_3$S$_3$: C, 65.36; H, 5.79.

<Synthesis of B-4>

2.5 g (5.85 mmol) of the benzyl bromide intermediate E-1, 0.22 g (1.17 mmol) of citric acid, 0.49 g (5.85 mmol) of sodium hydrogen carbonate, and 20 mL of N-methyl-2-pyrrolidone (NMP) were put into a 100 mL three-neck flask equipped with a stirring rod, a nitrogen introduction pipe, and a thermometer, and the resultant was heated and stirred for 8 hours at 75° C. The solution obtained after the reaction was left to cool, water was then added thereto, and the reaction product was extracted twice by using ethyl acetate. Thereafter, by column chromatography (hexane:ethyl acetate: 5:5), a compound B-4 was isolated.

B-4 Elemental Analysis:

Found: C, 69.41; H, 5.45.

Calcd. for C$_{152}$H$_{142}$N$_2$O$_{28}$P$_6$: C, 69.40; H, 5.44.

<Synthesis of B-6, B-7, and B-8>

A compound B-6, a compound B-7, and a compound B-8 were obtained in the same manner as in Synthesis of B-4, except that, in Synthesis of B-4, the corresponding polyvalent carboxylic acid was used instead of citric acid.

B-6 Elemental Analysis:
 Found: C, 68.76; H, 5.53.
 Calcd. for $C_{159}H_{152}O_{27}P_6S_3$: C, 68.77; H, 5.52.

B-7 Elemental Analysis:
 Found: C, 68.64; H, 5.44.
 Calcd. for $C_{210}H_{198}O_{36}P_8S_4$: C, 68.65; H, 5.43.

B-8 Elemental Analysis:
 Found: C, 66.10; H, 4.74.
 Calcd. for $C_{90}H_{77}O_{18}P_3S_3$: C, 66.09; H, 4.74.

<Synthesis of B-5>

2.0 g (4.68 mmol) of the compound B-4, 0.31 g (1.87 mmol) of hexamethylene diisocyanate, 0.05 g of Neostann U-600, and 4.0 mL of NMP were put into a 100 mL three-neck flask equipped with a stirring rod, a nitrogen introduction pipe, and a thermometer, and the resultant was stirred for 8 hours at 60° C. The solution obtained after the reaction was left to cool, water was then added thereto, and the reaction product was extracted twice by using ethyl acetate. Thereafter, by column chromatography (hexane:ethyl acetate=7:3), a compound B-5 was isolated.

B-5 Elemental Analysis:
 Found: C, 69.41; H, 5.42.
 Calcd. for $C_{152}H_{142}N_2O_{28}P_6$: C, 69.40; H, 5.44.

<Synthesis of B-9>

10 g of 2-hydroxy-4,6-dimethylbenzaldehyde (synthesized by the method described in WO2004/87626A or the method described in Journal of Organometallic Chemistry, 2005, vol. 690, #23, p. 5125~5144), 8.09 g of triethylamine, and 70 ml of tetrahydrofuran were put into a 200 mL three-neck flask equipped with a stirring rod and a thermometer. Thereafter, 13.9 g of 4-chloromethylbenzoyl chloride was added dropwise thereto for 1 hour at 0° C., then the resultant was stirred for 2 hours at room temperature. Water was added to the reaction liquid, the reaction product was extracted twice by using ethyl acetate, and then by column chromatography (hexane:ethyl acetate=4:6), 16.5 g of a chloromethylbenzoyl-protected compound E-15 was obtained.

Subsequently, 70 ml of toluene, 16.5 g of the chloromethylbenzoyl-protected compound E-15, and 14.3 g of diphenylphosphine oxide were put into a 200 mL three-neck flask equipped with a stirring rod and a thermometer. Then, 1.0 g of sodium methoxide was added thereto, and the resultant was stirred for 2 hours. The solution obtained after the reaction was filtered and washed, thereby obtaining 23.4 g of a phosphine oxide adduct E-16.

Thereafter, in a 200 mL three-neck flask equipped with a stirring rod and a thermometer, 23.4 g of the phosphine oxide adduct E-16 was dissolved in 73 ml of chlorobenzene, 0.3 g of vanadium acetylacetonate and 6.2 g of tert-butylhydroperoxide were added thereto, and the resultant was stirred for 2 hours. Subsequently, an aqueous sodium sulfite solution was added to the reaction liquid, the resultant was subjected to liquid separation, and the organic phase was concentrated. Then, by column chromatography (hexane:ethyl acetate=3:7), 16.3 g of acylphosphine oxide E-17 was isolated.

16.3 g of acylphosphine oxide, 1.98 g of 1,3,5-tricarboxybenzene, and 5.38 g of potassium carbonate were added to 100 ml of N,N-dimethylacetamide (DMAC), and then the resultant was stirred for 7 hours at 80° C. Water was added to the reaction liquid, and the reaction product was extracted twice by using ethyl acetate. Thereafter, by column chromatography (hexane:ethyl acetate=4:6), 9.5 g of a compound B-9 was isolated.

B-9 Elemental Analysis:
 Found: C, 71.65; H, 4.70.
 Calcd. for $C_{96}H_{75}O_{18}P_3$: C, 71.64; H, 4.70.

<Synthesis of B-10>

100 ml of acetone, 10 g of 2-hydroxy-4,6-dimethylbenzaldehyde (synthesized by the method described in WO2004/87626A or the method described in Journal of Organometallic Chemistry, 2005, vol. 690, #23, p. 5125~5144), 8.9 g of allyl bromide, and 11.0 g of potassium carbonate were put into a 200 mL three-neck flask equipped with a stirring rod and a thermometer, and the resultant was stirred for 20 hours under reflux. Water was added to the reaction liquid, and the reaction product was extracted twice by using ethyl acetate. Thereafter, by column chromatography (hexane:ethyl acetate=4:6), 10.1 g of an allyl-protected compound E-18 was obtained.

Then, 70 ml of toluene, 10.1 g of the allyl-protected compound E-18, and 14.0 g of diphenylphosphine oxide were put into a 200 mL three-neck flask equipped with a stirring rod and a thermometer, 0.8 g of sodium methoxide was then added thereto, and the resultant was stirred for 2 hours. The solution obtained after the reaction was filtered and washed, thereby obtaining 16.7 g of a phosphine oxide adduct E-19.

Subsequently, in a 200 mL three-neck flask equipped with a stirring rod and a thermometer, 16.7 g of the phosphine oxide adduct E-19 was dissolved in 60 ml of chlorobenzene. Furthermore, 0.3 g of vanadium acetylacetonate and 5.8 g of tert-butylhydroperoxide were added thereto, and the resultant was stirred for 2 hours. Then, an aqueous sodium sulfite solution was added to the reaction liquid, the resultant was subjected to liquid separation, and the organic phase was concentrated. Thereafter, by column chromatography (hexane:ethyl acetate=3:7), 13.2 g of acylphosphine oxide E-20 was obtained.

Next, 13.2 g of the acylphosphine oxide E-20 and 3.5 g of pentaerythritol tetrathioglycolate were added to 100 ml of toluene, and then the resultant was heated to 80° C. 0.28 g of 2,2'-azobis(isobutyronitrile) was added thereto, and the resultant was stirred as is for 6 hours. Water was added to the reaction liquid, the reaction product was extracted twice by using ethyl acetate, and then by column chromatography (hexane:ethyl acetate=4:6), 10.7 g of a compound B-10 was obtained.

B-10 Elemental Analysis:
 Found: C, 65.66; H, 5.66.
 Calcd. for $C_{109}H_{112}O_{20}P_4S_4$: C, 65.65; H, 5.66.

<Synthesis of B-11>

100 ml of water, 10 g of 2-hydroxy-4,6-dimethylbenzaldehyde (synthesized by the method described in WO2004/87626A or the method described in Journal of Organometallic Chemistry, 2005, vol. 690, #23, p. 5125~5144), 6.4 g of 2-chloroethanol, and 4.0 g of sodium hydroxide were put into a 200 mL three-neck flask equipped with a stirring rod and a thermometer, and the resultant was stirred for 15 hours under reflux. Water was added to the reaction liquid, the reaction product was extracted twice by using ethyl acetate, and then by column chromatography (hexane:ethyl acetate=4:6), 9.71 g of 2-hydroxyethyl-4,6-dimethylbenzaldehyde E-21 was obtained. 100 ml of tetrahydrofuran, 9.71 g of the 2-hydroxyethyl-4,6-dimethylbenzaldehyde E-21, and 7.59 g of triethylamine were put into a 200 mL three-neck flask equipped with a stirring rod and a thermometer, and then 6.87 g of methanesulfonyl chloride was added dropwise thereto for 1 hour at 0° C. Thereafter, the solution obtained after the dropwise addition was stirred for 2 hours at room temperature. Water was added to the reaction liquid, the reaction product was extracted twice by using ethyl acetate, and then by column chromatography (hexane:ethyl acetate=4:6), 11.6 g of a methyl-protected compound E-22 was obtained.

Subsequently, 55 ml of toluene, 11.6 g of the methyl-protected compound E-22, and 11.2 g of diphenylphosphine oxide were put into a 200 mL three-neck flask equipped with a stirring rod and a thermometer, 1.0 g of sodium methoxide was then added thereto, and the resultant was stirred for 2 hours. The solution obtained after the reaction was filtered and washed, thereby obtaining 16.1 g of a phosphine oxide adduct E-23.

Then, in a 200 mL three-neck flask equipped with a stirring rod and a thermometer, 16.1 g of the phosphine oxide adduct E-23 was dissolved in 60 ml of chlorobenzene. 0.2 g of vanadium acetylacetonate and 4.6 g of tert-butyl-hydroperoxide were added thereto, and the resultant was stirred for 2 hours. An aqueous sodium sulfite solution was added to the solution obtained after the stirring, the resultant was subjected to liquid separation, and the organic phase was concentrated. Thereafter, by column chromatography (hexane:ethyl acetate=5:5), 12.9 g of acylphosphine oxide E-24 was obtained.

12.9 g of the acylphosphine oxide E-24, 1.66 g of pyromellitic acid, and 4.51 g of potassium carbonate were added to 100 ml of DMAC, and the resultant was stirred for 7 hours at 80° C. Water was added to the reaction liquid, the reaction product was extracted twice by using ethyl acetate, and then by column chromatography (hexane:ethyl acetate=4:6), 8.6 g of a compound B-11 was isolated.

B-11 Elemental Analysis:
Found: C, 69.61; H, 5.16.
Calcd. for $C_{102}H_{90}O_{20}P_4$: C, 69.62; H, 5.16.

<Synthesis of B-12>

12.3 g of 2-acetoxy-4,6-dimethylbenzaldehyde, 80 ml of toluene, 16.5 g of the chloromethylbenzoyl-protected compound E-15, and 16.8 g of diphenylphosphine oxide were put into a 200 mL three-neck flask equipped with a stirring rod and a thermometer, 0.8 g of sodium methoxide was then added thereto, and the resultant was stirred for 2 hours. The solution after the reaction was filtered and washed, thereby obtaining 22.7 g of a phosphine oxide adduct E-26.

Thereafter, in a 200 mL three-neck flask equipped with a stirring rod and a thermometer, 22.7 g of the phosphine oxide adduct E-26 was dissolved in 60 ml of chlorobenzene. Furthermore, 0.2 g of vanadium acetylacetonate and 5.3 g of tert-butylhydroperoxide were added thereto, and the resultant was stirred for 2 hours. Then, an aqueous sodium sulfite solution was added to the reaction liquid, the resultant was subjected to liquid separation, and the organic phase was concentrated. Subsequently, by column chromatography (hexane:ethyl acetate=3:7), 12.0 g of acylphosphine oxide E-27 was obtained.

12.0 g of the acylphosphine oxide E-27 and 10.57 g of potassium carbonate were added to 100 ml of ethanol, and then the resultant was stirred for 7 hours at room temperature. Water was added to the reaction liquid, the reaction product was extracted twice by using ethyl acetate, and then by column chromatography (hexane:ethyl acetate=4:6), 9.43 g of a deprotected compound E-28 was obtained.

Meanwhile, 15 g of pentaerythritol, 16.7 g of triethylamine, and 70 ml of DMF were put into a 200 mL three-neck flask equipped with a stirring rod and a thermometer, and then 93.7 g of chloromethylbenzoyl chloride was added dropwise thereto for 1 hour at 0° C. The solution obtained after the dropwise addition was stirred for 2 hours at 60° C., thereby obtaining 45.2 g of a chloromethylbenzoyl-protected compound E-29.

50 ml of DMF, 4.6 g of the chloromethylbenzoyl-protected compound E-29, 9.07 g of the deprotected compound E-28, and 4.26 g of potassium carbonate were put into a 200 mL three-neck flask equipped with a stirring rod and a thermometer, and the resultant was stirred for 7 hours at 80° C., thereby obtaining 9.25 g of a compound B-12.

B-12 Elemental Analysis:
Found: C, 72.60; H, 5.24.
Calcd. for $C_{121}H_{104}O_{20}P_4$: C, 72.59; H, 5.24.

<Synthesis of B-13>

A compound B-13 was obtained in the same manner as in Synthesis of B-9, except that, in Synthesis of B-9,5-chloro-2-hydroxy-4,6-dimethylbenzaldehyde (synthesized by the method described in WO2004/87626A or the method described in Journal of Organometallic Chemistry, 2005, vol. 690, #23, p. 5125~5144) was used instead of 2-hydroxy-4,6-dimethylbenzaldehyde.

B-13 Elemental Analysis:
Found: C, 67.32; H, 4.23.
Calcd. for $C_{96}H_{72}O_{18}Cl_3P_3$: C, 67.32; H, 4.24.

<Synthesis of B-14>

A compound B-14 was obtained in the same manner as in Synthesis of B-9, except that, in Synthesis of B-9,2-hydroxy-3,6-dimethylbenzaldehyde (synthesized by the method described in WO2004/87626A or the method described in Journal of Organometallic Chemistry, 2005, vol. 690, #23, p. 5125~5144) was used instead of 2-hydroxy-4,6-dimethylbenzaldehyde.

B-14 Elemental Analysis:
Found: C, 72.48; H, 4.83.
Calcd. for $C_{96}H_{77}O_{17}P_3$: C, 72.47; H, 4.83.

<Synthesis of B-15>

A compound B-15 was obtained in the same manner as in Synthesis of B-9, except that, in Synthesis of B-9,2-hydroxy-3,4,6-trimethylbenzaldehyde (synthesized by the method described in WO2004/87626A or the method described in Journal of Organometallic Chemistry, 2005, vol. 690, #23, p. 5125~5144) was used instead of 2-hydroxy-4,6-dimethylbenzaldehyde.

B-15 Elemental Analysis:
Found: C, 72.00; H, 4.95.
Calcd. for $C_{99}H_{81}O_{18}P_3$: C, 71.99; H, 4.94.

<Synthesis of B-16>

A compound B-16 was obtained in the same manner as in Synthesis of B-9, except that, in Synthesis of B-9,2-hydroxy-6-methyl-3-tert-butylbenzaldehyde (synthesized by the method described in WO2004/87626A or the method described in Journal of Organometallic Chemistry, 2005, vol. 690, #23, p. 5125~5144) was used instead of 2-hydroxy-4,6-dimethylbenzaldehyde.

B-16 Elemental Analysis:
Found: C, 72.66; H, 5.40.
Calcd. for $C_{105}H_{93}O_{18}P_3$: C, 72.65; H, 5.40.

<Synthesis of B-17>

A compound B-17 was obtained in the same manner as in Synthesis of B-9, except that, in Synthesis of B-9,2-hydroxy-6-methyl-3-isopropylbenzaldehyde (synthesized by the method described in WO2004/87626A or the method described in Journal of Organometallic Chemistry, 2005, vol. 690, #23, p. 5125~5144) was used instead of 2-hydroxy-4,6-dimethylbenzaldehyde.

B-17 Elemental Analysis:
Found: C, 72.32; H, 5.19.
Calcd. for $C_{102}H_{87}O_{18}P_3$: C, 72.33; H, 5.18.

<Synthesis of B-18>

A compound B-18 was obtained in the same manner as in Synthesis of B-9, except that, in Synthesis of B-9,2-hydroxy-3-methyl-6-isopropylbenzaldehyde (synthesized by the method described in WO2004/87626A or the method described in Journal of Organometallic Chemistry, 2005, vol. 690, #23, p. 5125~5144) was used instead of 2-hydroxy-4,6-dimethylbenzaldehyde.

B-18 Elemental Analysis:
 Found: C, 72.34; H, 5.18.
 Calcd. for $C_{102}H_{87}O_{18}P_3$: C, 72.33; H, 5.18.

<Preparation of Cyan Millbase A>

300 parts by mass of IRGACURE BLUE GLVO (a cyan pigment, manufactured by BASF Japan Ltd.), 620 parts by mass of SR9003 (PO-modified neopentyl glycol diacrylate, manufactured by Sartomer Company, Inc.), and 80 parts by mass of SOLSPERSE 32000 (manufactured by The Lubrizol Corporation.) were stirred and mixed together, thereby obtaining a cyan millbase A. The cyan millbase A was prepared by dispersing the mixture at a circumferential speed of 9 m/s for 4 hours by using a disperser Motor Mill M50 (manufactured by Eiger Co., Ltd.) and zirconia beads having a diameter of 0.65 mm.

Examples 1 to 45 and Comparative Examples 1 to 4

Manufacturing Method of Ink Composition

The materials shown in Tables 1 to 3 were mixed and stirred together in the amounts (parts by mass) shown in Tables 1 to 3, thereby obtaining the respective ink compositions.

TABLE 1

| | Cyan millbase A | Polymerizable compound | | | | | Polymerization initiator | | | | | | |
| --- | --- | --- | --- | --- | --- | --- | --- | --- | --- | --- | --- | --- | --- |
| | | TPGDA | EOTMPTA | NPGPODA | A-TMMT | DVE-3 | A-1 | A-2 | A-3 | A-4 | A-5 | A-6 | A-7 |
| Example 1 | 2.4 | 74.9 | 10 | 3.6 | — | — | 5 | — | — | — | — | — | — |
| Example 2 | 2.4 | 74.9 | 10 | 3.6 | — | — | — | 5 | — | — | — | — | — |
| Example 3 | 2.4 | 74.9 | 10 | 3.6 | — | — | — | — | 5 | — | — | — | — |
| Example 4 | 2.4 | 74.9 | 10 | 3.6 | — | — | — | — | — | 5 | — | — | — |
| Example 5 | 2.4 | 74.9 | 10 | 3.6 | — | — | — | — | — | — | 5 | — | — |
| Example 6 | 2.4 | 74.9 | 10 | 3.6 | — | — | — | — | — | — | — | 5 | — |
| Example 7 | 2.4 | 74.9 | 10 | 3.6 | — | — | — | — | — | — | — | — | 5 |
| Example 8 | 2.4 | 74.9 | 10 | 3.6 | — | — | — | — | — | — | — | — | — |
| Example 9 | 2.4 | 74.9 | 10 | 3.6 | — | — | — | — | — | — | — | — | — |
| Example 10 | 2.4 | 74.9 | 10 | 3.6 | — | — | — | — | — | — | — | — | — |
| Example 11 | 2.4 | 74.9 | 10 | 3.6 | — | — | — | — | — | — | — | — | — |
| Example 12 | 2.4 | 76.9 | 10 | 3.6 | — | — | — | — | — | 3 | — | — | — |
| Example 13 | 2.4 | 64.9 | 10 | 3.6 | — | — | — | — | — | 10 | — | — | — |
| Example 14 | 2.4 | 74.9 | — | 3.6 | 10 | — | 5 | — | — | — | — | — | — |
| Example 15 | 2.4 | 74.9 | — | 3.6 | — | 10 | 5 | — | — | — | — | — | — |
| Example 16 | 2.4 | 74.9 | 10 | 3.6 | — | — | 5 | — | — | — | — | — | — |
| Example 17 | 2.4 | 74.9 | 10 | 3.6 | — | — | 5 | — | — | — | — | — | — |
| Example 18 | 2.4 | 74.9 | 10 | 3.6 | — | — | 5 | — | — | — | — | — | — |
| Comparative example 1 | 2.4 | 74.9 | 10 | 3.6 | — | — | — | — | — | — | — | — | — |
| Comparative example 2 | 2.4 | 74.9 | 10 | 3.6 | — | — | — | — | — | — | — | — | — |
| Comparative example 3 | 2.4 | 74.9 | 10 | 3.6 | — | — | — | — | — | — | — | — | — |
| Comparative example 4 | 2.4 | 74.9 | 10 | 3.6 | — | — | — | — | — | — | — | — | — |

TABLE 1-continued

| | Polymerization initiator | | | | | | | | Sensitizer | | | Surfactant |
| | | | | | LUCIRIN | | | | | | | |
| | A-8 | A-9 | A-10 | A-11 | TPO | C-1 | C-2 | C-3 | SPEEDCURE7010 | ITX | DBA | BYK307 |
|---|---|---|---|---|---|---|---|---|---|---|---|---|
| Example 1 | — | — | — | — | — | — | — | — | 4 | — | — | 0.1 |
| Example 2 | — | — | — | — | — | — | — | — | 4 | — | — | 0.1 |
| Example 3 | — | — | — | — | — | — | — | — | 4 | — | — | 0.1 |
| Example 4 | — | — | — | — | — | — | — | — | 4 | — | — | 0.1 |
| Example 5 | — | — | — | — | — | — | — | — | 4 | — | — | 0.1 |
| Example 6 | — | — | — | — | — | — | — | — | 4 | — | — | 0.1 |
| Example 7 | — | — | — | — | — | — | — | — | 4 | — | — | 0.1 |
| Example 8 | 5 | — | — | — | — | — | — | — | 4 | — | — | 0.1 |
| Example 9 | — | 5 | — | — | — | — | — | — | 4 | — | — | 0.1 |
| Example 10 | — | — | 5 | — | — | — | — | — | 4 | — | — | 0.1 |
| Example 11 | — | — | — | 5 | — | — | — | — | 4 | — | — | 0.1 |
| Example 12 | — | — | — | — | — | — | — | — | 4 | — | — | 0.1 |
| Example 13 | — | — | — | — | — | — | — | — | 4 | — | — | 0.1 |
| Example 14 | — | — | — | — | — | — | — | — | 4 | — | — | 0.1 |
| Example 15 | — | — | — | — | — | — | — | — | 4 | — | — | 0.1 |
| Example 16 | — | — | — | — | — | — | — | — | — | — | — | 0.1 |
| Example 17 | — | — | — | — | — | — | — | — | — | 4 | — | 0.1 |
| Example 18 | — | — | — | — | — | — | — | — | — | — | 4 | 0.1 |
| Comparative example 1 | — | — | — | — | 5 | — | — | — | — | — | — | 0.1 |
| Comparative example 2 | — | — | — | — | — | 5 | — | — | — | — | — | 0.1 |
| Comparative example 3 | — | — | — | — | — | — | 5 | — | — | — | — | 0.1 |
| Comparative example 4 | — | — | — | — | — | — | — | 5 | — | — | — | 0.1 |

TABLE 2

| | Cyan | Polymerizable compound | | | | | Polymerization initiator | | | | |
| | millbase A | TPGDA | EOTMPTA | NPGPODA | A-TMMT | DVE-3 | B-1 | B-2 | B-3 | B-4 | B-5 |
|---|---|---|---|---|---|---|---|---|---|---|---|
| Example 19 | 2.4 | 74.9 | 10 | 3.6 | — | — | 5 | — | — | — | — |
| Example 20 | 2.4 | 74.9 | 10 | 3.6 | — | — | — | 5 | — | — | — |
| Example 21 | 2.4 | 74.9 | 10 | 3.6 | — | — | — | — | 5 | — | — |
| Example 22 | 2.4 | 74.9 | 10 | 3.6 | — | — | — | — | — | 5 | — |
| Example 23 | 2.4 | 74.9 | 10 | 3.6 | — | — | — | — | — | — | 5 |
| Example 24 | 2.4 | 74.9 | 10 | 3.6 | — | — | — | — | — | — | — |
| Example 25 | 2.4 | 74.9 | 10 | 3.6 | — | — | — | — | — | — | — |
| Example 26 | 2.4 | 74.9 | 10 | 3.6 | — | — | — | — | — | — | — |
| Example 27 | 2.4 | 76.9 | 10 | 3.6 | — | — | 3 | — | — | — | — |
| Example 28 | 2.4 | 64.9 | 10 | 3.6 | — | — | 10 | — | — | — | — |
| Example 29 | 2.4 | 74.9 | — | 3.6 | 10 | — | 5 | — | — | — | — |
| Example 30 | 2.4 | 74.9 | — | 3.6 | — | 10 | 5 | — | — | — | — |
| Example 31 | 2.4 | 74.9 | 10 | 3.6 | — | — | 5 | — | — | — | — |
| Example 32 | 2.4 | 74.9 | 10 | 3.6 | — | — | 5 | — | — | — | — |
| Example 33 | 2.4 | 74.9 | 10 | 3.6 | — | — | 5 | — | — | — | — |
| Example 34 | 2.4 | 74.9 | 10 | 3.6 | — | — | 5 | — | — | — | — |

TABLE 2-continued

| | Polymerization initiator | | | | | Sensitizer | | | | Surfactant |
|---|---|---|---|---|---|---|---|---|---|---|
| | B-6 | B-7 | B-8 | LUCIRIN TPO | C-1 | SPEEDCURE7010 | ITX | DBA | X | BYK307 |
| Example 19 | — | — | — | — | — | 4 | — | — | — | 0.1 |
| Example 20 | — | — | — | — | — | 4 | — | — | — | 0.1 |
| Example 21 | — | — | — | — | — | 4 | — | — | — | 0.1 |
| Example 22 | — | — | — | — | — | 4 | — | — | — | 0.1 |
| Example 23 | — | — | — | — | — | 4 | — | — | — | 0.1 |
| Example 24 | 5 | — | — | — | — | 4 | — | — | — | 0.1 |
| Example 25 | — | 5 | — | — | — | 4 | — | — | — | 0.1 |
| Example 26 | — | — | 5 | — | — | 4 | — | — | — | 0.1 |
| Example 27 | — | — | — | — | — | 4 | — | — | — | 0.1 |
| Example 28 | — | — | — | — | — | 4 | — | — | — | 0.1 |
| Example 29 | — | — | — | — | — | 4 | — | — | — | 0.1 |
| Example 30 | — | — | — | — | — | 4 | — | — | — | 0.1 |
| Example 31 | — | — | — | — | — | — | — | — | — | 0.1 |
| Example 32 | — | — | — | — | — | — | 4 | — | — | 0.1 |
| Example 33 | — | — | — | — | — | — | — | 4 | — | 0.1 |
| Example 34 | — | — | — | — | — | — | — | — | 4 | 0.1 |

TABLE 3

| | Cyan | Polymerizable compound | | | | | Polymerization initiator | | | |
|---|---|---|---|---|---|---|---|---|---|---|
| | millbase A | TPGDA | EOTMPTA | NPGPODA | A-TMMT | DVE-3 | B-9 | B-10 | B-11 | B-12 |
| Example 36 | 2.4 | 74.9 | 10 | 3.6 | — | — | 5 | — | — | — |
| Example 37 | 2.4 | 74.9 | 10 | 3.6 | — | — | — | 5 | — | — |
| Example 38 | 2.4 | 74.9 | 10 | 3.6 | — | — | — | — | 5 | — |
| Example 39 | 2.4 | 74.9 | 10 | 3.6 | — | — | — | — | — | 5 |
| Example 40 | 2.4 | 74.9 | 10 | 3.6 | — | — | — | — | — | — |
| Example 41 | 2.4 | 74.9 | 10 | 3.6 | — | — | — | — | — | — |
| Example 42 | 2.4 | 74.9 | 10 | 3.6 | — | — | — | — | — | — |
| Example 43 | 2.4 | 74.9 | 10 | 3.6 | — | — | — | — | — | — |
| Example 44 | 2.4 | 74.9 | 10 | 3.6 | — | — | — | — | — | — |
| Example 45 | 2.4 | 76.9 | 10 | 3.6 | — | — | — | — | — | — |

| | Polymerization initiator | | | | | | Sensitizer | | | Surfactant |
|---|---|---|---|---|---|---|---|---|---|---|
| | B-13 | B-14 | B-15 | B-16 | B-17 | B-18 | SPEEDCURE7010 | ITX | DBA | BYK307 |
| Example 36 | — | — | — | — | — | — | 4 | — | — | 0.1 |
| Example 37 | — | — | — | — | — | — | 4 | — | — | 0.1 |
| Example 38 | — | — | — | — | — | — | 4 | — | — | 0.1 |
| Example 39 | — | — | — | — | — | — | 4 | — | — | 0.1 |
| Example 40 | 5 | — | — | — | — | — | 4 | — | — | 0.1 |
| Example 41 | — | 5 | — | — | — | — | 4 | — | — | 0.1 |
| Example 42 | — | — | 5 | — | — | — | 4 | — | — | 0.1 |
| Example 43 | — | — | — | 5 | — | — | 4 | — | — | 0.1 |
| Example 44 | — | — | — | — | 5 | — | 4 | — | — | 0.1 |
| Example 45 | — | — | — | — | — | 5 | 4 | — | — | 0.1 |

The abbreviations shown in Tables 1 to 3 that were not described above are as follows.

<Polymerizable Compound (Monomer)>
TPGDA: tripropylene glycol diacrylate, SR306 manufactured by Sartomer Company, Inc.
NPGPODA: PO-modified neopentyl glycol diacrylate, SR9003 manufactured by Sartomer Company, Inc.
EOTMPTA: EO-modified trimethylolpropane triacrylate, SR454 manufactured by Sartomer Company, Inc.
A-TMMT: pentaerythritol tetraacrylate, manufactured by SHIN-NAKAMURA CHEMICAL CO., LTD.
DVE-3: bifunctional vinyl ether compound, triethylene glycol divinyl ether, manufactured by ISP Europe <Polymerization Initiator Other than Component A>
LUCIRIN TPO: 2,4,6-trimethylbenzoyl diphenylphosphine oxide, manufactured by Ciba-Geigy Japan Ltd.
C-1 (the following compound, Mw=21,100)
C-2 (the following compound, Mw=2,100)
C-3 (the following compound, Mw=800)

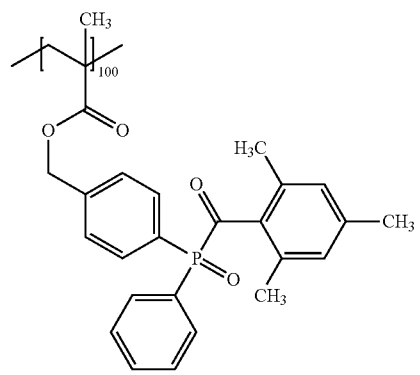

C-1 (Mw = 21,100)

-continued

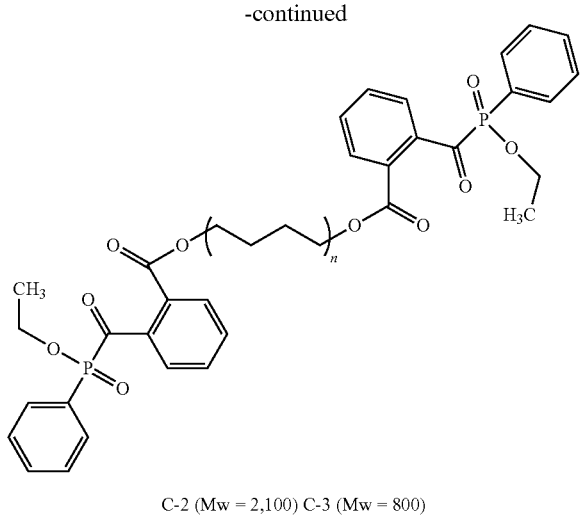

C-2 (Mw = 2,100) C-3 (Mw = 800)

<Sensitizer>

DBA (Anthcure UVS-1331): 9,10-dibutoxyanthracene, manufactured by KAWASAKI KASEI CHEMICALS.

ITX: isopropyl thioxanthone, manufactured by Ciba Specialty Chemicals Corporation.

SPEEDCURE 7010: molecular weight 1,899, manufactured by Lambson Limited

Sensitizer X (the following compound I-F)

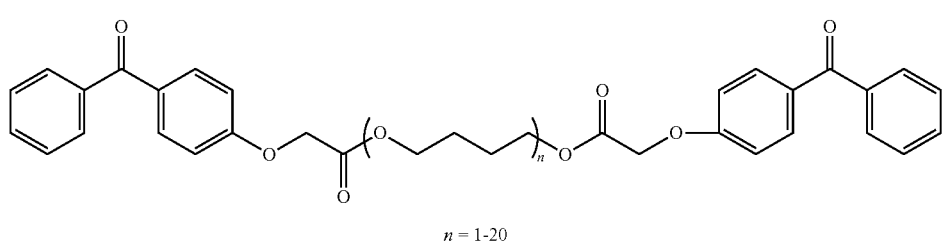

$n = 1\text{-}20$

<Surfactant>

BYK307: silicone-based surfactant, manufactured by BYK-Chemie GmbH

<Inkjet Recording Method>

As shown in FIG. 1, in an inkjet apparatus, as inkjet heads, four CA3 heads manufactured by TOSHIBA TEC CORPORATION were arranged in a line for each color. The heads were heated to 45° C., and the frequency thereof was controlled such that an image could be drawn by ejecting droplets in a size of 42 pL.

As a light source, an LED light source unit having a peak wavelength of 385 nm (LEDZero Solidcure, manufactured by Integration Technology Ltd) was disposed in the inert gas blanket.

Furthermore, as a source of inert gas, a $N_2$ gas generator Maxi-Flow30 (manufactured by Inhouse Gas Ltd) equipped with a compressor was connected to the gas blanket at a pressure of 0.2 MPa·s. The concentration of $N_2$ was set by causing $N_2$ to flow at a flow rate of 2 L/min to 10 L/min such that the concentration of $N_2$ (partial pressure of $N_2$) in the blanket fell into a range of 90% to 99%.

A 100% solid image was drawn by scanning Pylen film-OTP3162 (A4 size, polypropylene sheet, film thickness 40 μm) as a support at a rate of 30 m/min, thereby obtaining a printed article. The obtained printed article was evaluated in terms of various performances described below.

<Method for Evaluating Migration>

10 mL of a mixed liquid of water:ethanol=70:30 was dripped onto the surface of the printed article obtained by the aforementioned inkjet recording method, and the printed article was cut in a size of 1 $dm^2$. The cut printed article was put into an airtight container made of glass so as to prevent the mixed solution from volatilizing, and left for 10 days at 40° C. Thereafter, the overall migration amount (OML) of components that were eluted into the mixed liquid of water/ethanol from the printed article was calculated and evaluated on a scale of 1 to 5. Herein, the overall migration amount was measured in a manner in which the printed article was left for 10 days, the mixed liquid of water/ethanol was volatilized, and the mass of the residual components was measured.

5: The migration amount was equal to or less than 10 ppb.
4: The migration amount was greater than 10 ppb and equal to or less than 50 ppb.
3: The migration amount was greater than 50 ppb and equal to or less than 100 ppb.
2: The migration amount was greater than 100 ppb and equal to or less than 2,000 ppb.
1: The migration amount was greater than 2,000 ppb.

<Method for Evaluating Odor>

The printed article obtained by the aforementioned inkjet recording method was put into a 30 cm×30 cm plastic bag with a zipper and left for 24 hours.

Thereafter, the bag was unzipped to evaluate odor. For the evaluation, the average of the results obtained from 10 people was adopted. The evaluation criteria are as follows. Herein, the average was rounded off below the decimal point.

5: The printed article had almost no odor.
4: Although the printed article had slight odor, it was almost imperceptible.
3: Although the printed article had some odor, it was not offensive.
2: The printed article had odor.
1: The printed article had very strong odor.

<Method for Evaluating Adhesiveness with Respect to Substrate>

By the aforementioned inkjet recording method, a printed article was prepared by using Priplak (film thickness 0.8 mm, polypropylene sheet, manufactured by Robert Home Group) as a support, and the printed article was evaluated. The adhesiveness between the cured film and the substrate (support) in the printed article was evaluated by a cross hatch test (EN ISO2409) based on the following criteria 5B to 1B. According to the evaluation, the level 5B indicates the best adhesiveness, and the levels equal to or higher than the level 3B are unproblematic for practical use.

5B: Neither a missing portion nor curling of an edge was observed.
4B: Although no missing portion was observed, curling was slightly observed in an intersection point of lattices.
3B: Although no missing portion was observed, curling was slightly observed in four corners of lattices.
2B: A missing portion was observed at 1 to 5 points, and curling was observed in four corners of lattices.
1B: A missing portion was observed at 6 or more points, and curling was observed in four corners of lattices.

<Method for Evaluating Ejectability>

By using a piezoelectric inkjet head Q-class Sapphire QS-256/30 (manufactured by FUJIFILM DIMATIX, Inc., nozzle number 256, the minimum amount of droplets ejected 30 pL, 33 kHz) as an inkjet head installed in the inkjet apparatus, nozzle blocking resulting from the ink composition obtained as above was evaluated (evaluation of ejectability). The evaluation criteria are as follows. Herein, according to the evaluation, the level 5 indicates the best result, and the levels equal to or higher than the level 3 are unproblematic for practical use.
5: Nozzle blocking did not occur.
4: The number of nozzles in which nozzle blocking occurred was equal to or greater than 1 and equal to or less than 2.
3: The number of nozzles in which nozzle blocking occurred was equal to or greater than 3 and equal to or less than 5.
2: The number of nozzles in which nozzle blocking occurred was equal to or greater than 6 and equal to or less than 20.
1: The number of nozzles in which nozzle blocking occurred was equal to or greater than 21.

<Method for Evaluating Dispersion Stability>

10 ml of the ink composition was put in a plastic container, and then heated in an oven for 4 days at 60° C. Thereafter, the change in the average particle sizes of the pigment particles before and after heating in the oven were measured. Herein, the average particle size was measured by using SALD-7100H manufactured by Shimadzu Corporation. According to the evaluation, the level 5 indicates the best result, and the levels equal to or higher than the level 3 are unproblematic for practical use.
5: The change in the particle size was less than 0.1%.
4: The change in the particle size was equal to or greater than 0.1% and less than 1%.
3: The change in the particle size was equal to or greater than 1% and less than 2%.
2: The change in the particle size was equal to or greater than 2% and less than 5%.
1: The change in the particle size was equal to or greater than 5%.

The evaluation results of Examples 1 to 45 and Comparative examples 1 to 4 are shown in Tables 4 and 5.

TABLE 4

| | Migration | Odor | Adhesiveness OPP | Adhesiveness PET | Ejectability | Dispersion stability |
|---|---|---|---|---|---|---|
| Example 1 | 5 | 5 | 5B | 5B | 4 | 5 |
| Example 2 | 5 | 5 | 5B | 5B | 4 | 5 |
| Example 3 | 5 | 5 | 5B | 5B | 4 | 5 |
| Example 4 | 5 | 5 | 5B | 5B | 5 | 5 |
| Example 5 | 5 | 5 | 5B | 5B | 5 | 5 |
| Example 6 | 4 | 4 | 5B | 5B | 4 | 4 |
| Example 7 | 5 | 5 | 5B | 5B | 5 | 5 |
| Example 8 | 5 | 5 | 5B | 5B | 5 | 5 |
| Example 9 | 5 | 5 | 5B | 5B | 5 | 5 |
| Example 10 | 5 | 5 | 5B | 5B | 5 | 5 |
| Example 11 | 4 | 4 | 4B | 5B | 4 | 4 |
| Example 12 | 4 | 4 | 5B | 5B | 5 | 5 |
| Example 13 | 5 | 4 | 5B | 5B | 5 | 5 |
| Example 14 | 5 | 5 | 5B | 5B | 4 | 5 |
| Example 15 | 5 | 5 | 5B | 5B | 4 | 5 |
| Example 16 | 5 | 5 | 5B | 5B | 4 | 5 |
| Example 17 | 5 | 5 | 5B | 5B | 4 | 5 |
| Example 18 | 5 | 5 | 5B | 5B | 5 | 5 |
| Example 19 | 5 | 5 | 5B | 5B | 5 | 5 |
| Example 20 | 5 | 5 | 5B | 5B | 5 | 5 |
| Example 21 | 5 | 4 | 5B | 5B | 5 | 5 |
| Example 22 | 5 | 5 | 5B | 5B | 5 | 4 |
| Example 23 | 5 | 5 | 5B | 5B | 5 | 5 |
| Example 24 | 5 | 5 | 5B | 5B | 4 | 5 |
| Example 25 | 5 | 4 | 5B | 5B | 5 | 5 |
| Example 26 | 5 | 5 | 5B | 5B | 5 | 4 |
| Example 27 | 5 | 5 | 5B | 5B | 5 | 5 |
| Example 28 | 5 | 5 | 5B | 5B | 5 | 5 |
| Example 29 | 5 | 5 | 5B | 5B | 5 | 5 |
| Example 30 | 5 | 5 | 5B | 5B | 5 | 5 |
| Example 31 | 5 | 5 | 5B | 5B | 5 | 5 |
| Example 32 | 5 | 5 | 5B | 5B | 5 | 5 |
| Example 33 | 5 | 5 | 5B | 5B | 5 | 4 |
| Example 34 | 5 | 4 | 5B | 5B | 4 | 5 |
| Comparative example 1 | 1 | 2 | 1B | 2B | 5 | 2 |
| Comparative example 2 | 2 | 2 | 5B | 4B | 1 | 4 |
| Comparative example 3 | 3 | 2 | 2B | 3B | 2 | 3 |
| Comparative example 4 | 2 | 2 | 3B | 4B | 3 | 4 |

TABLE 5

| | Migration | Odor | Adhesiveness OPP | Adhesiveness PET | Ejectability | Dispersion stability |
|---|---|---|---|---|---|---|
| Example 36 | 5 | 5 | 5B | 4B | 4 | 5 |
| Example 37 | 5 | 5 | 5B | 4B | 4 | 5 |
| Example 38 | 5 | 5 | 5B | 4B | 4 | 4 |
| Example 39 | 5 | 5 | 5B | 4B | 4 | 5 |
| Example 40 | 4 | 5 | 5B | 4B | 4 | 5 |
| Example 41 | 5 | 5 | 5B | 4B | 4 | 5 |
| Example 42 | 5 | 5 | 5B | 4B | 5 | 4 |
| Example 43 | 5 | 5 | 5B | 4B | 4 | 5 |
| Example 44 | 5 | 5 | 5B | 4B | 4 | 5 |
| Example 45 | 5 | 5 | 5B | 4B | 4 | 5 |

What is claimed is:

1. An ink composition comprising:
   (component A) a high-molecular-weight polymerization initiator having a weight-average molecular weight of equal to or greater than 1,000;
   (component B) a polymerizable compound; and
   (component C) a colorant,
   wherein the component A is a hyperbranched polymer having a thioether bond and three or more acylphosphine oxide structures, and
   the acylphosphine oxide structure is linked to a core of the hyperbranched polymer such that an acyl group of the acylphosphine oxide structure is bonded to the core of the hyperbranched polymer through a linking group.

2. The ink composition according to claim 1,
   wherein the acylphosphine oxide structure is a monoacylphosphine oxide structure.

3. The ink composition according to claim 1,
wherein the acylphosphine oxide structure is a structure represented by the following Formula (1) or (2),

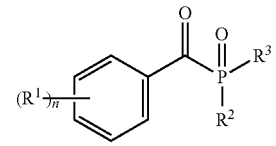

(1)

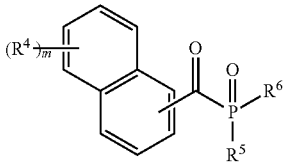

(2)

wherein in the formula, each $R^1$ independently represents an alkyl group having 1 to 8 carbon atoms, an aryl group, an alkoxy group having 1 to 4 carbon atoms, or the linking group linked to a main chain or a core of the component A; at least one $R^1$ is the linking group linked to the core of the hyperbranched polymer; each of $R^2$ and $R^3$ independently represents an alkyl group, an aryl group, or an alkoxy group; n represents an integer of 1 to 5; each $R^4$ independently represents an alkyl group having 1 to 8 carbon atoms, an aryl group, an alkoxy group having 1 to 4 carbon atoms, or the linking group linked to the core of the hyperbranched polymer; at least one $R^4$ is the linking group linked to the core of the hyperbranched polymer; each of $R^5$ and $R^6$ independently represents an alkyl group, an aryl group, or an alkoxy group; and m represents an integer of 1 to 7.

4. The ink composition according to claim 3,
wherein the acylphosphine oxide structure is a structure represented by Formula (1).

5. The ink composition according to claim 3,
wherein the acylphosphine oxide structure is a structure represented by Formula (2).

6. The ink composition according to claim 1,
wherein the acylphosphine oxide structure is a structure represented by the following Formula (1-1),

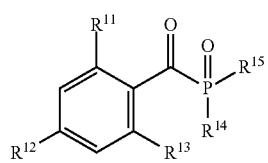

(1-1)

wherein in the formula, each of $R^{11}$ to $R^{13}$ independently represents a hydrogen atom, an alkyl group having 1 to 8 carbon atoms, an aryl group, an alkoxy group having 1 to 4 carbon atoms, or the linking group linked to the core of the hyperbranched polymer; at least one of $R^{11}$ to $R^{13}$ is the linking group linked to the core of the hyperbranched polymer; and each of $R^{14}$ and $R^{15}$ independently represents an alkyl group, an aryl group, or an alkoxy group.

7. The ink composition according to claim 1,
wherein the acylphosphine oxide structure is a structure represented by the following Formula (1-2),

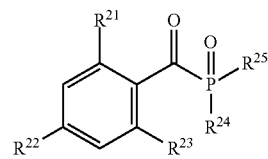

(1-2)

wherein in the formula, $R^{21}$ represents a hydrogen atom, an alkyl group having 1 to 8 carbon atoms, an aryl group, or an alkoxy group having 1 to 4 carbon atoms; one of $R^{22}$ and $R^{23}$ represents the linking group linked to the core of the hyperbranched polymer, and the other of $R^{22}$ and $R^{23}$ represents a hydrogen atom, an alkyl group having 1 to 8 carbon atoms, an aryl group, or an alkoxy group having 1 to 4 carbon atoms; and each of $R^{24}$ and $R^{25}$ independently represents an alkyl group, an aryl group, or an alkoxy group.

8. The ink composition according to claim 3,
wherein the acylphosphine oxide structure is a structure represented by the following Formula (1-2),

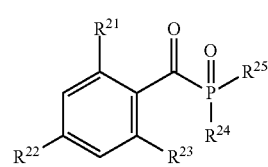

(1-2)

wherein in the formula, $R^{21}$ represents a hydrogen atom, an alkyl group having 1 to 8 carbon atoms, an aryl group, or an alkoxy group having 1 to 4 carbon atoms; one of $R^{22}$ and $R^{23}$ represents the linking group linked to the core of the hyperbranched polymer, and the other of $R^{22}$ and $R^{23}$ represents a hydrogen atom, an alkyl group having 1 to 8 carbon atoms, an aryl group, or an alkoxy group having 1 to 4 carbon atoms; and each of $R^{24}$ and $R^{25}$ independently represents an alkyl group, an aryl group, or an alkoxy group.

9. The ink composition according to claim 1, further comprising a compound represented by the following Formula (3),

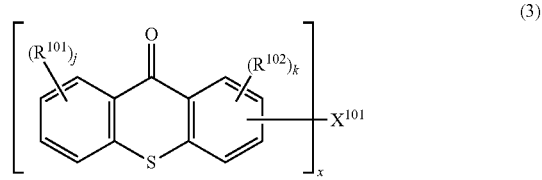

(3)

wherein in the formula, each of $R^{101}$ and $R^{102}$ independently represents an alkyl group having 1 to 5 carbon atoms or a halogen atom; x represents an integer of 2 to 4; j represents an integer of 0 to 4; k represents an integer of 0 to 3; when each of j and k is an integer of equal to or greater than 2, a plurality of $R^{101}$ and a plurality of $R^{102}$ may be the same as or different from each other respectively; and $X^{101}$ represents an x-valent hydrocarbon chain having 2 to 300 carbon atoms that may contain an ether bond and/or an ester bond.

10. The ink composition according to claim 3, further comprising a compound represented by the following Formula (3),

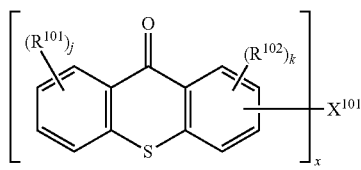

wherein in the formula, each of $R^{101}$ and $R^{102}$ independently represents an alkyl group having 1 to 5 carbon atoms or a halogen atom; x represents an integer of 2 to 4; j represents an integer of 0 to 4; k represents an integer of 0 to 3; when each of j and k is an integer of equal to or greater than 2, a plurality of $R^{101}$ and a plurality of $R^{102}$ may be the same as or different from each other respectively; and $X^{101}$ represents an x-valent hydrocarbon chain having 2 to 300 carbon atoms that may contain an ether bond and/or an ester bond.

11. An inkjet recording method comprising:
($a^1$) ejecting the ink composition according to claim 1 onto a recording medium; and
($b^1$) curing the ink composition by irradiating the ejected ink composition with an active energy ray.

12. A printed article produced by using the inkjet recording method according to claim 11.

13. A high-molecular-weight polymerization initiator which is a hyperbranched polymer having
a weight-average molecular weight of equal to or greater than 1,000 and
a thioether bond and three or more acylphosphine oxide structures represented by the following Formula (1) or (2) on a molecular terminal,

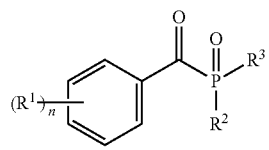

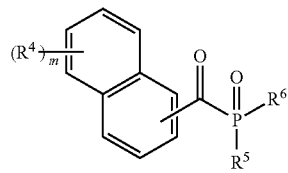

wherein in the formula, each $R^1$ independently represents an alkyl group having 1 to 8 carbon atoms, an aryl group, an alkoxy group having 1 to 4 carbon atoms, or a linking group linked to a core of a hyperbranched polymer; at least one $R^1$ is a linking group linked to a core of a hyperbranched polymer; each of $R^2$ and $R^3$ independently represents an alkyl group, an aryl group, or an alkoxy group; n represents an integer of 1 to 5; each $R^4$ independently represents an alkyl group having 1 to 8 carbon atoms, an aryl group, an alkoxy group having 1 to 4 carbon atoms, or a linking group linked to a core of a hyperbranched polymer; at least one $R^4$ is a linking group linked to a core of a hyperbranched polymer; each of $R^5$ and $R^6$ independently represents an alkyl group, an aryl group, or an alkoxy group; and m represents an integer of 1 to 7.

14. The high-molecular-weight polymerization initiator according to claim 13,
wherein the hyperbranched polymer has 3 to 10 of acylphosphine oxide structures represented from the Formula (1) or (2).

15. An ink composition comprising:
a colorant,
a polymerizable compound, and
the high-molecular-weight polymerization initiator according to claim 13.

16. An ink composition comprising:
(component A) a high-molecular-weight polymerization initiator having a weight-average molecular weight of equal to or greater than 1,000;
(component B) a polymerizable compound; and
(component C) a colorant, wherein
the component A has an acylphosphine oxide structure represented by Formula (2),
the acylphosphine oxide structure is linked to a core of the component A such that an acyl group of the acylphosphine oxide structure is bonded to the core of the Component A through a linking group, and

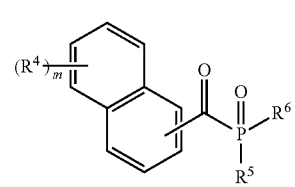

in Formula (2), each $R^4$ independently represents an alkyl group having 1 to 8 carbon atoms, an aryl group, an alkoxy group having 1 to 4 carbon atoms, or a linking group linked to the core of the Component A; at least one $R^4$ is the linking group linked to the core of the Component A; each of $R^5$ and $R^6$ independently represents an alkyl group, an aryl group, or an alkoxy group; and m represents an integer of 1 to 7.

* * * * *